United States Patent
Schumacher et al.

(10) Patent No.: US 7,932,248 B2
(45) Date of Patent: *Apr. 26, 2011

(54) 1H-INDAZOLES, BENZOTHIAZOLES, 1,2-BENZOISOXAZOLES, 1,2-BENZOISOTHIAZOLES, AND CHROMONES AND PREPARATION AND USES THEREOF

(75) Inventors: Richard Schumacher, Monroe, NY (US); Jianguo Ma, Natick, MA (US); Brian Herbert, Stockholm, NJ (US); Mihaela Diana Danca, Mendham, NJ (US); Wenge Xie, Mahwah, NJ (US); Truc Minh Nguyen, New York, NY (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 797 days.

This patent is subject to a terminal disclaimer.

(21) Appl. No.: 11/594,993

(22) Filed: Nov. 9, 2006

(65) Prior Publication Data

US 2007/0135417 A1 Jun. 14, 2007

Related U.S. Application Data

(60) Provisional application No. 60/734,761, filed on Nov. 9, 2005.

(51) Int. Cl.
*A61P 25/28* (2006.01)
*A61K 31/551* (2006.01)
*C07D 487/08* (2006.01)

(52) U.S. Cl. .......... 514/219; 514/221; 540/556
(58) Field of Classification Search .......... 514/219, 514/221; 540/556
See application file for complete search history.

(56) References Cited

U.S. PATENT DOCUMENTS 7,456,171 B2 * 11/2008 Galli et al. .......... 514/221

FOREIGN PATENT DOCUMENTS

| FR | 2 845 388 | | 4/2004 |
|---|---|---|---|
| WO | WO 2004/016616 | | 2/2004 |
| WO | 2004/033456 | * | 4/2004 |
| WO | WO 2005/063767 | | 7/2005 |

OTHER PUBLICATIONS

Schmitt et al., Targeting Nicotinic Acetylcholine Receptors: Advances in Molecular Design and Therapies, Annual Reports in Medicinal Chemistry, vol. 35, 2000, pp. 41-51.*
Int'l. Search Report and the Written Opinion of the Int'l. Searching Authority, issued Mar. 1, 2007 in PCT/US2006/04318.

* cited by examiner

*Primary Examiner* — Brenda L Coleman
(74) *Attorney, Agent, or Firm* — Millen, White, Zelano & Branigan, P.C.

(57) ABSTRACT

The present invention relates generally to the field of ligands for nicotinic acetylcholine receptors (nAChR), activation of nAChRs, and the treatment of disease conditions associated with defective or malfunctioning nicotinic acetylcholine receptors, especially of the brain. Further, this invention relates to novel compounds (indazoles and benzothiazoles), which act as ligands for the α7 nAChR subtype, methods of preparing such compounds, compositions containing such compounds, and methods of use thereof.

23 Claims, No Drawings

1H-INDAZOLES, BENZOTHIAZOLES, 1,2-BENZOISOXAZOLES, 1,2-BENZOISOTHIAZOLES, AND CHROMONES AND PREPARATION AND USES THEREOF

This application claims the benefit of U.S. Provisional Application Ser. No. 60/734,761, filed Nov. 9, 2005.

This application is related to U.S. application Ser. No. 11/123,219, filed May 6, 2005, which claims the benefit of U.S. Provisional Application Ser. No. 60/568,696, filed May 7, 2004, U.S. Provisional Application Ser. No. 60/574,712, filed May 27, 2004, and U.S. Provisional Application Ser. No. 60/629,469, filed Nov. 10, 2004, the entire disclosures of each of which are hereby incorporated by reference.

FIELD OF THE INVENTION

The present invention relates generally to the field of ligands for nicotinic acetylcholine receptors (nAChR), activation of nAChRs, and the treatment of disease conditions associated with defective or malfunctioning nicotinic acetylcholine receptors, especially of the brain. Further, this invention relates to novel compounds, which act as ligands for the α7 nAChR subtype, methods of preparing such compounds, compositions comprising such compounds, and methods of use thereof.

BACKGROUND OF THE INVENTION

There are two types of receptors for the neurotransmitter, acetylcholine: muscarinic receptors and nicotinic receptors, based on the selectivity of action of muscarine and nicotine, respectively. Muscarinic receptors are G-protein coupled receptors. Nicotinic receptors are members of the ligand-gated ion channel family. When activated, the conductance of ions across the nicotinic ion channels increases.

Nicotinic alpha-7 receptor protein forms a homo-pentameric channel in vitro that is highly permeable to a variety of cations (e.g., $Ca^{++}$). Each nicotinic alpha-7 receptor has four transmembrane domains, named M1, M2, M3, and M4. The M2 domain has been suggested to form the wall lining the channel. Sequence alignment shows that nicotinic alpha-7 is highly conserved during evolution. The M2 domain that lines the channel is identical in protein sequence from chicken to human. For discussions of the alpha-7 receptor, see, e.g., Revah et al. (1991), *Nature,* 353, 846-849; Galzi et al. (1992), *Nature* 359, 500-505; Fucile et al. (2000), *PNAS* 97(7), 3643-3648; Briggs et al. (1999), *Eur. J. Pharmacol.* 366 (2-3), 301-308; and Gopalakrishnan et al. (1995), *Eur. J. Pharmacol.* 290(3), 237-246.

The nicotinic alpha-7 receptor channel is expressed in various brain regions and is believed to be involved in many important biological processes in the central nervous system (CNS), including learning and memory. Nicotinic alpha-7 receptors are localized on both presynaptic and postsynaptic terminals and have been suggested to be involved in modulating synaptic transmission. It is therefore of interest to develop novel compounds, which act as ligands for the α7 nAChR subtype, for the treatment of disease conditions associated with defective or malfunctioning nicotinic acetylcholine receptors.

SUMMARY OF THE INVENTION

This invention relates to novel compounds, which act as ligands for the α7 nAChR subtype, methods of preparing such compounds, compositions comprising such compounds, and methods of use thereof.

DETAILED DESCRIPTION OF THE INVENTION

The present invention includes compounds of Formulas I, II, III, IV, V, VI, VII or VIII:

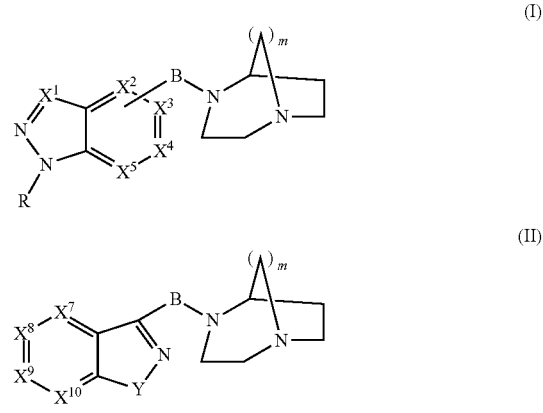

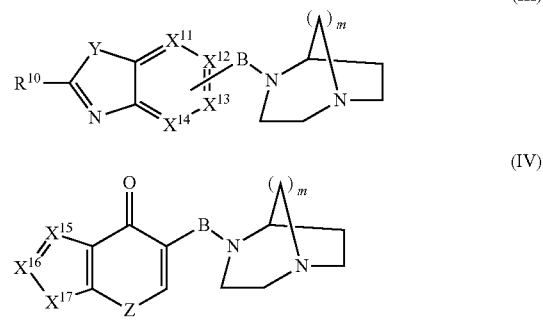

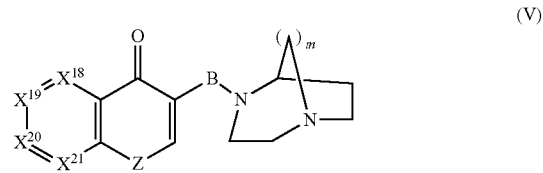

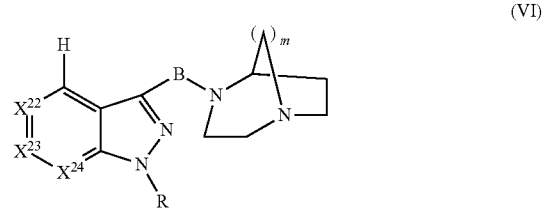

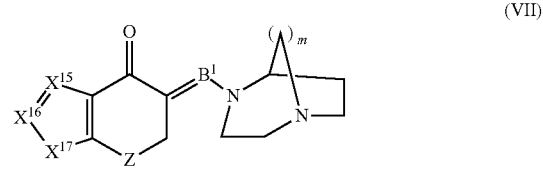

-continued

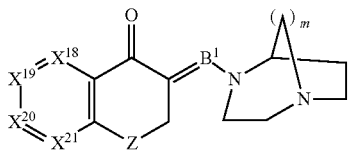

(VIII)

wherein
- $X^1$ is CH or $CR^1$;
- $X^2$ to $X^5$ are each, independently, N, CH, $CR^1$, or C—, wherein —C represents the point of attachment of group B, and wherein at most one of $X^2$ to $X^5$ is N, and one of $X^2$ to $X^5$ is —C (preferably $X^3$ or $X^4$), preferably $X^1$ is CH, or $CR^1$, $X^2$ and $X^5$ are N or CH, and $X^3$ and $X^4$ are N, CH, $CR^1$, or C—;
- $X^7$ to $X^{10}$ are each, independently, N, CH, or $CR^2$, wherein at most one of $X^7$ to $X^{10}$ is N;
- $X^{11}$ to $X^{14}$ are each, independently N, CH, $CR^3$, or C—, wherein —C represents the point of attachment of group B, and wherein at most one of $X^{11}$ to $X^{14}$ is N, and one of $X^{11}$ to $X^{14}$ is —C (preferably $X^{12}$ or $X^{13}$);
- $X^{15}$ to $X^{17}$ are each, independently N, O, S, CH, or $CR^4$;
- $X^{18}$ to $X^{21}$ are each, independently N, CH, or $CR^5$, wherein at most one of $X^{18}$ to $X^{21}$ is N;
- $X^{22}$ and $X^{23}$ are each, independently, CH or $CR^{12}$, wherein at least one of $X^{22}$ or $X^{23}$ is $CR^{12}$;
- $X^{24}$ is either CH or N;
- B is $CH_2$, C=O, or C=S;
- $B^1$ is CH;
- Y is O or S;
- Z is O or $NR^{11}$;
- m is 1 or 2;
- R is H, alkyl having 1 to 4 carbon atoms, halogenated alkyl having 1 to 4 carbon atoms, cycloalkyl having 3 to 7 carbon atoms, cycloalkylalkyl having 4 to 7 carbon atoms, or $C_{1-6}$alkyl-Ar (e.g., benzyl),
- $R^1$, $R^2$, $R^4$ and $R^5$ are each, independently,
  - $C_{1-6}$-alkyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof (e.g., $CH_3$, $C_2H_5$, $CF_3$),
  - $C_{2-6}$-alkenyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof (e.g., $C_2H_3$, $C_3H_5$),
  - $C_{2-6}$-alkynyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, $Si(R^8)_3$, Ar, Het, or combinations thereof (e.g., $C_2H$, $C_3H_3$),
  - $C_{3-8}$-cycloalkyl which is unsubstituted or substituted one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof (e.g., cyclopropyl, cyclobutyl, cyclopentyl),
  - $C_{4-10}$-cycloalkylalkyl which is unsubstituted or substituted in the cycloalkyl portion one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof, and/or substituted in the alkyl portion one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof (e.g., cyclopentylmethyl, cyclopropylmethyl, etc.),
  - halogen (e.g., F, Cl, Br, I,),
  - CN, $NO_2$, $NR^6R^7$, $SR^6$, $SOR^6$, $SO_2R^6$, $SO_2NR^6R^7$, $NR^6SO_2R^7$, $CONR^6R^7$, $CSNR^6R^7$, $COOR^6$, $NR^6COR^7$, $NR^6CSR^7$, $NR^6CONR^6R^7$, $NR^6CSNR^6R^7$, $NR^6COOR^7$, $NR^6CSOR^7$, $OCONR^6R^7$, $OCSNR^6R^7$,
  - Ar (e.g., phenyl),
  - Het (e.g., thienyl), or
  - $OR^9$ (e.g., hydroxyl, alkoxy, cycloalkyloxy, cycloalkylalkoxy);
- $R^3$ is halogen (e.g., F, Cl, Br, I), $OR^{16}$ (e.g., $OCH_3$, cyclopropyloxy, cyclopropylmethoxy, $OCF_3$, $OCHF_2$, hydroxyethoxy), CN, nitro, alkyl having 1 to 4 carbon atoms (e.g., $CH_3$, $C_2H_5$), halogenated alkyl having 1 to 4 carbon atoms (e.g., $CF_3$), cycloalkyl having 3 to 7 carbon atoms (e.g., cyclopropyl, cyclobutyl, cyclopentyl), cycloalkylalkyl having 4 to 7 carbon atoms (e.g., cyclopentylmethyl, cyclopropylmethyl), hydroxyalkyl having 1 to 4 carbon atoms (e.g., hydroxymethyl, hydroxyethyl), $NH_2$, monoalkylamino having 1 to 4 carbon atoms (e.g., methylamino), dialkylamino wherein each alkyl group independently has 1 to 4 carbon atoms (e.g., dimethylamino), Ar (e.g., phenyl) or Het;
- $R^6$ and $R^7$ are each independently
  - H,
  - $C_{1-6}$-alkyl which is unsubstituted or substituted one or more times by F, Cl, Br, I, CN, $OR^{16}$, monoalkylamino having 1 to 6 carbon atoms, dialkylamino wherein each alkyl group has 1 to 6 carbon atoms (e.g., diethylamino), $C_{3-8}$-cycloalkyl, Ar, Het, or combinations thereof (e.g., $CH_3$, $C_2H_5$, $CF_3$),
  - $C_{3-6}$-alkenyl which is unsubstituted or substituted one or more times by F, Cl, Br, I, CN, $OR^{16}$, monoalkylamino having 1 to 6 carbon atoms, dialkylamino wherein each alkyl group has 1 to 6 carbon atoms (e.g., diethylamino), $C_{3-8}$-cycloalkyl, Ar, Het, or combinations thereof (e.g., $C_2H_3$, $C_3H_5$),
  - $C_{3-6}$-alkynyl which is unsubstituted or substituted one or more times by F, Cl, Br, I, CN, $OR^{16}$, monoalkylamino having 1 to 6 carbon atoms, dialkylamino wherein each alkyl group has 1 to 6 carbon atoms (e.g., diethylamino), $C_{3-8}$-cycloalkyl, $Si(R^8)_3$, Ar, Het, or combinations thereof (e.g., $C_2H$, $C_3H_3$),
  - $C_{3-8}$-cycloalkyl which is unsubstituted or substituted one or more times by F, Cl, Br, I, CN, $OR^{16}$, monoalkylamino having 1 to 6 carbon atoms, dialkylamino wherein each alkyl group has 1 to 6 carbon atoms (e.g., diethylamino), $C_{3-8}$-cycloalkyl, Ar, Het, or combinations thereof (e.g., cyclopropyl, cyclobutyl, cyclopentyl),
  - $C_{4-10}$-cycloalkylalkyl which is unsubstituted or substituted in the cycloalkyl portion one or more times by F, Cl, Br, I, CN, $OR^{16}$ monoalkylamino having 1 to 6 carbon atoms, dialkylamino wherein each alkyl group has 1 to 6 carbon atoms (e.g., diethylamino), $C_{3-8}$-cycloalkyl, Ar, Het, or combinations thereof, and/or substituted in the alkyl portion one or more times by F, Cl, Br, I, CN, $OR^{16}$, monoalkylamino having 1 to 6 carbon atoms, dialkylamino wherein each alkyl group has 1 to 6 carbon atoms (e.g., diethylamino), $C_{3-8}$-cycloalkyl, Ar, Het, or combinations thereof (e.g., cyclopentylmethyl, cyclopropylmethyl, etc.),
  - Ar, or
  - Het;
- $R^8$ is $C_{1-6}$-alkyl (e.g., $CH_3$);
- $R^9$ is H, $C_{1-6}$-alkyl which is unsubstituted or substituted one or more by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof (e.g., $CH_3$, $C_2H_5$, $CF_3$), $C_{3-6}$-alkenyl which is unsubstituted or substituted one or more by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof (e.g., $C_2H_3$, $C_3H_5$), $C_{3-6}$-alkynyl which is unsubstituted or substituted one or more by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof (e.g., $C_2H$, $C_3H_3$), $C_{3-8}$-cycloalkyl which is unsubstituted or substituted one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof (e.g., cyclopropyl, cyclobutyl, cyclopentyl), $C_{4-8}$-cycloalkylalkyl which is unsubstituted or substituted one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof (e.g., cyclopentylmethyl, cyclopropylmethyl, etc.), Ar, or Het;

$R^{10}$ is H, alkyl having 1 to 4 carbon atoms (e.g., $CH_3$, $C_2H_5$), halogenated alkyl having 1 to 4 carbon atoms (e.g., $CF_3$), cycloalkyl having 3 to 7 carbon atoms (e.g., cyclopropyl, cyclobutyl, cyclopentyl), or cycloalkylalkyl having 4 to 7 carbon atoms (e.g., cyclopentylmethyl, cyclopropylmethyl, etc.);

$R^{11}$ is H, alkyl having 1 to 4 carbon atoms (which is unsubstituted or substituted one or more times by halogen, $OR^{16}$, $C_{3-8}$ cycloalkyl, $NR^6R^7$, Ar, or Het), cycloalkyl having 3 to 7 carbon atoms (which is unsubstituted or substituted one or more times by halogen, $OR^{16}$, $NR^6R^7$, Ar, or Het), cycloalkylalkyl having 4 to 7 carbon atoms (e.g., cyclopentylmethyl, cyclopropylmethyl, etc.), Ar or Het (e.g., $CH_3$, $C_2H_5$, $CF_3$, cyclopropyl, cyclopentyl, phenyl);

$R^{12}$ is halogen (e.g., F), $C_{1-6}$-alkoxy which is substituted one or more times by F, —NHCONH—$C_{1-4}$-alkyl, Ar, Ar—$C_{1-4}$-alkyl-O—, or is selected from Formulae IX-XI

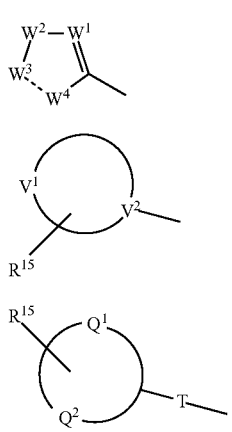

(IX)

(X)

(XI)

wherein Formula IX represents a 5-membered, unsaturated heterocycle in which the bond between $W^2$ and $W^3$ is a single bond and the bond between $W^3$ and $W^4$ is a double bond, or the bond between $W^2$ and $W^3$ is a double bond and the bond between $W^3$ and $W^4$ is a single bond, Formula X represents a 5-8-membered, heterocycle which is saturated or partially saturated and wherein the heterocyclic ring may be bridged by a divalent alkylene group having 1 to 3 carbon atoms and may be optionally substituted by oxo, and Formula XI represents a 5-8-membered, heterocycle which is saturated, partially saturated, or unsaturated and wherein the heterocyclic ring may be bridged by a divalent alkylene group having 1 to 3 carbon atoms;

$Q^1$ is O, S, N, $NR^{13}$, or $SO_2$;

$Q^2$ is CH, $CR^{14}$, $CHR^{14}$, O, S, $SO_2$, N, or $NR^{13}$;

T is O or $NR^{10}$;

$V^1$ is O, S, $SO_2$, N, $NR^{13}$, $CR^{14}$, or $CHR^{14}$;

$W^1$ is N;

$W^2$ and $W^3$ are each, independently, O, S, N, $NR^{13}$, CH, or $CR^1$, in which the bond between $W^2$ and $W^3$ is a single bond and the bond between $W^3$ and $W^4$ is a double bond, or the bond between $W^2$ and $W^3$ is a double bond and the bond between $W^3$ and $W^4$ is a single bond;

$W^4$ is O, S, N, or $NR^{13}$;

$V^2$ is C, CH, C—OH, or N;

$R^{13}$ is H, $C_{1-6}$-alkyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof (e.g., $CH_3$, $C_2H_5$, $CF_3$), $C_{3-6}$-alkenyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof (e.g., $C_2H_3$, $C_3H_5$), $C_{3-6}$-alkynyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, $Si(R^8)_3$, Ar, Het, or combinations thereof (e.g., $C_2H$, $C_3H_3$), $C_{3-8}$-cycloalkyl which is unsubstituted or substituted one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof (e.g., cyclopropyl, cyclobutyl, cyclopentyl), $C_{4-10}$-cycloalkylalkyl which is unsubstituted or substituted in the cycloalkyl portion one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof, and/or substituted in the alkyl portion one or more times by F, Cl, Br, I, CN, $OR^{16}$, $NR^6R^7$, SH, $SR^6$, $SOR^6$, $C_{3-8}$-cycloalkyl (e.g., cyclopentylmethyl, cyclopropylmethyl, etc.), $SO_2R^6$, $SO_2NR^6R^7$, Ar, Het, or combinations thereof (e.g., cyclopentylmethyl, cyclopropylmethyl, etc.), $SO_2R^6$, $CONR^6R^7$, $CSNR^6R^7$, $COOR^6$, $CSOR^6$, $COR^7$, $CSR^7$, Ar, or Het;

$R^{14}$ is H, $C_{1-6}$-alkyl which is unsubstituted or substituted one or more times by F, Cl, Br, I, CN, $OR^9$, $NR^6R^7$, SH, $SR^6$, $SOR^6$, $C_{3-8}$-cycloalkyl, $SO_2R^6$, $SO_2NR^6R^7$, Ar, Het, or combinations thereof (e.g., $CH_3$, $C_2H_5$, $CF_3$), $C_{2-6}$-alkenyl which is unsubstituted or substituted one or more times by F, Cl, Br, I, CN, $OR^9$, $NR^6R^7$, SH, $SR^6$, $SOR^6$, $C_{3-8}$-cycloalkyl, $SO_2R^6$, $SO_2NR^6R^7$, Ar, Het, or combinations thereof (e.g., $C_2H_3$, $C_3H_5$), $C_{2-6}$-alkynyl which is unsubstituted or substituted one or more times by F, Cl, Br, I, CN, $OR^9$, $NR^6R^7$, SH, $SR^6$, SOR⁶, $C_{3-8}$-cycloalkyl, SO₂R⁶, SO₂NR⁶R⁷, Si(R⁸)₃, Ar, Het, or combinations thereof (e.g., C₂H, C₃H₃), $C_{3-8}$-cycloalkyl which is unsubstituted or substituted one or more times by F, Cl, Br, I, CN, OR⁹, NR⁶R⁷, SH, SR⁶, SOR⁶, unsubstituted $C_{3-8}$-cycloalkyl, SO₂R⁶, SO₂NR⁶R⁷, Ar, Het, or combinations thereof (e.g., cyclopropyl, cyclobutyl, cyclopentyl), $C_{4-10}$-cycloalkylalkyl which is unsubstituted or substituted in the cycloalkyl portion one or more times by F, Cl, Br, I, CN, OR⁹, NR⁶R⁷, SH, SR⁶, SOR⁶, unsubstituted $C_{3-8}$-cycloalkyl, SO₂R⁶, SO₂NR⁶R⁷, Ar, Het, or combinations thereof, and/or substituted in the alkyl portion one or more times by F, Cl, Br, I, CN, OR¹⁶, NR⁶R⁷, SH, SR⁶, SOR⁶, $C_{3-8}$-cycloalkyl, SO₂R⁶, SO₂NR⁶R⁷, Ar, Het, or combinations thereof (e.g., cyclopentylmethyl, cyclopropylmethyl, etc.), halogen (e.g., F, Cl, Br, I,), CN, NO₂, NR⁶R⁷, SR⁶, SOR⁶, SO₂R⁶, SO₂NR⁶R⁷, NR⁶SO₂R⁷, CONR⁶R⁷, CSNR⁶R⁷, COOR⁶, NR⁶COR⁷, NR⁶CSR⁷, NR⁶CONR⁶R⁷, NR⁶CSNR⁶R⁷, NR⁶COOR⁷, NR⁶CSOR⁷, OCONR⁶R⁷, OCSNR⁶R⁷, Ar, Het, or

OR⁹;

R¹⁵ is H, $C_{1-6}$-alkyl which is unsubstituted or substituted one or more times by F, Cl, Br, I, CN, OR¹⁶, NR⁶R⁷, SH, SR⁶, SOR⁶, $C_{3-8}$-cycloalkyl, SO₂R⁶, SO₂NR⁶R⁷, Ar, Het, or combinations thereof (e.g., CH₃, C₂H₅, CF₃), $C_{2-6}$-alkenyl which is unsubstituted or substituted one or more times by F, Cl, Br, I, CN, OR¹⁶, NR⁶R⁷, SH, SR⁶, SOR⁶, $C_{3-8}$-cycloalkyl, SO₂R⁶, SO₂NR⁶R⁷, Ar, Het, or combinations thereof (e.g., C₂H₃, C₃H₅), $C_{2-6}$-alkynyl which is unsubstituted or substituted one or more times by F, Cl, Br, I, CN, OR¹⁶, NR⁶R⁷, SH, SR⁶, SOR⁶, $C_{3-8}$-cycloalkyl, SO₂R⁶, SO₂NR⁶R⁷, Si(R⁸)₃, Ar, Het, or combinations thereof (e.g., C₂H, C₃H₃), $C_{3-8}$-cycloalkyl which is unsubstituted or substituted one or more times by F, Cl, Br, I, CN, OR¹⁶, NR⁶R⁷, SH, SR⁶, SOR⁶, unsubstituted $C_{3-8}$-cycloalkyl, SO₂R⁶, SO₂NR⁶R⁷, Ar, Het, or combinations thereof (e.g., cyclopropyl, cyclobutyl, cyclopentyl), $C_{4-10}$-cycloalkylalkyl which is unsubstituted or substituted in the cycloalkyl portion one or more times by F, Cl, Br, I, CN, OR¹⁶, NR⁶R⁷, SH, SR⁶, SOR⁶, unsubstituted $C_{3-8}$-cycloalkyl, SO₂R⁶, SO₂NR⁶R⁷, Ar, Het, or combinations thereof, and/or substituted in the alkyl portion one or more times by F, Cl, Br, I, CN, OR¹⁶, NR⁶R⁷, SH, SR⁶, SOR⁶, $C_{3-8}$-cycloalkyl, SO₂R⁶, SO₂NR⁶R⁷, Ar, Het, or combinations thereof (e.g., cyclopentylmethyl, cyclopropylmethyl, etc.), $C_{3-8}$-cycloalkyloxy which is unsubstituted or substituted one or more times by F, Cl, Br, I, CN, OR¹⁶, NR⁶R⁷, SH, SR⁶, SOR⁶, unsubstituted $C_{3-8}$-cycloalkyl, SO₂R⁶, SO₂NR⁶R⁷, Ar, Het, or combinations thereof (e.g., cyclopropyloxy, cyclopentyloxy), halogen (e.g., F, Cl, Br, I,), oxo, thio, CN, NO₂, NR⁶R⁷, SR⁶, SOR⁶, SO₂R⁶, SO₂NR⁶R⁷, NR⁶SO₂R⁷, CONR⁶R⁷, CSNR⁶R⁷, COOR⁶, NR⁶COR⁷, NR⁶CSR⁷, NR⁶CONR⁶R⁷, NR⁶CSNR⁶R⁷, NR⁶COOR⁷, NR⁶CSOR⁷, OCONR⁶R⁷, OCSNR⁶R⁷, Ar, Het, or

OR⁹;

R¹⁶ is H, $C_{1-6}$-alkyl which is unsubstituted or substituted one or more by F, Cl, Br, I, CN, OH, alkoxy having 1 to 4 carbon atoms, NR⁶R⁷, SH, SR⁶, SOR⁶, $C_{3-8}$-cycloalkyl, SO₂R⁶, SO₂NR⁶R⁷, Ar, Het, or combinations thereof (e.g., CH₃, C₂H₅, CF₃), $C_{3-8}$-cycloalkyl which is unsubstituted or substituted one or more times by F, Cl, Br, I, CN, OH, alkoxy having 1 to 4 carbon atoms, NR⁶R⁷, SH, SR⁶, SOR⁶, unsubstituted $C_{3-8}$-cycloalkyl, SO₂R⁶, SO₂NR⁶R⁷, Ar, Het, or combinations thereof (e.g., cyclopropyl, cyclobutyl, cyclopentyl), or $C_{4-8}$-cycloalkylalkyl which is unsubstituted or substituted one or more times by F, Cl, Br, I, CN, OH, alkoxy having 1 to 4 carbon atoms, NR⁶R⁷, SH, SR⁶, SOR⁶, unsubstituted $C_{3-8}$-cycloalkyl, SO₂R⁶, SO₂NR⁶R⁷, Ar, Het, or combinations thereof (e.g., cyclopentylmethyl, cyclopropylmethyl, etc.);

R¹⁷ and R¹⁸ are each independently H, alkyl having 1 to 4 carbon atoms (e.g., CH₃, C₂H₅), halogenated alkyl having 1 to 4 carbon atoms (e.g., CF₃), cycloalkyl having 3 to 7 carbon atoms (e.g., cyclopropyl, cyclobutyl, cyclopentyl), or cycloalkylalkyl having 4 to 7 carbon atoms (e.g., cyclopentylmethyl, cyclopropylmethyl, etc.);

R¹⁹ is H or CONH—CH₂—Ar;

Ar is an aryl group containing 6 to 10 carbon atoms which is unsubstituted or substituted one or more times by alkyl having 1 to 8 carbon atoms, alkoxy having 1 to 8 carbon atoms, halogen (F, Cl, Br, or I, preferably F or Cl), amino, cyano, hydroxyl, nitro, halogenated alkyl having 1 to 8 carbon atoms, halogenated alkoxy having 1 to 8 carbon atoms, hydroxyalkyl having 1 to 8 carbon atoms, hydroxyalkoxy having 2 to 8 carbon atoms, alkenyloxy having 3 to 8 carbon atoms, monoalkylamino having 1 to 8 carbon atoms, dialkylamino wherein the alkyl portions each have 1 to 8 carbon atoms, carboxy, alkoxycarbonyl, alkylaminocarbonyl, acylamido (e.g., acetamido), acyloxy (e.g., acetoxy), alkylthio having 1 to 8 carbon atoms, alkylsulphinyl having 1 to 8 carbon atoms, alkylsulphonyl having 1 to 8 carbon atoms, sulfo, sulfonylamino, Het, cycloalkylamino wherein the cycloalkyl group has 3 to 7 C atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, COR⁹, CSR⁹, cyano, hydroxyl, nitro, oxo, or thio, aryloxy wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, arylthio wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, cycloalkyloxy wherein the cycloalkyl group has 3 to 7 C atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, or combinations thereof; and Het is a heterocyclic group (e.g., furyl, thienyl, methylthienyl, bithienyl, benzylprazolyl, thiazolyl, imidazolyl, methylimidazolyl, pyrrolidinyl, morpholinyl, thiomorpholinyl, diazabicyclooctyl, diazabicycloheptyl, diazabicyclononyl), which is fully saturated, partially saturated or fully unsaturated, having 5 to 10 ring atoms in which at least 1 ring atom is a N, O or S atom, which is unsubstituted or substituted one or more times by
alkyl having 1 to 8 carbon atoms,
alkoxy having 1 to 8 carbon atoms,
cycloalkyl having 3 to 8 carbon atoms,
cycloalkylalkyl having 4 to 8 carbon atoms,
halogen (F, Cl, Br, or I, preferably F or Cl),
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
carboxy,
alkoxycarbonyl,
alkylaminocarbonyl,
acylamido (e.g., acetamido),
acyloxy (e.g., acetoxy),
alkylthio having 1 to 8 carbon atoms,
alkylsulphinyl having 1 to 8 carbon atoms,
alkylsulphonyl having 1 to 8 carbon atoms,
sulfo,
oxo,
sulfonylamino,
cycloalkylamino wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, aryl containing 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, aryl-alkylene group (e.g., benzyl, phenethyl, phenpropyl) wherein the aryl portion contains 6 to 10 carbon atoms and the alkylene portion contains 1 to 4 carbon atoms and is unsubstituted or substituted one or more times by halogen (F, Cl, Br, or I, preferably F or Cl), alkyl having 1 to 8 C atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, aryloxy wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, arylthio wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, cycloalkyloxy wherein the cycloalkyl group has 3 to 7 carbon atoms and is optionally substituted by halogen (F, Cl, Br, or I, preferably F or Cl), alkyl having 1 to 8 C carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, COR$^9$, CSR$^9$, cyano, hydroxyl, nitro, oxo, or thio, or combinations thereof; and and pharmaceutically acceptable salts or solvates (e.g., hydrates), or solvates of pharmaceutically acceptable salts thereof, with the proviso that when R$^{12}$ is halogen, X$^{24}$ is N.

See also U.S. application Ser. No. 11/123,219, filed May 6, 2005, WO 2004, 033456, and WO 2005/077955.

According to a further aspect of the invention, the compounds are selected from Formulas I-VIII wherein said compounds have at least one Het group substituted by cycloalkyl or cycloalkylalkyl.

According to a further aspect of the invention, the compounds are selected from Formula VI and have at least one R$^{12}$ group which is halogen, —NHCONH—C$_{1-4}$-alkyl, Ar, or Ar—C$_{1-4}$-alkyl-O—.

According to a further aspect of the invention, the compounds are selected from Formula II or Formula VI:

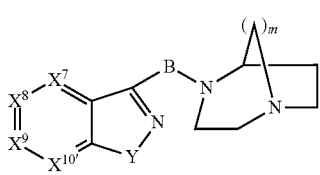

(II)

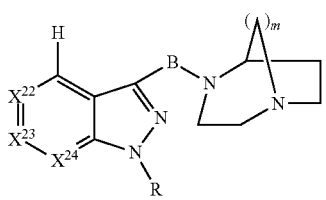

(VI)

wherein

B, R, X$^{22}$, X$^{23}$, and X$^{24}$ are as previously defined, m is 2;

Y is S;

X$^7$, X$^8$, X$^9$ and X$^{10}$ are each, independently, N, CH, or CR$^2$, wherein at most one of X$^7$, X$^8$, X$^9$ and X$^{10}$ is N;

at least one of X$^8$ or X$^9$ is CR$^2$ in which R$^2$ is Het other than imidazolidinyl or R$^2$ is OR$^9$ in which R$^9$ is Het;

at least one of X$^{22}$ and X$^{23}$ is CR$^{12}$ in which R$^{12}$ is halogen, —NHCO—NH—C$_{1-4}$-alkyl or is selected from Formulae IX-XI

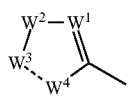

(IX)

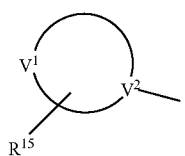

(X)

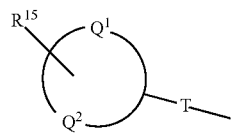

(XI)

Q$^1$, Q$^2$, T, V$^1$, W$^1$, W$^2$, W$^3$, and R$^{15}$ are as previously defined, W$^4$ is N or NR$^{13}$, V$^2$ is N, and R$^{13}$ is as previously defined.

According to a further aspect of the invention, the compounds are selected from Formula VI:

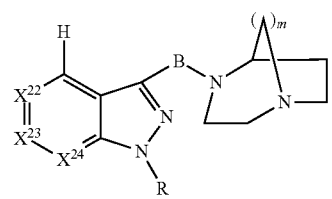

(VI)

wherein

B, R, X$^{22}$, X$^{23}$, and m are as previously defined, and X$^{24}$ is N.

According to a further aspect of the invention, the compounds are selected from Formula VI:

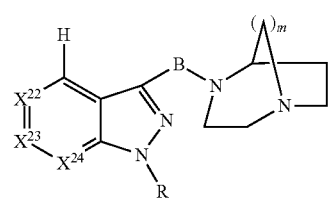

(VI)

wherein

B, R, X$^{22}$, and m are as previously defined, and

X$^{24}$ is N,

X$^{23}$ is CR$^{20}$, and

R$^{20}$ is halogen.

According to a further aspect of the invention, the compounds are selected from Formula VI:

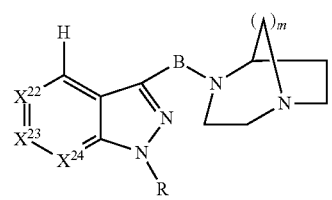

(VI)

wherein

B, and R are as previously defined, m is 2;

X$^{24}$ is CH, at least one of X$^{22}$ and X$^{23}$ is CR$^{21}$ in which R$^{21}$ is selected from Formulae IX-XI

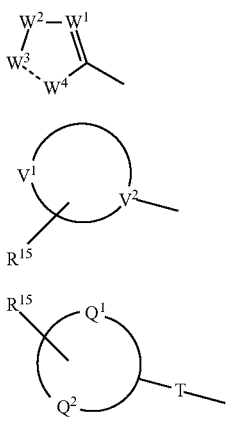

$Q^1$, $Q^2$, T, $V^1$, $W^1$, $W^2$, $W^3$, and $R^{15}$ are as previously defined,
$W^4$ is N or $NR^{13}$,
$V^2$ is N, and
$R^{13}$ is as previously defined.

According to a further aspect of the invention, the compounds are selected from Formula VI:

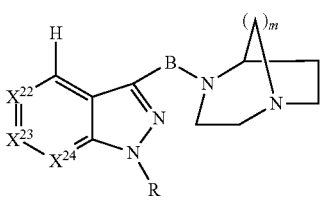

wherein
B, R and $X^{22}$ are as previously defined,
m is 2;
$X^{24}$ is CH,
$X^{23}$ is $CR^{21}$, and
$R^{21}$ is selected from Formulae IX-XI

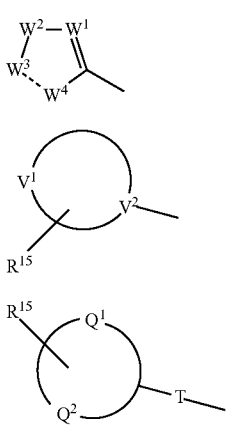

$Q^1$, $Q^2$, T, $V^1$, $W^1$, $W^2$, $W^3$, and $R^{15}$ are as previously defined,
$W^4$ is N or $NR^{13}$,
$V^2$ is N, and
$R^{13}$ is as previously defined.

According to a further aspect of the invention, the compounds are selected from Formula VI:

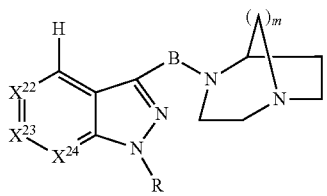

wherein
B, R and $X^{22}$ are as previously defined,
m is 2;
$X^{24}$ is CH,
$X^{23}$ is $CR^{21}$, and
$R^{21}$ is of Formula IX

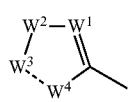

$W^1$, $W^2$, and $W^3$ are as previously defined,
$W^4$ is N or $NR^{13}$, and
$R^{13}$ is as previously defined.

According to a further aspect of the invention, the compounds are selected from Formula VI:

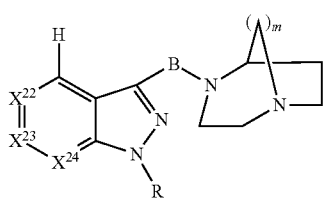

wherein
B, R, $X^{22}$, and m are as previously defined, and
$X^{24}$ is CH,
$X^{23}$ is $CR^{21}$, and
$R^{21}$ is of Formula X

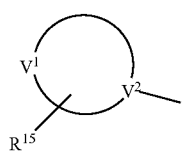

$V^1$ is as previously defined,
$V^2$ is N, and
$R^{15}$ is as previously defined.

According to a further aspect of the invention, the compounds are selected from Formula VI:

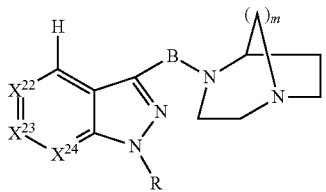

(VI)

wherein
B, R, and m are as previously defined, and
$X^{24}$ is CH,
at least one of $X^{22}$ and $X^{23}$ is $CR^{21}$ in which $R^{21}$ is of Formula XI

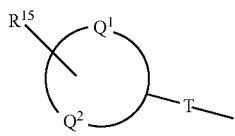

(XI)

$Q^1$, $Q^2$, T, and $R^{15}$ are as previously defined.

According to a further aspect of the invention, the compounds are selected from Formula VI:

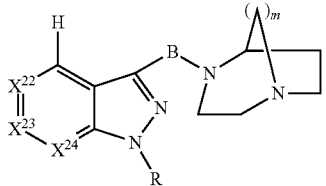

(VI)

wherein
B and R are as previously defined,
m is 2;
$X^{24}$ is CH,
$X^{23}$ is $CR^{21}$, and
$R^{21}$ is selected from Formulae IX-XI

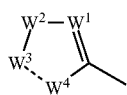

(IX)

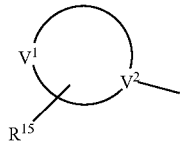

(X)

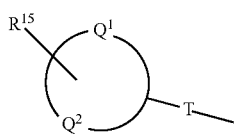

(XI)

$Q^1$, $Q^2$, T, $V^1$, $W^1$, $W^2$, $W^3$, and $R^{15}$ are as previously defined, $W^4$ is N or $NR^{13}$,
$V^2$ is N, and
$R^{13}$ is as previously defined.

According to a further aspect of the invention, the compounds are selected from Formula VI:

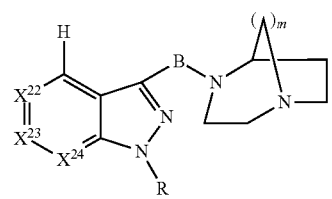

(VI)

wherein
B, R and m are as previously defined,
$X^{24}$ is CH,
at least one of $X^{22}$ and $X^{23}$ is $CR^{12}$ in which $R^{12}$ is —NHCO—NH—$C_{1-4}$-alkyl or substituted or unsubstituted pyrrolidinyl, morpholinyl, thiomorpholinyl, piperazinyl, diazepanyl, oxazepanyl, tetrahydropyranyloxy, dihydroimidazolyl, or imidazolidinyl (e.g., 3-propylimidazolidin-2-one).

According to a further aspect of the invention, the compounds are selected from Formula VI:

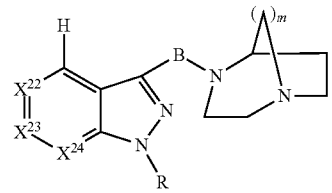

(VI)

wherein
B, R and m are as previously defined,
$X^{24}$ is CH,
at least one of $X^{22}$ and $X^{23}$ is $CR^{12}$, and
$R^{12}$ is pyrrolidinyl which is substituted by alkoxy having 1 to 6 carbon atoms, amino, mononalkylamino having 1 to 6 carbon atoms, or dialkylamino wherein each alkyl group has 1 to 6 carbon atoms.

According to a further aspect of the invention, the compounds are selected from Formula II:

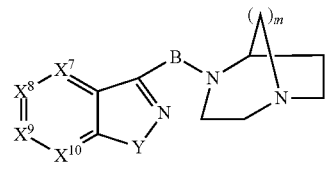

(II)

wherein
Y is S,
$X^7$, $X^9$ and $X^{10}$ are each, independently, N, CH, or $CR^2$, wherein at most one of $X^7$, $X^9$ and $X^{10}$ is N, and
$X^8$ is $CR^2$.

According to a further aspect of the invention, the compounds are selected from Formula II:

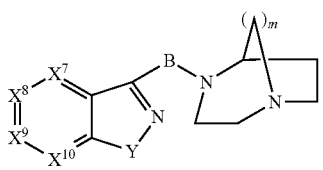

(II)

wherein
Y is S,
$X^7$, $X^9$ and $X^{10}$ are each, independently, N, CH, or $CR^2$, wherein at most one of $X^7$, $X^9$ and $X^{10}$ is N, and
$X^8$ is $COR^9$.

According to a further aspect of the invention, the compounds are selected from Formula II:

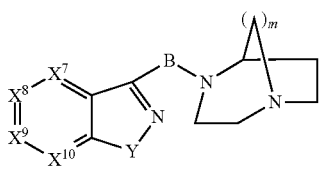

(II)

wherein
Y is S,
$X^7$, $X^8$, $X^9$ and $X^{10}$ are each, independently, N, CH, or $CR^2$, wherein at most one of $X^7$, $X^8$, $X^9$ and $X^{10}$ is N, and
at least one of $X^8$ or $X^9$ is $CR^2$ in which $R^2$ is Het other than imidazolidinyl or $R^2$ is $OR^9$ and $R^9$ is Het.

According to a further aspect of the invention, the compounds are selected from Formula II:

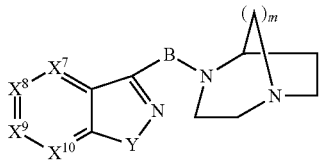

(II)

wherein
Y is S,
$X^7$, $X^8$, $X^9$ and $X^{10}$ are each, independently, N, CH, or $CR^2$, wherein at most one of $X^7$, $X^8$, $X^9$ and $X^{10}$ is N, and
at least one of $X^8$ or $X^9$ is $CR^2$ in which $R^2$ is substituted or unsubstituted pyrrolidinyl, diazabicycloheptyl, diazabicyclononyl, piperazinyl, diazepanyl, hexahydropyrrolopyrazinyl, diazabicyclooctyl, pyrrolidinyloxy, or azabicyclooctyloxy.

Alkyl throughout means a straight-chain or branched-chain aliphatic hydrocarbon radical having preferably 1 to 4 carbon atoms, unless otherwise indicated. Suitable alkyl groups include methyl, ethyl, propyl, isopropyl, butyl, sec-butyl, and tert-butyl. The alkyl group can also be substituted.

Alkenyl throughout means a straight-chain or branched-chain alkyl radical having preferably 2 to 6 carbon atoms, unless otherwise indicated, wherein at least one $CH_2CH_2$ group is replaced by CH=CH. Suitable alkenyl groups include ethenyl, propenyl, butenyl, etc. The alkenyl group can also be substituted.

Alkynyl throughout means a straight-chain or branched-chain alkyl radical having preferably 2 to 6 carbon atoms, unless otherwise indicated, wherein at least one $CH_2CH_2$ group is replaced by C≡C. Suitable alkynyl groups include ethynyl, propynyl, butynyl, etc. The alkynyl group can also be substituted.

Alkoxy means alkyl-O— groups in which the alkyl portion preferably has 1 to 4 carbon atoms, unless otherwise indicated. Suitable alkoxy groups include methoxy, ethoxy, propoxy, isopropoxy, isobutoxy, and sec-butoxy. The alkoxy group can also be substituted. For example, the alkoxy group may be substituted one or more times by F (e.g., OCF3, and $OCHF_2$).

Cycloalkyl means a cyclic, bicyclic or tricyclic saturated hydrocarbon radical having 3 to 8 carbon atoms, unless otherwise indicated. Suitable cycloalkyl groups include cyclopropyl, cyclobutyl, cyclopentyl, and cyclohexyl. Other suitable cycloalkyl groups include spiropentyl, bicyclo[2.2.1]heptyl, and bicyclo[2.2.2]octyl.

The cycloalkyl groups can be substituted by, for example, F, Cl, Br, $C_{1-4}$-alkyl, $C_{1-4}$-alkoxy, hydroxyl, amino, monoalkylamino having 1 to 4 carbon atoms, and/or dialkylamino in which each alkyl group has 1 to 4 carbon atoms.

Cycloalkylalkyl refers to cycloalkyl-alkyl radicals in which the cycloalkyl and alkyl portions are in accordance with previous discussions. Suitable examples include cyclopropylmethyl and cyclopentylmethyl.

Cycloalkyloxy refers to cycloalkyl-oxy radicals in which the cycloalkyl portion is in accordance with previous discussions. Suitable examples include cyclopropyloxy and cyclopentyloxy.

Aryl, as a group or substituent per se or as part of a group or substituent, refers to an aromatic carbocyclic radical containing 6 to 10 carbon atoms, unless indicated otherwise. Suitable aryl groups include phenyl, naphthyl and biphenyl. Substituted aryl groups include the above-described aryl groups which are substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy).

Arylalkyl refers to an aryl-alkyl radical in which the aryl and alkyl portions are in accordance with the previous descriptions. Suitable examples include benzyl, 1-phenethyl, 2-phenethyl, phenpropyl, phenbutyl, phenpentyl, and naphthylmethyl.

Heterocyclic groups refer to saturated, partially saturated and fully unsaturated heterocyclic groups having one, two or three rings and a total number of 5 to 10 ring atoms wherein at least one of the ring atoms is an N, O or S atom. Preferably, the heterocyclic group contains 1 to 3 hetero-ring atoms selected from N, O and S. Suitable saturated and partially saturated heterocyclic groups include, but are not limited to tetrahydrofuranyl, tetrahydrothienyl, tetrahydropyranyl, dihydropyranyl, pyrrolidinyl, piperidinyl, piperazinyl, morpholinyl, oxoazolinyl, isoxazolinyl and the like. Suitable heteroaryl groups include but are not limited to furyl, thienyl, pyrrolyl, pyrazolyl, imidazolyl, pyridyl, pyrimidinyl, benzopyranyl, indolyl, quinolinyl, isoquinolinyl, naphthyridinyl and the like. Other examples of suitable heterocyclic groups, are 2-quinolinyl, 1,3-benzodioxyl, 2-thienyl, 2-benzofuranyl, 2-benzothiophenyl, 3-thienyl, 2,3-dihydro-5-benzofuranyl, 4-indolyl, 4-pyridyl, 3-quinolinyl, 4-quinolinyl, 1,4-benzodioxan-6-yl, 3-indolyl, 2-pyrrolyl, benzopyran-6-yl, 5-indolyl, 1,5-benzoxepin-8-yl, 3-pyridyl, 6-coumarinyl, 5-benzofuranyl, 2-isoimidazol-4-yl, 3-pyrazolyl, 3-carbazolyl, 2-thiazolyl, 2-oxazolyl, 1-imidazolyl, and 2-imidazolyl.

Substituted heterocyclic groups refer to the heterocyclic groups described above, which are substituted in one or more places by, for example, halogen, aryl, alkyl, hydroxy, alkoxy, cyano, trifluoromethyl, nitro, oxo, amino, alkylamino, and dialkylamino.

Radicals which are substituted one or more times preferably have 1 to 3 substituents, especially 1 or 2 substituents of the exemplified substituents. Halogenated radicals such as halogenated alkyls are preferably fluorinated and include perhalo radicals such as trifluoromethyl.

In accordance with a further aspect of the invention, preferred R groups include halogens ($R^1$ to $R^5$, $R^{14}$ and $R^{15}$), nitro ($R^1$ to $R^5$, $R^{14}$ and $R^{15}$), $NR^6R^7$ ($R^1$, $R^2$, $R^4$, $R^5$, $R^{14}$ and $R^{15}$), amino ($R^1$ to $R^5$, $R^{14}$ and $R^{15}$), alkylamino ($R^1$ to $R^5$, $R^{14}$ and $R^{15}$), dialkylamino ($R^1$ to $R^5$, $R^{14}$ and $R^{15}$), phenyl which is unsubstituted or substituted ($R^1$, $R^2$, $R^4$ to $R^7$, $R^9$, $R^{11}$, and $R^{13}$ to $R^{15}$), $NR^6CONR^6R^7$ such as phenylurea ($R^1$, $R^2$, $R^4$, $R^5$, $R^{14}$ and $R^{15}$), hydroxyl ($R^1$ to $R^5$, $R^{14}$ and $R^{15}$), alkoxy ($R^1$ to $R^5$, $R^{14}$ and $R^{15}$), halogenated alkoxy ($R^1$ to $R^5$, $R^{14}$ and $R^{15}$), and alkylsuflonamide ($R^1$, $R^2$, $R^4$, $R^5$, $R^{14}$ and $R^{15}$) (e.g., bromo, nitro, amino, phenylurea, trifluoromethoxy, methoxy, methansulfonamide, hydroxyl, etc.)

In accordance with a further aspect of the invention, preferred groups for the heterocyclic groups of Formulas IX to XI include substituted or unsubstituted pyrrolidinyl (e.g., pyrrolidin-1-yl), morpholinyl (e.g., morpholin-4-yl), thiomorpholinyl (e.g., thiomorpholin-4-yl), imidazolidinyl (e.g., 3-propyl-imidazolidin-2-one), dihydroimidazolyl, piperazinyl (e.g., 4-methylpiperazin-1-yl), diazepanyl (e.g., 4-methyl-1,4-diazepan-1-yl), oxazepanyl (e.g., 1,4-oxazepan-1-yl).

In accordance with a further aspect of the invention, R in Formulas I and VI is preferably H or alkyl having 1 to 4 carbon atoms (e.g., methyl or ethyl), especially H.

In accordance with a further aspect of the invention, B in Formulas II and VI is preferably C=O. In Formula V, B is preferably $CH_2$ or C=O.

In accordance with a further aspect of the invention, Y in Formula II is preferably S.

In accordance with a further aspect of the invention, the subscript "m" is preferably 2.

In accordance with a further aspect of the invention, preferred $R^{12}$ groups of Formula X are substituted or unsubstituted pyrrolidinyl (e.g., pyrrolidin-1-yl), morpholinyl (e.g., morpholin-4-yl), thiomorpholinyl (e.g., thiomorpholin-4-yl), imidazolidinyl (e.g., 3-propyl-imidazolidin-2-one), dihydroimidazolyl, piperazinyl (e.g., 4-methylpiperazin-1-yl), diazepanyl (e.g., 4-methyl-1,4-diazepan-1-yl), and oxazepanyl (e.g., 1,4-oxazepan-1-yl).

In accordance with a further aspect of the invention, preferred $R^2$ groups are $OCH_3$, $OCF_3$, ethoxy, cyclopropylmethoxy, and cyclopropyl.

In accordance with a further aspect of the invention, $R^5$ is preferably $OCH_3$.

In accordance with a further aspect of the invention, the compounds of Formulas II and VI are preferred, particularly Formula IV.

According to a further compound and/or method aspect of the invention, preferred compounds are described by the following subformulas IIa-IIj and VIa-VIq, which correspond to formulas II and VI, but exhibit the following preferred groups:

IIa B is CO,
    Y is S,
    $X^7$, $X^9$ and $X^{10}$ are each, independently, N, CH, or $CR^2$, wherein at most one of $X^7$, $X^9$ and $X^{10}$ is N, and
    $X^8$ is $CR^2$.

IIb B is CO,
    Y is S,
    m is 2,
    $X^7$, $X^9$ and $X^{10}$ are each, independently, N, CH, or $CR^2$, wherein at most one of $X^7$, $X^9$ and $X^{10}$ is N, and
    $X^8$ is $CR^2$.

IIc B is CO,
    Y is S,
    $X^7$, $X^9$ and $X^{10}$ are each, independently, N, CH, or $CR^2$, wherein at most one of $X^7$, $X^9$ and $X^{10}$ is N, and
    $X^8$ is $COR^9$.

IId B is CO,
    Y is S,
    m is 2,
    $X^7$, $X^9$ and $X^{10}$ are each, independently, N, CH, or $CR^2$, wherein at most one of $X^7$, $X^9$ and $X^{10}$ is N, and
    $X^8$ is $COR^9$.

IIe B is CO,
    Y is S,
    $X^7$, $X^9$ and $X^{10}$ are each, independently, CH or $CR^2$, and
    $X^8$ is $CR^2$.

IIf B is CO,
    Y is S,
    $X^7$, $X^9$ and $X^{10}$ are each, independently, CH or $CR^2$, and
    $X^8$ is $COR^9$.

IIg B is CO,
    Y is S,
    m is 2,
    $X^7$, $X^9$ and $X^{10}$ are each, independently, CH or $CR^2$, and
    $X^8$ is $CR^2$.

IIh B is CO,
    Y is S,
    m is 2,
    $X^7$, $X^9$ and $X^{10}$ are each, independently, CH or $CR^2$, and
    $X^8$ is $COR^9$.

IIi B is CO,
    Y is S,
    m is 2,
    at least one of $X^8$ or $X^9$ is $CR^2$ in which $R^2$ is Het other than imidazolidinyl or $R^2$ is $OR^9$ and $R^9$ is Het.

IIj B is CO,
    Y is S,
    m is 2,
    at least one of $X^8$ or $X^9$ is $CR^2$ in which $R^2$ is substituted or unsubstituted pyrrolidinyl, diazabicycloheptyl, diazabicyclononyl, piperazinyl, diazepanyl, hexahydropyrrolopyrazinyl, diazabicyclooctyl, pyrrolidinyloxy, or azabicyclooctyloxy.

VIa B is CO,
    R is H, and
    $X^{24}$ is N.

VIb B is CO,
    R is H,
    $X^{24}$ is N, and
    m is 2.

VIc B is CO,
    R is H,
    $X^{24}$ is N, and
    $X^{23}$ is $CR^{12}$.

VId B is CO,
    R is H,
    m is 2,
    $X^{24}$ is N, and
    $X^{23}$ is $CR^{12}$.

VIe B is CO,
R is H,
$X^{24}$ is N,
$X^{23}$ is $CR^{12}$, and
$R^{12}$ is halogen.
VIf B is CO,
R is H,
m is 2,
$X^{24}$ is N,
$X^{23}$ is $CR^{12}$, and
$R^{12}$ is halogen.
VIg B is CO,
R is H,
$X^{22}$ is CH,
$X^{24}$ is N, and
$X^{23}$ is $CR^{12}$.
VIh B is CO,
R is H,
m is 2,
$X^{22}$ is CH,
$X^{24}$ is N, and
$X^{23}$ is $CR^{12}$.
VIi B is CO,
R is H,
m is 2,
$X^{24}$ is CH,
$X^{23}$ is $CR^{21}$, and
$R^{21}$ is selected from Formulae IX-XI,
$W^4$ is N or $NR^{13}$, and
$V^2$ is N.
VIj B is CO,
R is H,
m is 2,
$X^{22}$ is CH,
$X^{24}$ is CH,
$X^{23}$ is $CR^{21}$, and
$R^{21}$ is selected from Formulae IX-XI,
$W^4$ is N or $NR^{13}$, and
$V^2$ is N.
VIk B is CO,
R is H,
m is 2,
$X^{24}$ is CH,
$X^{23}$ is $CR^{21}$, and
$R^{21}$ is of Formula IX, and
$W^4$ is N or $NR^{13}$.
VIl B is CO,
R is H,
m is 2,
$X^{22}$ is CH,
$X^{24}$ is CH,
$X^{23}$ is $CR^{21}$, and
$R^{21}$ is of Formula IX, and
$W^4$ is N or $NR^{13}$.
VIm B is CO,
R is H,
$X^{24}$ is CH,
$X^{23}$ is $CR^{21}$,
$R^{21}$ is of Formula X, and
$V^2$ is N.
VIn B is CO,
R is H,
$X^{22}$ is CH,
$X^{24}$ is CH,
$X^{23}$ is $CR^{21}$,
$R^{21}$ is of Formula X, and
$V^2$ is N.

VIo B is CO,
R is H,
$X^{24}$ is CH,
$X^{23}$ is $CR^{21}$, and
$R^{21}$ is substituted or unsubstituted pyrrolidinyl (e.g., pyrrolidin-1-yl), morpholinyl (e.g., morpholin-4-yl), thiomorpholinyl (e.g., thiomorpholin-4-yl), imidazolidinyl (e.g., 3-propyl-imidazolidin-2-one), piperazinyl (e.g., 4-methylpiperazin-1-yl), diazepanyl (e.g., 4-methyl-1,4-diazepan-1-yl), oxazepanyl (e.g., 1,4-oxazepan-1-yl).
VIp B is CO,
R is H,
m is 2,
$X^{24}$ is CH,
at least one of $X^{22}$ and $X^{23}$ is $CR^{21}$ in which $R^{21}$ is —NHCO—NH—$C_{1-4}$-alkyl or substituted or unsubstituted pyrrolidinyl, morpholinyl, thiomorpholinyl, piperazinyl, diazepanyl, oxazepanyl, tetrahydropyranyloxy, dihydroimidazolyl, or imidazolidinyl (e.g., 3-propylimiazolidin-2-one).
VIq B is CO,
R is H,
m is 2,
$X^{24}$ is CH,
at least one of $X^{22}$ and $X^{23}$ is $CR^{21}$, and $R^{21}$ is pyrrolidinyl which is substituted by alkoxy having 1 to 6 carbon atoms, amino, mononalkylamino having 1 to 6 carbon atoms, or dialkylamino wherein each alkyl group has 1 to 6 carbon atoms.

According to a further compound and/or method aspect of the invention, the compounds are selected from:

1) 3-(1,4-Diazabicyclo[3.2.2]non-4-ylcarbonyl)-6-pyrrolidin-1-yl-1H-indazole,
2) 3-(1,4-Diazabicyclo[3.2.2]non-4-ylcarbonyl)-6-(3-methoxypyrrolidin-1-yl)-1H-indazole,
3) 3-(1,4-Diazabicyclo[3.2.2]non-4-ylcarbonyl)-6-morpholin-4-yl-1H-indazole,
4) 1-[3-(1,4-Diazabicyclo[3.2.2]non-4-ylcarbonyl)-1H-indazol-6-yl]-3-propylimidazolidin-2-one,
5) 3-(1,4-Diazabicyclo[3.2.2]non-4-ylcarbonyl)-6-(4-methyl-1,4-diazepan-1-yl)-1H-indazole,
6) 3-(1,4-Diazabicyclo[3.2.2]non-4-ylcarbonyl)-6-thiomorpholin-4-yl-1H-indazole,
7) 3-(1,4-Diazabicyclo[3.2.2]non-4-ylcarbonyl)-6-(4-methylpiperazin-1-yl)-1H-indazole,
8) 3-(1,4-Diazabicyclo[3.2.2]non-4-ylcarbonyl)-6-(1,4-oxazepan-4-yl)-1H-indazole,
9) 3-(1,4-Diazabicyclo[3.2.2]non-4-ylcarbonyl)-5-methoxy-1,2-benzisothiazole hydroformate,
10) 3-(1,4-Diazabicyclo[3.2.2]non-4-ylcarbonyl)-6-fluoro-1H-pyrazolo[3,4-b]pyridine hydroformate,
11) 3-(1,4-Diazabicyclo[3.2.2]non-4-ylcarbonyl)-6-[(3R)-3-methoxypyrrolidin-1-yl]-1H-indazole dihydroformate,
12) 3-(1,4-Diazabicyclo[3.2.2]non-4-ylcarbonyl)-5-[(3S)-3-methoxypyrrolidin-1-yl]-1H-indazole dihydroformate,
13) 3-(1,4-Diazabicyclo[3.2.2]non-4-ylcarbonyl)-5-[(3R)-3-methoxypyrrolidin-1-yl]-1H-indazole dihydroformate,
14) 3-(1,4-Diazabicyclo[3.2.2]non-4-ylcarbonyl)-6-[(3S)-3-methoxypyrrolidin-1-yl]-1H-indazole dihydroformate,
15) 3-(1,4-Diazabicyclo[3.2.2]non-4-ylcarbonyl)-5-(tetrahydro-2H-pyran-3-yloxy)-1H-indazole,
16) 3-(1,4-Diazabicyclo[3.2.2]non-4-ylcarbonyl)-6-(tetrahydro-2H-pyran-4-yloxy)-1H-indazole,
17) 3-(1,4-Diazabicyclo[3.2.2]non-4-ylcarbonyl)-6-(tetrahydro-2H-pyran-3-yloxy)-1H-indazole,
18) 3-(1,4-Diazabicyclo[3.2.2]non-4-ylcarbonyl)-6-[(3R)-3-methoxypyrrolidin-1-yl]-1,2-benzisothiazole, 19) 3-(1,4-Diazabicyclo[3.2.2]non-4-ylcarbonyl)-7-fluoro-6-methoxy-1,2-benzisothiazole,
20) 3-(1,4-Diazabicyclo[3.2.2]non-4-ylcarbonyl)-6-[(3S)-3-methoxypyrrolidin-1H-yl]-1,2-benzisothiazole,
21) N-[3-(1,4-Diazabicyclo[3.2.2]non-4-ylcarbonyl)-1-methyl-1H-indazol-6-yl]-N'-propylurea hydroformate,
22) 3-(1,4-Diazabicyclo[3.2.2]non-4-ylcarbonyl)-1-ethyl-6-methoxy-1H-indazole,
23) 3-(1,4-Diazabicyclo[3.2.2]non-4-ylcarbonyl)-6-phenyl-1H-pyrazolo[3,4-b]pyridine,
24) 3-(1,4-Diazabicyclo[3.2.2]non-4-ylcarbonyl)-6-[(1S,4S)-5-methyl-2,5-diazabicyclo[2.2.1]hept-2-yl]-1,2-benzisothiazole,
25) 3-(1,4-Diazabicyclo[3.2.2]non-4-ylcarbonyl)-6-[(1R,4R)-5-methyl-2,5-diazabicyclo[2.2.1]hept-2-yl]-1,2-benzisothiazole,
26) 6-(1,4-Diazabicyclo[3.2.2]non-4-yl)-3-(1,4-diazabicyclo[3.2.2]non-4-ylcarbonyl)-1,2-benzisothiazole,
27) 3-(1,4-Diazabicyclo[3.2.2]non-4-ylcarbonyl)-5-[4-(2,2,2-trifluoroethyl)-1,4-diazepan-1-yl]-1H-indazole,
28) 3-(1,4-Diazabicyclo[3.2.2]non-4-ylcarbonyl)-6-pyrrolidin-1-yl-1,2-benzisothiazole,
29) 3-(1,4-Diazabicyclo[3.2.2]non-4-ylcarbonyl)-6-(4-methylpiperazin-1-yl)-1,2-benzisothiazole,
30) 3-(1,4-Diazabicyclo[3.2.2]non-4-ylcarbonyl)-6-(4-methyl-1,4-diazepan-1-yl)-1,2-benzisothiazole,
31) 3-(1,4-Diazabicyclo[3.2.2]non-4-ylcarbonyl)-6-(hexahydropyrrolo[1,2-a]pyrazin-2(1H)-yl)-1,2-benzisothiazole,
32) 3-(1,4-Diazabicyclo[3.2.2]non-4-ylcarbonyl)-6-(5-methyl-2,5-diazabicyclo[2.2.2]oct-2-yl)-1,2-benzisothiazole,
33) 6-[(1S,4S)-5-cyclopropyl-2,5-diazabicyclo[2.2.1]hept-2-yl]-3-(1,4-diazabicyclo[3.2.2]non-4-ylcarbonyl)-1,2-benzisothiazole,
34) 6-[(1S,4S)-5-(cyclopropylmethyl)-2,5-diazabicyclo[2.2.1]hept-2-yl]-3-(1,4-diazabicyclo[3.2.2]non-4-ylcarbonyl)-1,2-benzisothiazole,
35) tert-Butyl (1S,4S)-5-[3-(1,4-diazabicyclo[3.2.2]non-4-ylcarbonyl)-1,2-benzisothiazol-6-yl]-2,5-diazabicyclo[2.2.1]heptane-2-carboxylate,
36) 6-[(1S,4S)-2,5-Diazabicyclo[2.2.1]hept-2-yl]-3-(1,4-diazabicyclo[3.2.2]non-4-ylcarbonyl)-1,2-benzisothiazole,
37) 3-(1,4-Diazabicyclo[3.2.2]non-4-ylcarbonyl)-6-[(1-methylpyrrolidin-3-yl)oxy]-1,2-benzisothiazole,
38) 6-(1-Azabicyclo[2.2.2]oct-3-yloxy)-3-(1,4-diazabicyclo[3.2.2]non-4-ylcarbonyl)-1,2-benzisothiazole,
39) 6-(Benzyloxy)-3-(1,4-diazabicyclo[3.2.2]non-4-ylcarbonyl)-1H-indazole,
40) 3-(1,4-Diazabicyclo[3.2.2]non-4-ylcarbonyl)-6-(1-methyl-4,5-dihydro-1H-imidazol-2-yl)-1H-indazole, wherein salts listed above can also be in free base form or in the form of another pharmaceutically acceptable salt, and free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

According to a further compound and/or method aspect of the invention, the compounds are selected from:
1) 3-(1,4-diazabicyclo[3.2.2]non-4-ylcarbonyl)-6-pyrrolidin-1-yl-1H-indazole,
2) 3-(1,4-diazabicyclo[3.2.2]non-4-ylcarbonyl)-6-(3-methoxypyrrolidin-1-yl)-1H-indazole,
3) 3-(1,4-diazabicyclo[3.2.2]non-4-ylcarbonyl)-6-morpholin-4-yl-1H-indazole,
4) 1-[3-(1,4-diazabicyclo[3.2.2]non-4-ylcarbonyl)-1H-indazol-6-yl]-3-propylimidazolidin-2-one,
5) 3-(1,4-diazabicyclo[3.2.2]non-4-ylcarbonyl)-6-(4-methyl-1,4-diazepan-1-yl)-1H-indazole,
6) 3-(1,4-diazabicyclo[3.2.2]non-4-ylcarbonyl)-6-thiomorpholin-4-yl-1H-indazole,
7) 3-(1,4-diazabicyclo[3.2.2]non-4-ylcarbonyl)-6-(4-methylpiperazin-1-yl)-1H-indazole,
8) 3-(1,4-diazabicyclo[3.2.2]non-4-ylcarbonyl)-6-(1,4-oxazepan-4-yl)-1H-indazole,
9) 3-(1,4-diazabicyclo[3.2.2]non-4-ylcarbonyl)-5-methoxy-1,2-benzisothiazole hydroformate, and
10) 3-(1,4-diazabicyclo[3.2.2]non-4-ylcarbonyl)-6-fluoro-1H-pyrazolo[3,4-b]pyridine hydroformate, wherein salts listed above can also be in free base form or in the form of another pharmaceutically acceptable salt, and free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof,) can also be in the form of a polymorph, and wherein if the compound exhibits chirality it can be in the form of a mixture of enantiomers such as a racemate or a mixture of diastereomers, or can be in the form of a single enantiomer or a single diastereomer.

The following table presents the structures for selected compounds of Formulas I-VIII in accordance with the present invention:

| Compound | Structure |
| --- | --- |
| 1) | 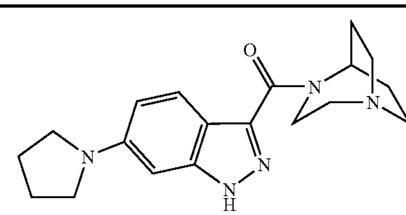 |
| 2) | 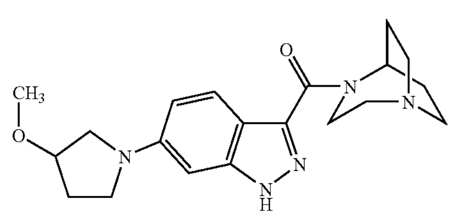 |

| Compound | Structure |
|---|---|
| 3) | 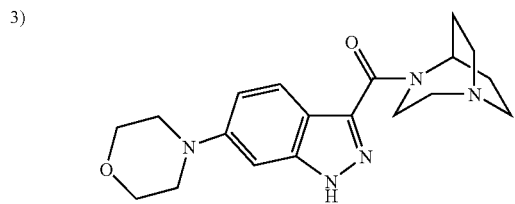 |
| 4) | 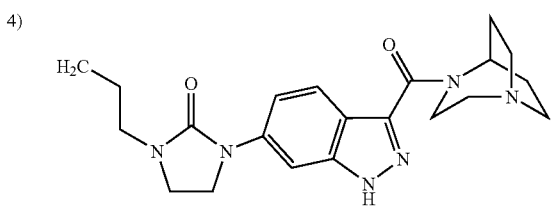 |
| 5) | 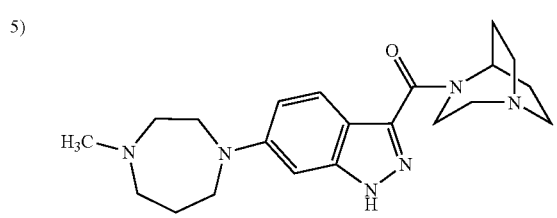 |
| 6) | 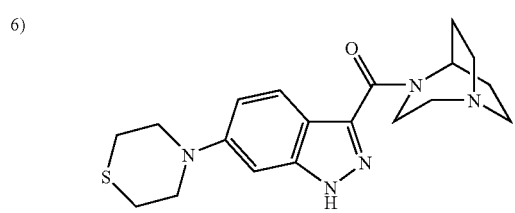 |
| 7) | 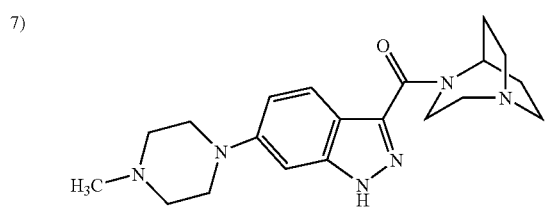 |
| 8) | 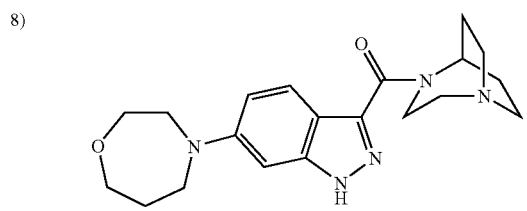 |
| 9) | 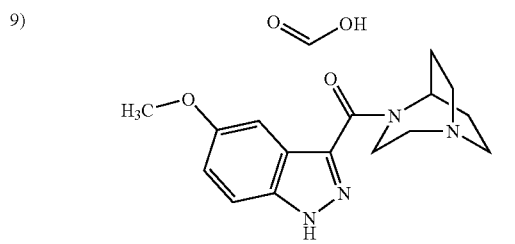 |
| 10) | 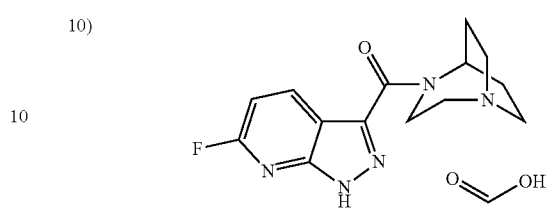 |
| 11) | 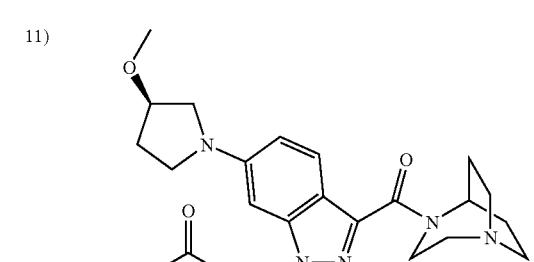 |
| 12) | 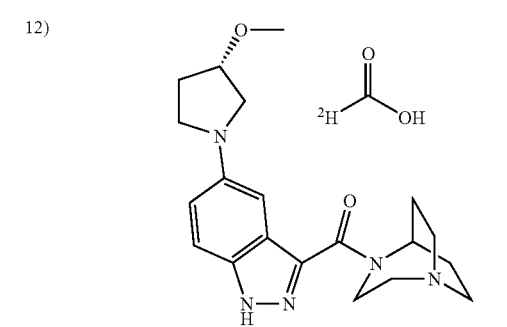 |
| 13) | 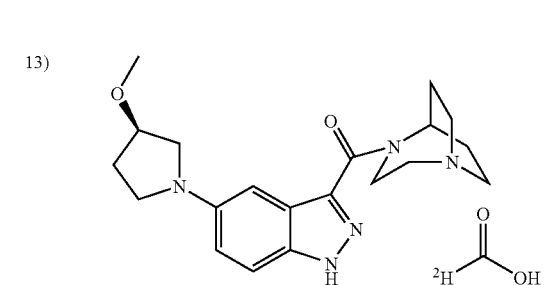 |
| 14) | 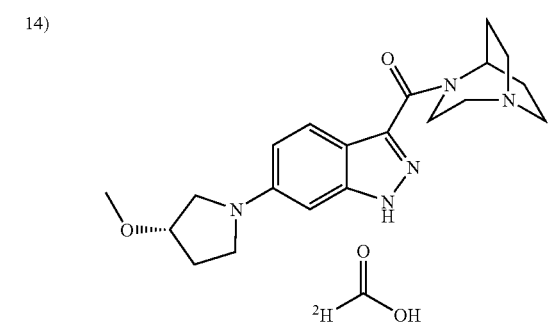 |

| Compound | Structure |
|---|---|
| 15) | 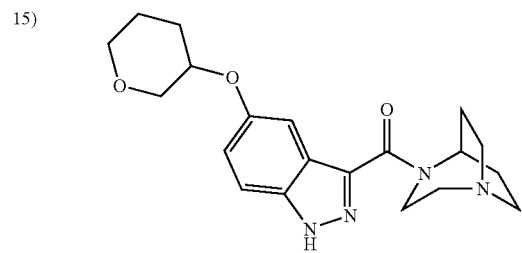 |
| 16) | 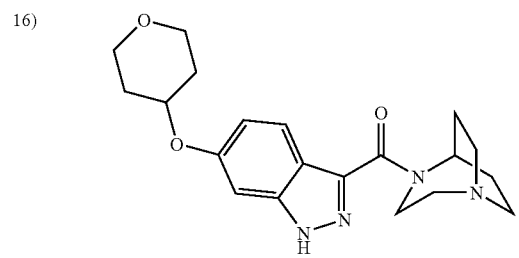 |
| 17) | 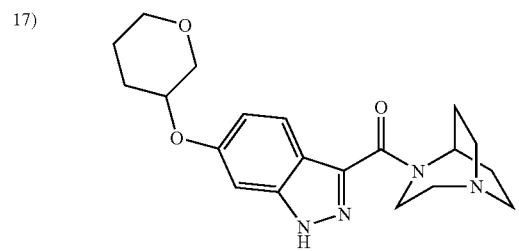 |
| 18) | 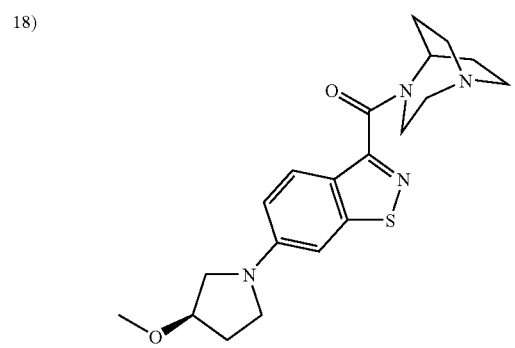 |
| 19) | 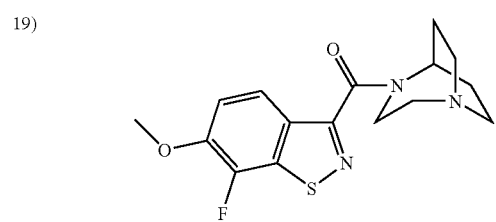 |
| Compound | Structure |
|---|---|
| 20) | 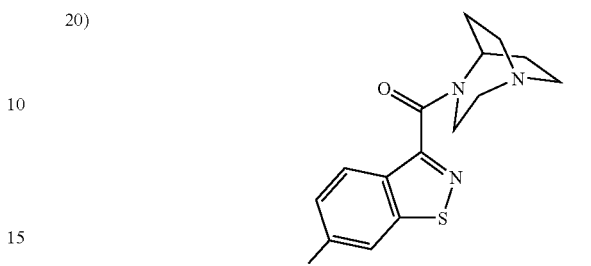 |
| 21) | 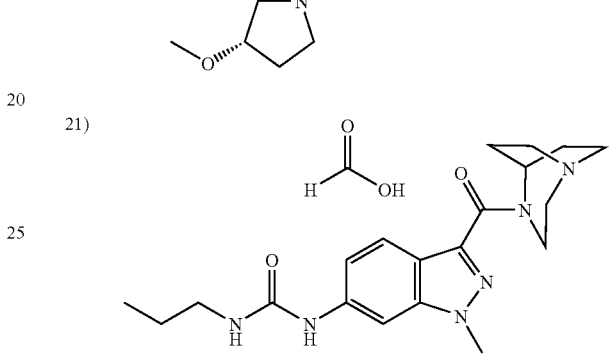 |
| 22) | 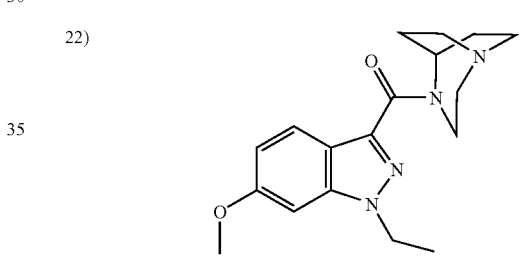 |
| 23) | 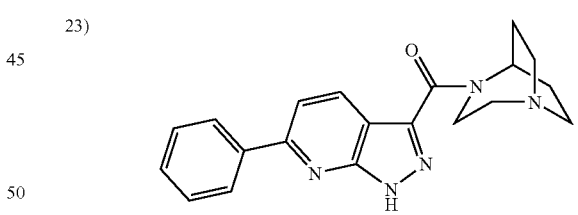 |
| 24) | 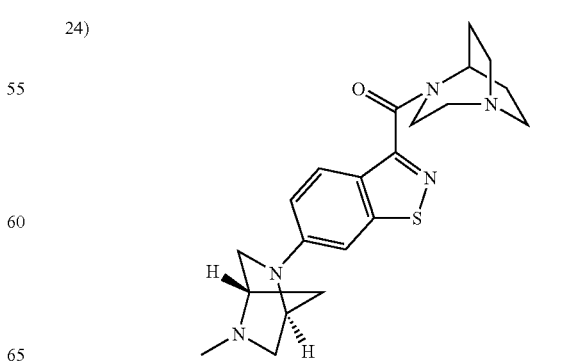 |

| Compound | Structure |
|---|---|
| 25) | 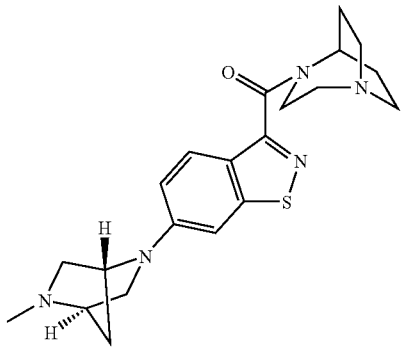 |
| 26) | 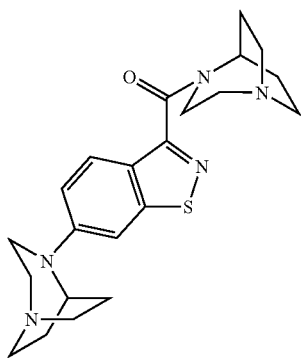 |
| 27) | 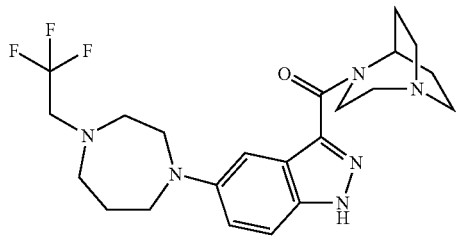 |
| 28) | 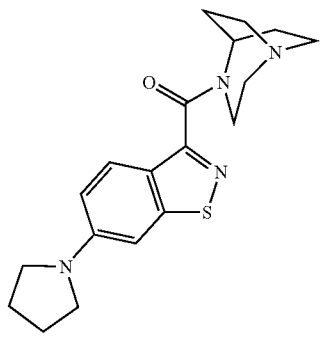 |
| Compound | Structure |
|---|---|
| 29) | 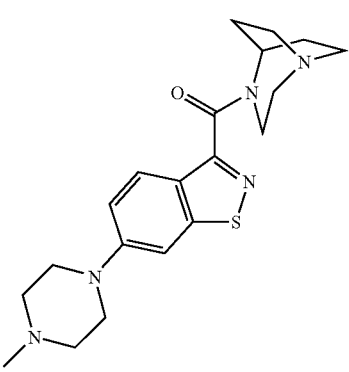 |
| 30) | 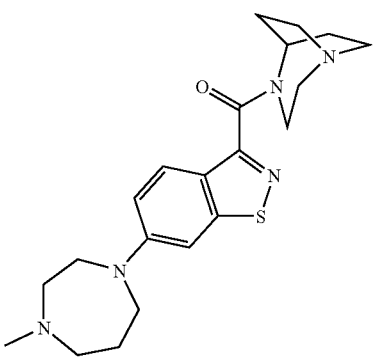 |
| 31) | 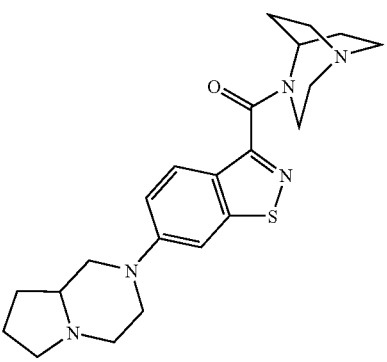 |
| 32) | 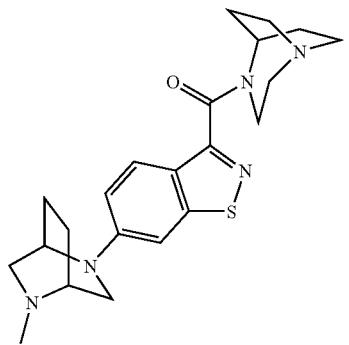 |

-continued

| Compound | Structure |
|---|---|
| 33) | 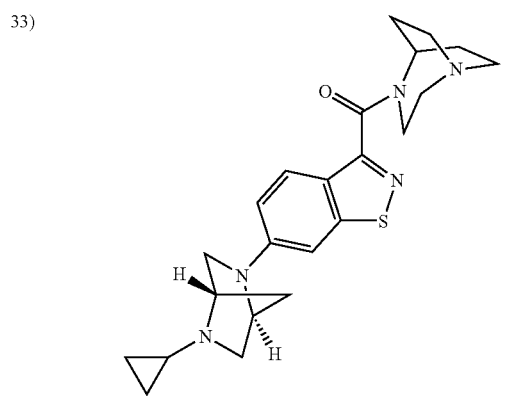 |
| 34) | 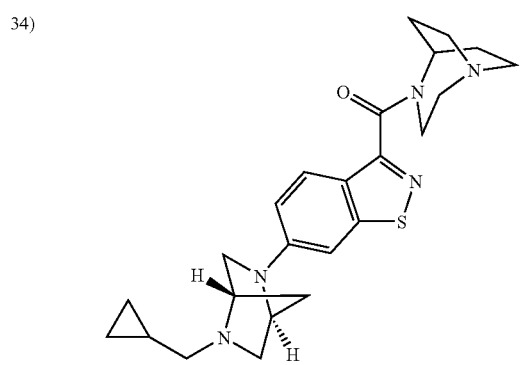 |
| 35) | 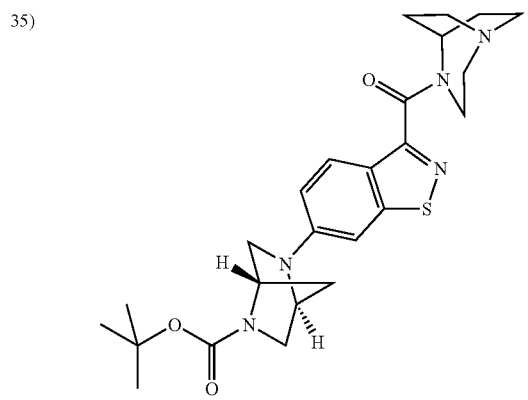 |
| 36) | 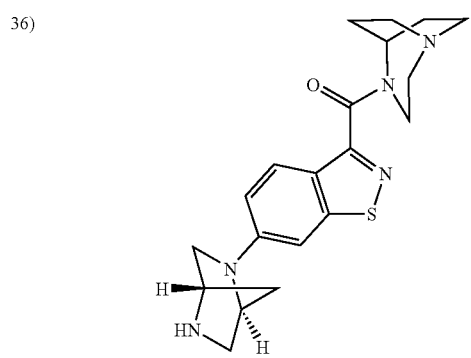 |

-continued

| Compound | Structure |
|---|---|
| 37) | 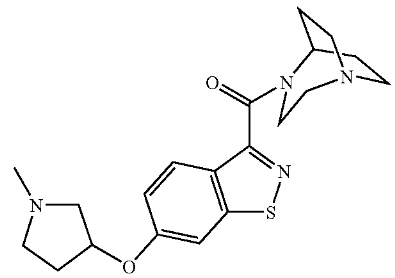 |
| 38) | 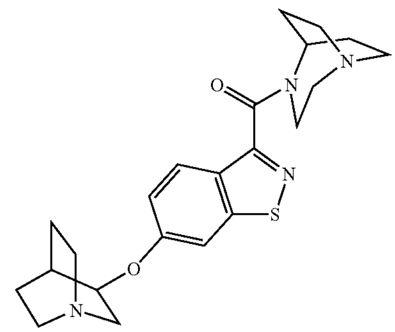 |
| 39) | 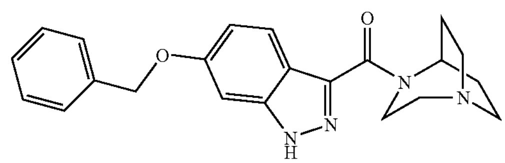 |
| 40) | 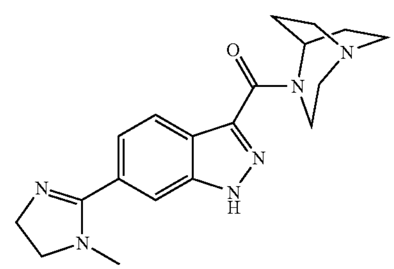 |

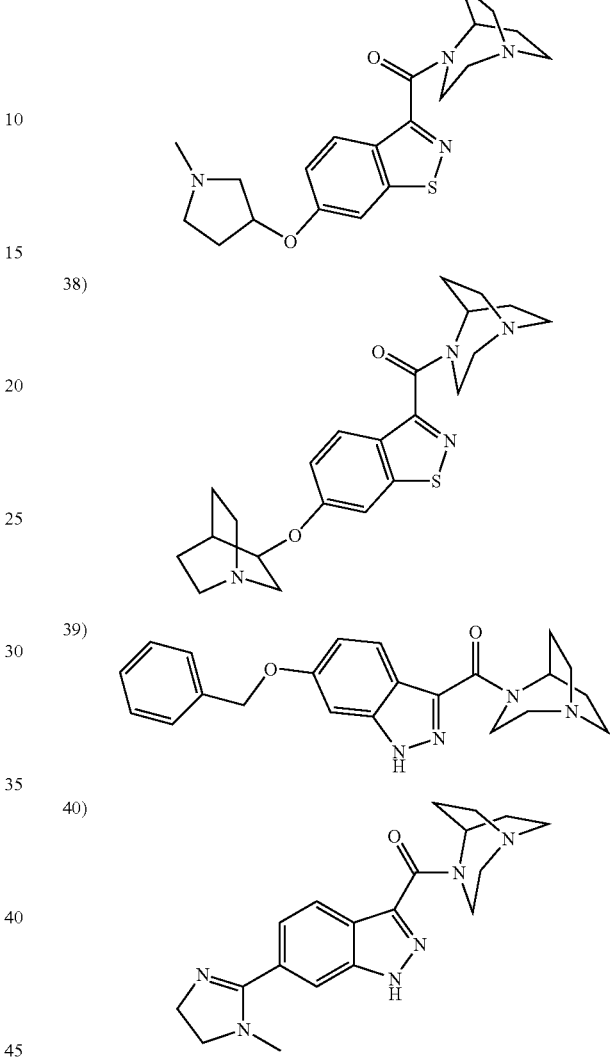

Preferred aspects include pharmaceutical compositions comprising a compound of this invention and a pharmaceutically acceptable carrier and, optionally, another active agent as discussed below; a method of stimulating or activating inhibiting alpha-7 nicotinic receptors, e.g., as determined by a conventional assay or one described herein, either in vitro or in vivo (in an animal, e.g., in an animal model, or in a mammal or in a human); a method of treating a neurological syndrome, e.g., loss of memory, especially long-term memory, cognitive impairment or decline, memory impairment, etc. method of treating a disease state modulated by nicotinic alpha-7 activity, in a mammal, e.g., a human, e.g., those mentioned herein.

The compounds of the present invention may be prepared conventionally. Some of the known processes that can be used are described below. All starting materials are known or can be conventionally prepared from known starting materials.

The synthesis of similar compounds is disclosed in copending application Ser. No. 11/123,219, filed May 6, 2005, which claims the benefit of U.S. Provisional Application Ser. No. 60/568,696, filed May 7, 2004, U.S. Provisional Application Ser. No. 60/574,712, filed May 27, 2004, and U.S. Provisional Application Ser. No. 60/629,469, filed Nov. 10, 2004, the entire disclosures of each of which are hereby incorporated by reference.

Acids that were used in the preparation of the bicyclobase amides were commercially available or were prepared by known procedures described in the literature or as described below. For example, tert-Butyl 6-fluoro-1H-pyrazolo[3,4-b]pyridine-3carboxylate was commercially available (Maybridge). 6-Bromoindazole-3-carboxylic acid and 5-bromoisothiazole-3-carboxylic acid, and their ethyl esters, were prepared as described in pending U.S. application Ser. No. 11/123,219, filed May 6, 2005, the disclosure of which is hereby incorporated by reference. N(1)- and N(2)-protected indazole acids were prepared from the ester through reaction with methoxyethoxymethyl chloride (MEM-Cl) or trimethylsilylethoxymethyl chloride (SEM-Cl) and either sodium hydride or di-isopropylethylamine, followed by hydrolysis. N(1)-Alkylated indazole-3-carboxylic acids were prepared from the corresponding indazole esters by standard alkylation conditions. Amino indazole acids were prepared using a palladium mediated cross-coupling reaction with secondary amines. Phenol derivatives were prepared from the corresponding methoxy acids using boron tribromide. 6-Amino- and 6-phenyl-7-azaindazole-3-carboxylic acids were prepared from the commercially available 6-fluoro material by reaction with a secondary amine or by nickel mediated cross-coupling with aryl Grignard reagents.

Several substituted indazole-3-acids were prepared from benzene derivatives. For example, 6-benzyloxyindazole-3-carboxylic acid and ester were prepared from 4-methoxynitrobenzene by nitro reduction with concomitant protection as the amide, nitration, amide hydrolysis, Sandmeyer reaction with copper (I) bromide, and demethylation. The phenol was alkylated with benzyl bromide and the arylbromide was subjected to reaction with diethyl malonate, decarboxylative saponification, esterification, reduction of the nitro group, and diazotization. The 5-benzyloxy analog was prepared in a similar manner from 4-benzyloxy-2-bromonitrobenzene (Parker, K. A.; Mindt, T. L. *Org Lett.* 2002, 4, 4265.) The benzyl group was removed by hydrogenolysis and the resulting phenol was transformed to ether derivatives via either alkylation or Mitsunobu reaction conditions. 5-Azaindazole-3-acid was prepared from 4-chloropyridine by metallation and trapping with diethyloxalate, cyclization with hydrazine, and saponification. 6-Azaindazole-3-acid was prepared from 4-chloro-3-nitropyridine by reaction with a malonate anion, decarboxylation, nitro reduction, diazotization, and saponification.

The benzisothiazole carboxylic acids were also prepared using similar strategies outlined for the indazole acids. For example, 6-methoxybenzisothiazole-3-carboxylic acid was prepared from 3-methoxythiophenol by reaction with oxalyl chloride and aluminum chloride followed by treatment with hydroxylamine, hydrogen peroxide, and sodium hydroxide. Amino substituted benzisothiazole acids were prepared from the requisite bromide by a palladium mediated cross-coupling reaction with secondary amines or benzophenone imine. The primary and secondary amines generated this way serve as intermediates for other ligands. For example, the amines were transformed into tertiary amines and amides using standard reductive amination and acylation reactions practiced by those of ordinary skill in the art. 5-Methoxybenzisothiazole-3-carboxylic acid was prepared form the corresponding bromide by a palladium mediated boron ester formation, oxidation, methylation and subsequent hydrolysis of the ester.

The bicycloamine that was used in the preparation of the bicyclobase amides was commercially available (Olainfarm). The bicyclobase amides were prepared from the acids and the bicycloamine using standard peptide coupling agents, such as O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), O-(benzotriazol-1-yl)-N,N,N',N'-tetramethyluronium tetrafluoroborate (TBTU), hydroxybenztriazole (HOBt) and N-(3-dimethylaminopropyl)-N'-ethylcarbodiimide (EDCI), carbonyl diimidazole (CDI), 2-chloro-1,3,-dimethylimidazolinium hexafluorophosphate (CIP), or by converting the acids to the corresponding acid chloride followed by reaction with the bicycloamine (Macor, J. E.; Gurley, D.; Lanthorn, T.; Loch, J.; Mack, R. A.; Mullen, G.; Tran, O.; Wright, N.; and J. E. Macor et al., "The 5-HT3-Antagonist Tropisetron (ICS 205-930) was a Potent and Selective α-7 Nicotinic Receptor Partial Agonist," *Bioorg. Med. Chem. Lett.* 2001, 9, 319-321). The couplings were generally performed at room temperature for 18-24 hours. The resultant adducts were isolated and purified by standard techniques practiced by those of ordinary skill in the art, such as chromatography or recrystallization.

The nicotinic ligands were, alternatively, prepared by modification of other nicotinic ligands. For example, the 6-(3-propylimidazolidin-2-one) ligand was prepared from the corresponding bromide ligand by a palladium-catalyzed cross-coupling reaction. Other halogen-substituted ligands served as precursors for modified ligands where appropriate. As a final example, urea analogs were prepared from aniline substituted analogs.

One of ordinary skill in the art will recognize that compounds of Formulas I-VIII can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulas I-VIII can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2$H, $^3$H, $^{11}$C, $^{13}$C and/or $^{14}$C. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as pharmaceutically acceptable salts or prodrugs of all the compounds of the present invention for which salts or prodrugs can be prepared. Pharmaceutically acceptable salts include those obtained by reacting the main compound, functioning as a bas with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, or a maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of Formulas I-VIII can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of Formulas I-VIII can exist in different solvate forms. Solvates of the compounds of the invention may also form when solvent molecules are incorporated into the crystalline lattice structure of the compound molecule during the crystallization process.

The compounds of the invention can be administered alone or as an active ingredient of a formulation. Thus, the present invention also includes pharmaceutical compositions of compounds of Formulas I-VIII, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their alpha-7 stimulating activity and, preferably their high degree of selectivity, the compounds of the present invention can be administered to anyone needing stimulation of alpha-7 receptors. Administration may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or memory loss, e.g., other α-7 agonists, PDE4 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and glanthanamine). In such combinations, each active ingredient can be administered either in accordance with their usual dosage range or a dose below their usual dosage range.

The compounds of the invention can be used in conjunction with "positive modulators" which enhance the efficacy of nicotinic receptor agonists. See, e.g., the positive modulators disclosed in WO 99/56745, WO 01/32619, and WO 01/32622. Such combinational therapy can be used in treating conditions/diseases associated with reduced nicotinic transmission.

Further the compounds may be used in conjunction with compounds that bind to Aβ peptides and thereby inhibit the binding of the peptides to α7nAChr subtypes. See, e.g., WO 99/62505.

The present invention further includes methods of treatment that involve activation of α-7 nicotinic receptors. Thus, the present invention includes methods of selectively activating/stimulating α-7 nicotinic receptors in a patient (e.g., a mammal such as a human) wherein such activation/stimulation has a therapeutic effect, such as where such activation may relieve conditions involving neurological syndromes, such as the loss of memory, especially long-term memory. Such methods comprise administering to a patient (e.g., a mammal such as a human), an effective amount of a compound of Formulas I-VIII, alone or as part of a formulation, as disclosed herein.

In accordance with a method aspect of the invention, there is provided a method of treating a patient (e.g., a mammal such as a human) suffering from a disease state (e.g., memory impairment) comprising administering to the patient a compound according to Formulas I-VIII. Preferably, the disease state involves decreased nicotinic acetylcholine receptor activity.

In accordance with a method aspect of the invention there is provided a method for the treatment or prophylaxis of a disease or condition resulting from dysfunction of nicotinic acetylcholine receptor transmission in a patient (e.g., a mammal such as a human) comprising administering an effective amount of a compound according to Formulas I-VIII.

In accordance with a method aspect of the invention there is provided a method for the treatment or prophylaxis of a disease or condition resulting from defective or malfunctioning nicotinic acetylcholine receptors, particularly α7nACh receptors, in a patient (e.g., a mammal such as a human) comprising administering an effective amount of a compound according to Formulas I-VIII.

In accordance with a method aspect of the invention there is provided a method for the treatment or prophylaxis of a disease or condition resulting from suppressed nicotinic acetylcholine receptor transmission in a patient (e.g., a mammal such as a human) comprising administering an amount of a compound according to Formulas I-VIII effective to activate α7nACh receptors.

In accordance with another method aspect of the invention there is provided a method for the treatment or prophylaxis of a psychotic disorder, a cognition impairment (e.g., memory impairment), or neurodegenerative disease in a patient (e.g., a mammal such as a human) comprising administering an effective amount of a compound according to Formulas I-VIII.

In accordance with another method aspect of the invention there is provided a method for the treatment or prophylaxis of a disease or condition resulting from loss of cholinergic synapses in a patient (e.g., a mammal such as a human) comprising administering an effective amount of a compound according to Formulas I-VIII.

In accordance with another method aspect of the invention there is provided a method for the treatment or prophylaxis of a neurodegenerative disorder by activation of α7nACh receptors in a patient (e.g., a mammal such as a human) comprising administering an effective amount of a compound according to Formulas I-VIII.

In accordance with another method aspect of the invention there is provided a method for protecting neurons in a patient (e.g., a mammal such as a human) from neurotoxicity induced by activation of α7nACh receptors comprising administering an effective amount of a compound according to Formulas I-VIII.

In accordance with another method aspect of the invention there is provided a method for the treatment or prophylaxis of a neurodegenerative disorder by inhibiting the binding of Aβ peptides to α7nACh receptors in a patient (e.g., a mammal such as a human) comprising administering an effective amount of a compound according to Formulas I-VIII.

In accordance with another method aspect of the invention there is provided a method for protecting neurons in a patient (e.g., a mammal such as a human) from neurotoxicity induced by Aβ peptides comprising administering an effective amount of a compound according to Formulas I-VIII.

In accordance with another method aspect of the invention there is provided a method for alleviating inhibition of cholinergic function induced by Aβ peptides in a patient (e.g., a mammal such as a human) comprising administering an effective amount of a compound according to Formulas I-VIII.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The compounds of the present invention are nicotinic alpha-7 ligands, preferably agonists, especially partial agonists, for the alpha-7 nicotinic acetylcholine receptor. Assays for determining nicotinic acetylcholine activity are known within the art. See, e.g., Davies, A. R., et al., Characterisation of the binding of [3H]methyllycaconitine: a new radioligand for labelling alpha 7-type neuronal nicotinic acetylcholine receptors. Neuropharmacology, 1999. 38(5): p. 679-90. As agonists for α7nACh receptors, the compounds are useful in the prophylaxis and treatment of a variety of diseases and conditions associated with the central nervous system. Nicotinic acetylcholine receptors are ligand-gastrol ion-channel receptors that are composed of five subunit proteins which form a central ion-conducting pore. Presently, there are eleven known neuronal nACh receptor subunits ($\alpha 2$-$\alpha 9$ and $\beta 2$-$\beta 4$). There are also five further subunits expressed in the peripheral nervous system ($\alpha 1$, $\beta 1$, $\gamma$, $\delta$, $\epsilon$).

The nACh receptor subtypes can be homopentameric or heteropentameric. The subtype which has received considerable attention is the homopentameric α7 receptor subtype formed from five α7 subunits. The α7nACh receptors exhibit a high affinity for nicotine (agonist) and for α-bungarotoxin (antagonist). Studies have shown the α7nACh receptor agonists can be useful in the treatment of psychotic diseases, neurodegenerative diseases, and cognitive impairments, among other things. While nicotine is a known agonist, there is a need for the development of other α7nACh receptor agonists, especially selective agonists, which are less toxic or exhibit fewer side effects than nicotine.

The compound anabaseine, i.e., 2-(3-pyridyl)-3,4,5,6-tetrahydropyridine is a naturally occurring toxin in certain marine worms (nemertine worms) and ants. See, e.g., Kem et al., Toxicon, 9:23, 1971. Anabaseine is a potent activator of mammalian nicotinic receptors. See, e.g., Kem, Amer. Zoologist, 25, 99, 1985. Certain anabaseine analogs such as anabasine and DMAB (3-[4-(dimethylamino)benzylidene]-3,4,5,6-tetrahydro-2',3'-bipyridine) are also known nicotinic receptor agonists. See, e.g., U.S. Pat. No. 5,602,257 and WO 92/15306. One particular anabaseine analog, (E-3-[2,4-dimethoxy-benzylidene]-anabaseine, also known as GTS-21 and DMXB (see, e.g., U.S. Pat. No. 5,741,802), is a selective partial α7nACh receptor agonist that has been studied extensively. For example, abnormal sensory inhibition is a sensory processing deficit in schizophrenics and GTS-21 has been found to increase sensory inhibition through interaction with α7nACh receptors. See, e.g., Stevens et al., Psychopharmacology, 136: 320-27 (1998).

Another compound which is known to be a selective α7nACh receptor agonist is Tropisetron, i.e., 1αH, 5αH-tropan-3α-yl indole-3-carboxylate. See J. E. Macor et al., The 5-HT3-Antagonist Tropisetron (ICS 205-930) is a Potent and Selective A7 Nicotinic Receptor Partial Agonist. *Bioorg. Med. Chem. Lett.* 2001, 319-321).

Agents that bind to nicotinic acetylcholine receptors have been indicated as useful in the treatment and/or prophylaxis of various diseases and conditions, particularly psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (i.e., analgesic use), providing neuroprotection, and treating jetlag. See, e.g., WO 97/30998; WO 99/03850; WO 00/42044; WO 01/36417; Holladay et al., J. Med. Chem., 40:26, 4169-94 (1997); Schmitt et al., Annual Reports Med. Chem., Chapter 5, 41-51 (2000); Stevens et al., Psychopharmatology, (1998) 136: 320-27; and Shytle et al., Molecular Psychiatry, (2002), 7, pp. 525-535.

Thus, in accordance with the invention, there is provided a method of treating a patient, especially a human, suffering from psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder) comprising administering to the patient an effective amount of a compound according to Formulas I-VIII.

Neurodegenerative disorders included within the methods of the present invention include, but are not limited to, treatment and/or prophylaxis of Alzheimer's diseases, Pick's disease, diffuse Lewy Body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Straussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, α7nACh receptor agonists, such as the compounds of the present invention can be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia. See, e.g., WO 99/62505. Thus, in accordance with the invention, there is provided a method of treating a patient, especially a human, suffering from age-related dementia and other dementias and conditions with memory loss comprising administering to the patient an effective amount of a compound according to Formulas I-VIII.

Thus, in accordance with a further embodiment, the present invention includes methods of treating patients suffering from memory impairment due to, for example, mild cognitive impairment due to aging, Alzheimer's disease, schizophrenia, Parkinson's disease, Huntington's disease, Pick's disease, Creutzfeldt-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to Formulas I-VIII.

Amyloid precursor protein (APP) and Aβ peptides derived therefrom, e.g., $A\beta_{1-40}$, $A\beta_{1-42}$, and other fragments, are known to be involved in the pathology of Alzheimer's disease. The $A\beta_{1-42}$ peptides are not only implicated in neurotoxicity but also are known to inhibit cholinergic transmitter function. Further, it has been determined that Aβ peptides bind to α7nACh receptors. Thus, agents which block the binding of the Aβ peptides to α-7 nAChRs are useful for treating neurodegenerative diseases. See, e.g., WO 99/62505. In addition, stimulation α7nACh receptors can protect neurons against cytotoxicity associated with Aβ peptides. See, e.g., Kihara, T. et al., Ann. Neurol., 1997, 42, 159.

Thus, in accordance with an embodiment of the invention there is provided a method of treating and/or preventing dementia in an Alzheimer's patient which comprises administering to the subject a therapeutically effective amount of a compound according to Formulas I-VIII to inhibit the binding of an amyloid beta peptide (preferably, $A\beta_{1-42}$) with nACh receptors, preferable α7nACh receptors, most preferably, human α7nACh receptors (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities).

The present invention also provides methods for treating other amyloidosis diseases, for example, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis anthropathy, and Finnish and Iowa amyloidosis.

In addition, nicotinic receptors have been implicated as playing a role in the body's response to alcohol ingestion. Thus, agonists for α7nACh receptors can be used in the treatment of alcohol withdrawal and in anti-intoxication therapy. Thus, in accordance with an embodiment of the invention there is provided a method of treating a patient for alcohol withdrawal or treating a patient with anti-intoxication therapy comprising administering to the patient an effective amount of a compound according to Formulas I-VIII.

Agonists for the α7nACh receptor subtypes can also be used for neuroprotection against damage associated with strokes and ischemia and glutamate-induced excitotoxicity. Thus, in accordance with an embodiment of the invention there is provided a method of treating a patient to provide for neuroprotection against damage associated with strokes and ischemia and glutamate-induced excitotoxicity comprising administering to the patient an effective amount of a compound according to Formulas I-VIII.

As noted above, agonists for the α7nACh receptor subtypes can also be used in the treatment of nicotine addiction, inducing smoking cessation, treating pain, and treating jetlag, obesity, diabetes, and inflammation. Thus, in accordance with an embodiment of the invention there is provided a method of treating a patient suffering from nicotine addiction, pain, jetlag, obesity and/or diabetes, or a method of inducing smoking cessation in a patient comprising administering to the patient an effective amount of a compound according to Formulas I-VIII.

The inflammatory reflex is an autonomic nervous system response to an inflammatory signal. Upon sensing an inflammatory stimulus, the autonomic nervous system responds through the vagus nerve by releasing acetylcholine and activating nicotinic α7 receptors on macrophages. These macrophages in turn release cytokines. Dysfunctions in this pathway have been linked to human inflammatory diseases including rheumatoid arthritis, diabetes and sepsis. Macrophages express the nicotinic α7 receptor and it is likely this receptor that mediates the cholinergic anti-inflammatory response. Therefore, compounds with affinity for the α7nACh receptor on macrophages may be useful for human inflammatory diseases including rheumatoid arthritis, diabetes and sepsis. See, e.g., Czura, C J et al., J. Intern. Med., 2005, 257(2), 156-66.

Thus, in accordance with an embodiment of the invention there is provided a method of treating a patient (e.g., a mammal, such as a human) suffering from an inflammatory disease, such as, but not limited to, rheumatoid arthritis, diabetes or sepsis, comprising administering to the patient an effective amount of a compound according to Formulas I-VIII.

In addition, due to their affinity to α7nACh receptors, labeled derivatives of the compounds of Formulas I-VIII (e.g., $C^{11}$ or $F^{18}$ labeled derivatives), can be used in neuroimaging of the receptors within, e.g., the brain. Thus, using such labeled agents in vivo imaging of the receptors can be performed using, e.g., PET imaging.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeldt-Jakob disease, HIV, cardiovascular disease, and head trauma as well as age-related cognitive decline.

Thus, in accordance with an embodiment of the invention there is provided a method of treating a patient suffering from, for example, mild cognitive impairment (MCI), vascular dementia (VaD), age-associated cognitive decline (AACD), amnesia associated w/open-heart-surgery, cardiac arrest, and/or general anesthesia, memory deficits from early exposure of anesthetic agents, sleep deprivation induced cognitive impairment, chronic fatigue syndrome, narcolepsy, AIDS-related dementia, epilepsy-related cognitive impairment, Down's syndrome, Alcoholism related dementia, drug/substance induced memory impairments, Dementia Puglistica (Boxer Syndrome), and animal dementia (e.g., dogs, cats, horses, etc.) comprising administering to the patient an effective amount of a compound according to Formulas I-VIII.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention can be administered to patients, e.g., mammals, particularly humans, at typical dosage levels customary for α-7 nicotinic receptor agonists such as the known α-7 nicotinic receptor agonist compounds mentioned above. For example, the compounds can be administered, in single or multiple doses, by oral administration at a dosage level of, for example, 0.0001-10 mg/kg/day, e.g., 0.01-10 mg/kg/day. Unit dosage forms can contain, for example, 1-200 mg of active compound. For intravenous administration, the compounds can be administered in single or multiple dosages.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The compounds of the invention also are useful as intermediates for making other compounds of the inventive genus. Thus, for example, compounds exhibiting relatively low activity are also useful for preparing other compounds within the inventive genus.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

Using the following examples and further procedures described below, the following compounds were prepared.

EXAMPLES

All spectra were recorded at 300 MHz on a Bruker Instruments NMR unless otherwise stated. Coupling constants (J) are in Hertz (Hz) and peaks are listed relative to TMS (δ 0.00 ppm). Microwave reactions were performed using a Personal Chemistry Optimizer™ microwave reactor in 2.5 mL or 5 mL Personal Chemistry microwave reactor vials. All reactions were performed at 200° C. for 600 s with the fixed hold time ON unless otherwise stated. Sulfonic acid ion exchange resins (SCX) were purchased from Varian Technologies. Analytical HPLC was performed on 4.6 mm×100 mm Xterra $RP_{18}$ 3.5μ columns using (i) a gradient of 20/80 to 80/20 water (0.1% formic acid)/acetonitrile (0.1% formic acid) over 6 min (Method A), (ii) a gradient of 10/90 to 90/10 water (0.1% formic acid)/acetonitrile (0.1% formic acid) over 8 min (Method B), or (iii) a gradient of 20/80 to 80/20 water (0.1% formic acid)/acetonitrile (0.1% formic acid) over 8 min (Method C), or (iv) a gradient of 10/90 to 60/40 water (0.1% formic acid)/acetonitrile (0.1% formic acid) over 8 min (Method D). Preparative HPLC was performed on 30 mm×100 mm Xterra Prep $RP_{18}$ 5μ columns using an 8 min gradient of 5/95 to 80/20 water (0.1% formic acid)/acetonitrile (0.1% formic acid), unless otherwise stated. Hydrochloride salts of the bicycle amides were prepared by adding an ethereal solution of hydrochloric acid to a methanolic solution of the bicyclic amide, followed by isolation of the resulting precipitate.

Representative Procedures.

I. Starting Materials

Example 1

Example 1 provides a preparation of substituted benzisothiazole-3-carboxylic acids from the corresponding thiophenols.

To a solution of 3-methoxythiophenol (26.7 mmol) in ether (20 mL) was added oxalyl chloride (43 mmol) dropwise. The mixture was heated at reflux for 1.5 h, cooled to rt (room temperature), and concentrated in vacuo. The resulting yellow oil was dissolved in dichloromethane (50 mL), cooled to 0° C., and was treated with aluminum chloride (32.0 mmol) in portions. The mixture was heated at reflux for 30 min, cooled to rt, and poured onto ice water with stirring. The organic layer was separated and successively washed with saturated, aqueous sodium bicarbonate, water, and brine. The organic layer was dried over magnesium sulfate, filtered and concentrated in vacuo. The residue was purified by chromatography (4/1 ethyl acetate/hexane), thus providing 6-methoxy-1-benzothiophene-2,3-dione in 47% yield as an orange solid.

To a mixture of the dione (0.44 mmol) in 30% aqueous solution of ammonium hydroxide (2.0 mL) was added 35% aqueous solution hydrogen peroxide (0.2 mL) and the reaction mixture was maintained for 12 h. The precipitated pink solids were isolated by filtration, washed with water, and dried under high vacuum, thus providing the amide in 42% yield.

To a solution of the amide (5.46 mmol) in methanol (100 mL) was added 10 N sodium hydroxide (12 mL). The mixture was heated at reflux for 12 h, cooled to rt, and was acidified to pH<2 by the slow addition of conc. hydrochloric acid. The organic layer was extracted with dichloromethane (2×) and was dried over sodium sulfate. The crude product was purified by chromatography (300/50/1 dichloromethane/methanol/formic acid), thus providing the acid in 89% as a pink solid.

The following acids were prepared using this method:
6-Bromobenzisothiazole-3-carboxylic acid.
5-Bromobenzisothiazole-3-carboxylic acid.
6-Methoxybenzisothiazole-3-carboxylic acid.

The following esters were prepared from the acid using ethanol and sulfuric acid:
Ethyl 6-bromobenzisothiazole-3-carboxylate.
Ethyl 5-bromobenzisothiazole-3-carboxylate.
Ethyl 6-methoxybenzisothiazole-3-carboxylate.

The following procedure was used to prepare benzisothiazole tert-butyl esters:

Di-tert-butyldicarbonate (128 mmol) was added to a suspension of 6-bromo-1,2-benzisothiazole-3-carboxylic acid (46.5 mmol) and 4-dimethylaminopyridine (4.26 mmol) in tert-butyl alcohol (40.0 mL) and tetrahydrofuran (40.0 mL) and the reaction mixture was heated at 65° C. for 16 hours. There was vigorous carbon dioxide evolution which gradually subsided as the mixture become homogeneous. The reaction mixture was concentrated and the residue was dissolved in dichloromethane. The dichloromethane solution was filtered through silica gel (ca. 50 g) and the eluent was concentrated to provide the ester product in 99% yield.

The following ester was prepared using this method:
tert-Butyl 5-bromo-1,2-benzisothiazole-3-carboxylate.
tert-Butyl 6-bromo-1,2-benzisothiazole-3-carboxylate.

Example 2

Example 2 provides a method for the preparation of 5-methoxy benzo[d]isothiazole-3-carboxylic acid Potassium acetate (119 mmol) and palladium (II) acetate (1.20 mmol) were added to a solution of ethyl 5-bromobenzo[d]isothiazole-3-carboxylate (39.84 mmol) in N,N-dimethylformamide (250 ml) and the reaction mixture was maintained for 30 min. Bis(pinacolato)diboron (43.7 mmol) was added and the reaction mixture was heated at 85° C. for 5 h. The reaction mixture was quenched with water (1000 mL) and the resulting solution was extracted with ethyl acetate (3×250 mL). The combined organic layers were dried (magnesium sulfate) and concentrated. The residue was purified by chromatography (petroleum ether/ethyl acetate, 50:1) to provide the boronic ester in 52% yield.

Hydrogen peroxide (3.70 mmol) was added dropwise to a cold (0° C.) solution of the ester (3.00 mmol) in tetrahydrofuran (4 mL) and water (2 mL). The resulting solution was allowed to warm to rt and was maintained for 5 h. The reaction mixture was extracted with ether (3×10 mL) and the combined organic layers were dried (magnesium sulfate) and concentrated to provide the phenol in 99% yield. Iodomethane (21.7 mmol) was added to a suspension of the phenol (17.9 mmol) and potassium carbonate (21.7 mmol) in N,N-dimethylformamide (50 mL) and the reaction mixture was maintained at room temperature for 24 h. The reaction mixture was diluted with water (400 mL) and was extracted with ethyl acetate (3×100 mL). The combined organic layers were washed with water (50 mL), brine (50 mL), and dried (magnesium sulfate). The residue was purified by chromatography (petroleum ether/ethyl acetate, 100/1 to 70/1) to provide the ether in 31% yield.

A solution of sodium hydroxide (2 N, 12 mL) was added to a solution of the ester (5.06 mmol) in tetrahydrofuran (50 mL) and ethanol (50 mL) and the resulting solution was heated at reflux for 3 h. The reaction mixture was concentrated, re-dissolved in water (12 mL), and the pH was adjusted to 1-2 by the addition of 5% hydrochloric acid. The solids were collected by filtration, washed with water, and dried to provide the acid in 96% yield as a light yellow solid.

The following acid was prepared using this method:
5-Methoxybenzo[d]isothiazole-3-carboxylic acid

Example 3

Example 3 provides a method for the preparation of isatins from anilines and the conversion of the isatins to the corresponding indazole-3-carboxylic acids.

A solution of the substituted aniline (565 mL) in 6N hydrochloric acid (106 mL) was added to a suspension of 2,2,2-trichloro-1-ethoxyethanol (678 mL) and sodium sulfate (3.15 mol) in water (1.4 L) and the reaction mixture was stirred vigorously for 1 h. A solution of hydroxylamine hydrochloride (2.08 mol) in water (650 mL) was added in one portion and the reaction mixture was heated at 80° C. for 1.5 h. The reaction mixture was cooled to 10° C. and the precipitated solids were collected by filtration, washed with water, and dried to provide the amide in 91% yield.

The amide was added to sulfuric acid (1.9 L) and the reaction mixture was heated at 60° C. for 6 h. The reaction mixture was allowed to cool to room temperature and was cautiously poured onto ice (7 kg). The precipitated solids were collected by filtration, washed with water, and dried to provide the isatin in 61% yield.

The conversion of the substituted isatins to the corresponding indazole-3-carboxylic acids is essentially the same method as described for indazole-3-carboxylic acid: Snyder, H. R., et. al. *J. Am. Chem. Soc.* 1952, 74, 2009. The substituted isatin (22.1 mmol) was diluted with 1 N sodium hydroxide (24 mL) and was heated at 50° C. for 30 min. The burgundy solution was allowed to cool to rt and was maintained for 1 h. The reaction mixture was cooled to 0° C. and was treated with a 0° C. solution of sodium nitrite (22.0 mmol) in water (5.5 mL). This solution was added through a pipet submerged below the surface of a vigorously stirred solution of sulfuric acid (2.3 mL) in water (45 mL) at 0° C. The addition took 15 min and the reaction was maintained for an additional 30 min. A cold (0° C.) solution of tin (II) chloride dihydrate (52.7 mmol) in concentrated hydrochloric acid (20 mL) was added to the reaction mixture over 10 min and the reaction mixture was maintained for 60 min. The precipitated solids were isolated by filtration, washed with water, and dried to give a quantitative mass balance. This material was of sufficient purity ($^1$H NMR and LC/MS) to use in the next step without further purification. Alternatively, the acid was recrystallized from acetic acid to provide pure material. Ethyl esters were prepared from the acids using sulfuric acid in ethanol.

The following acids were prepared using this method:
5-Bromo-1H-indazole-3-acid.
6-Bromo-1H-indazole-3-acid.
5-Methoxy-1H-indazole-3-acid.
6-Methoxy-1H-indazole-3-acid.
Ethyl 5-bromo-1H-indazole-3-carboxylate.
Ethyl 6-bromo-1H-indazole-3-carboxylate.
Ethyl 5-methoxy-1H-indazole-3-carboxylate.
Ethyl 6-methoxy-1H-indazole-3-carboxylate.

Example 4

Example 4 provides a method for the preparation of N-1-alkylated indazole-3-carboxylic acids from the corresponding indazole ester.

Ethyl 6-methoxy-1H-indazole-3-carboxylate (9.08 mmol) was added in portions to a suspension of sodium hydride (60% dispersion in mineral oil, 10.8 mmol) in tetrahydrofuran (122 mL) at 0° C. The reaction mixture was allowed to warm to room temperature and was maintained for 30 min. Iodoethane (45.8 mmol) was added and the mixture was maintained for 16 h. The reaction mixture was partitioned between water (50 mL) and ethyl acetate (50 mL) and the layers were separated. The organic layer was washed with brine (25 mL), dried (magnesium sulfate), and concentrated. The residue was purified by chromatography using a gradient of 9/1 to 7/3 hexanes/ethyl acetate to yield the purified ester. The ester was dissolved in ethanol (20 mL) and 5.0 M of sodium hydroxide in water (12 mL) was added. The reaction mixture was maintained for 16 h, diluted with water (100 mL) and acidified with 6 N HCl. The precipitate was collected to provide the product (54%) as a white solid.

The following acids were prepared using this method:
1-Ethyl-6-methoxy-1H-indazole-3-carboxylic acid.
6-Bromo-1-methyl-1H-indazole-3-carboxylic acid.

Example 5

Example 5 provides a method for the trapping of indazole aryllithiums with ketones and the coupling with 3-aminoquinuclidine to form heterocyclic derivatives.

tert-Butyl 6-bromoindazole-3-carboxylate was prepared from the acid by reaction with a 2-fold excess of di-tert-butyldicarbonate followed by treatment with sodium hydroxide. To a suspension of sodium hydride (60% mineral oil dispersion) (4.8 mmol) in tetrahydrofuran (40 mL) at 0° C. was slowly added a solution of tert-butyl 6-bromoindazole-3-carboxylate (4.0 mmol) in tetrahydrofuran (4 mL). After stirring for 0.5 h at 0° C., the mixture was cooled to −78° C. and a 1.7 M solution of tert-butyllithium in pentane (5.1 mmol) was added. After 0.5 h at −78° C., a solution of N,N-dimethylformamide (5 mmol) in tetrahydrofuran (1 mL) was added dropwise. The mixture was stirred at −78° C. for 1 h and warmed to 0° C. The reaction mixture was quenched with saturated aqueous ammonium chloride and the mixture was partitioned between ethyl acetate (100 mL) and water (100 mL). The organic layer was separated, washed with brine (50 mL), dried (magnesium sulfate), and concentrated. The residue was purified by chromatography (70/30 ethyl acetate/hexanes) to yield the aldehyde as a colorless solid.

The following acids and esters were prepared using this method:
tert-Butyl 6-formyl-1H-indazole-3-carboxylate.

Example 6

Example 6 provides a preparation of amidine substituted indazole-3-carboxylic acids from the corresponding aldehydes.

N-Methyl-1,2-ethanediamine (4.7 mmol) was added to a solution of tert-butyl 6-formyl-1H-indazole-3-carboxylate (4.2 mmol) in tert-butanol (40 mL) and the reaction mixture was maintained for 30 min. Potassium carbonate (10 mmol) and iodine (5.3 mmol) were added and the slurry was heated at 70° C. for 3 h. The reaction mixture was allowed to cool to rt and was quenched with aqueous sodium thiosulfate (40 mL). The aqueous layer was extracted with 9/1 dichloromethane/methanol and the combined organic layers were dried (magnesium sulfate) and concentrated. The residue was purified by chromatography [100/0 to 60/40 dichloromethane/(8/1/1 dichloromethane/methanol/7 M ammonia in methanol) to provide the amidine in 51% yield.

tert-Butyl 6-(1-methyl-4,5-dihydro-1H-imidazol-2-yl)-1H-indazole-3-carboxylate (2.2 mmol) was diluted with trifluoroacetic acid (3.7 mL) and the reaction mixture was maintained for 16 h at rt. The precipitated product was isolated by filtration to provide the acid in 93% yield.

The following acid was prepared using this method:
6-(1-Methyl-4,5-dihydro-1H-imidazol-2-yl)-1H-indazole-3-carboxylic acid.

Example 7

Example 7 provides a preparation of fluorinated benzisothiazole-3-carboxlic acids from the ester of the corresponding benzisothiazole-3-carboxlic acid.

1-Fluoro-2,6-dichloropyridinium triflate (2.25 mmol) was added to a solution of ethyl 6-methoxy-1,2-benzisothiazole-3-carboxylate (1.87 mmol) in dichloromethane (20.0 mL) and the reaction mixture was maintained at rt for 6 h. The reaction mixture was filtered through silica gel (10 g, dichloromethane wash) and the eluent was concentrated. The residue was purified by chromatography 90/10 to 70/30 hexanes/ethyl acetate to provide the product in 22% yield.

A solution of ethyl 7-fluoro-6-methoxy-1,2-benzisothiazole-3-carboxylate (0.177 mmol) in ethanol (1.5 mL) was treated with a 5.0 M solution of sodium hydroxide (3.0 mmol). Within minutes, a gelatinous solid precipitated. The reaction mixture was diluted with water (50 mL) and was acidified with 6.0 N hydrochloric acid. The precipitate was collected by filtration to provide the product in 80% yield. The acid was used without further purification.

The following acid was prepared using this method:
7-Fluoro-6-methoxy-1,2-benzisothiazole-3-carboxylic acid.

Example 8

Example 8 provides a preparation of 5-azaindazole-3-carboxlic acid from 4-chloropyridine.

A saturated aqueous sodium bicarbonate solution was carefully added to a solution of 4-chloropyridine hydrochloride (56.7 mmol) in water (20 mL) until the solution was basic. The mixture was extracted with hexanes (3×25 mL). The combined organic layers were dried over magnesium sulfate and concentrated to a volume of ca. 25 mL to give a solution of the free base.

n-Butyllithium (2.0 M in pentane, 68 mmol) was added dropwise to a solution of N,N-diisopropylamine (62.3 mmol) in tetrahydrofuran (61.6 mmol) at 0° C. and the reaction mixture was maintained for 30 min. The reaction mixture was cooled to −78° C. and the hexanes solution of 4-chloropyridine was added dropwise and the mixture was maintained for 1 h. Diethyl oxalate (56.7 mmol) was added to the orange homogeneous solution and the mixture was allowed to warm to rt. Analysis by LC/MS revealed that the main product was not the ethyl oxalate, but the N,N-diisopropylamide. The reaction was partitioned between water (50 mL) and ethyl acetate (50 mL). The layers were separated and the organic washed with brine (25 mL), dried (magnesium sulfate), and concentrated. The residue was dissolved in ethanol (50.0 mL), treated with hydrazine (160 mmol) and the mixture was heated at reflux for 1 h. The reaction mixture was concentrated and the residue was titrated with dichloromethane to give 1.20 g (8.6%) of hydrazone product.

A mixture of N,N-diisopropyl-1H-pyrazolo[4,3-c]pyridine-3-carboxamide (0.800 g, 0.00325 mol) and aqueous hydrogen chloride (10 M, 3.00 mL) in a microwave reaction vessel was heated at 120° C. for 10 min. The mixture had to be heated on the high absorbance setting to avoid pressure buildup. The reaction was diluted with water and neutralized with sodium hydroxide (3 N). The resultant white precipitate was collected and found to be a mixture of the acid (47%) and the mono-isopropyl amide (25%). The mixture was used without further purification.

The following acid was prepared using this method:
1H-Pyrazolo[4,3-c]pyridine-3-carboxylic acid.

Example 9

Example 9 provides a method for the preparation of benzyloxy-substituted indazole-3-carboxylic acids and esters from the corresponding bromo nitrobenzenes.

Acetic anhydride (34 mL) and zinc dust (4.59 mmol) were added to a solution of 4-methoxynitrobenzene (230 mmol) in glacial acetic acid (34 mL) and the reaction mixture was heated at reflux for 0.5 h. The reaction mixture was poured into water (340 mL) and the pH of the solution was adjusted to 8 with 10% sodium hydroxide. The precipitated solids were isolated by filtration, washed with water (100 mL), and dried to provide the acetamide in 88% yield.

65% Nitric acid (22 mL) was added dropwise over 0.5 h to a solution of the acetamide (200 mmol) in dichloromethane (200 mL). The reaction mixture was maintained for 1 h at rt and was heated at reflux for 1 h. The reaction mixture was washed with water (200 mL), saturated sodium carbonate solution (100 mL), and water (200 mL). The combined organic layers were dried (magnesium sulfate) and concentrated to provide the nitro acetamide in 90% as a yellow solid.

The nitroacetamide (180 mmol) was added to 4 M sodium hydroxide (180 mL) and the reaction mixture was maintained for 2 h at 60° C. The precipitated solids were isolated by filtration, washed with water, and dried to provide the nitroaniline in 70% yield as a red solid.

A solution of sodium nitrite (11.8 g) in water (28 mL) was added dropwise over 0.5 h to a solution of the nitroaniline (125 mmol) in 40% hydrobromic acid (110 g) at 10° C. The reaction mixture was maintained for 40 min at 0-10° C. and was filtered. The filtrate was added dropwise over 1 h to a 0° C., purple solution of copper (I) bromide (209 mmol) in hydrobromic acid (74 mL). The reaction mixture was allowed to warm to and maintained at rt for 30 min, was maintained at 60° C. for 0.5 h, and was heated at reflux for 1 h. The reaction mixture was partitioned between water (2.0 L) and dichloromethane (600 mL) and the aqueous layer was further extracted with dichloromethane (300 mL). The combined organic layers were washed with 10% sodium hydroxide (200 mL), water (600 mL), 10% hydrochloric acid (300 mL), and water (600 mL), dried (magnesium sulfate) and concentrated to provide the nitrobromide in 83% yield as a yellow oil.

A solution of boron tribromide (250 mmol) in dichloromethane (200 mL) was added drop wise over 1 h to a solution of the nitrobromide (100 mmol) in dichloromethane (250 mL) at −78° C. The reaction mixture was allowed to warm to rt and was maintained for 30 h. The reaction mixture was cooled to 0° C., quenched with water (300 mL) and the aqueous layer was extracted with ethyl acetate (2×300 mL). The combined organic layers were washed with saturated sodium bicarbonate (2×300 mL), dried (magnesium sulfate), and concentrated to provide the nitrophenol in 87% yield as a brown crystalline solid.

Benzyl bromide (131 mmol) and potassium carbonate (130 mmol) were added to a solution of the nitrophenol (87.0 mmol) in 2/1 acetonitrile/acetone (840 mL). The reaction mixture was heated at reflux for 17 h and was concentrated to dryness. The residue was suspended in ethyl acetate (756 mL), filtered, and the organic layer was washed with water (567 mL), 1 M hydrochloric acid (2×567 mL), and brine (567 mL). The organic layer was dried (magnesium sulfate) and concentrated to the benzyl ether in 78% yield.

Diethyl malonate (890 mmol) was added drop wise over 1 h to a suspension of sodium hydride (520 mmol) in dimethylsulfoxide (100 mL) at 0° C. The benzyl ether (44.0 mmol) was added and the reaction mixture was heated at 100° C. for 5 h. The reaction mixture was poured into ice water and was extracted with ethyl acetate (3×70 mL). The combined organic layers were dried (magnesium sulfate) and concentrated to provide the diethylmalonate addition product. The diethylmalonate addition product was diluted with a 4 M solution of sodium hydroxide (100 mL) and the reaction mixture was heated at 60° C. for 6 h. The solution was extracted with dichloromethane (3×50 mL) and the aqueous layer was adjusted to pH 1 with concentrated hydrochloric acid. The reaction mixture was heated at 60° C. for 1 h, allowed to cool to rt, and was extracted with ethyl acetate (3×50 mL). The combined organic layers were dried (magnesium sulfate) and concentrated to provide the phenylacetic acid in 78% yield as a solid.

The phenylacetic acid (350 mmol) was added to a freshly prepared solution of ethanolic hydrochloric acid [acetyl chloride (5 mL) was added to ethanol (100 mL)] and the reaction mixture was heated at reflux for 20 h. The reaction mixture was concentrated to dryness and the residue was partitioned between saturated sodium bicarbonate (200 mL) and ethyl acetate (150 mL). The aqueous layer was extracted with ethyl acetate (2×50 mL) and the combined organic layers were dried (magnesium sulfate), filtered and concentrated to provide the ester in 77% yield.

The nitro ester (27.0 mmol) was dissolved in acetic acid (60 mL) and acetic anhydride (44 mL) and was cooled to 0° C. Zinc dust (153 mmol) was added and the reaction mixture was allowed to warm to rt and was maintained for 2 h. Additional quantities of zinc dust (2×45.9 mmol) were added during a 3 h course of time. After 1 h, the reaction mixture was filtered and the filter cake was washed with ethanol (100 mL). The combined filtrates were concentrated and the residue was partitioned between saturated sodium bicarbonate and ethyl acetate (50 mL). The solution was extracted with ethyl acetate (2×50 mL) and the combined organic layers were dried (magnesium sulfate), filtered and concentrated to provide the acetamide in 82% yield.

Isoamyl nitrite (47.2 g) was added dropwise over 30 min to a solution of the acetamide (21.0 mmol) in chloroform (80 mL) and acetic anhydride (45 mL). Solid potassium acetate (7.13 mmol) was added in several portions and the reaction mixture was heated at reflux for 1.5 h. The reaction mixture was washed with water (2×80 mL) and brine (80 mL), dried (magnesium sulfate), and concentrated to provide the acetylated indazole ester in 68% yield.

The acetylated indazole ester (15.0 mmol) was suspended in 2 M sodium hydroxide (35 mL) and the reaction mixture was heated at 60° C. for 24 h. The pH of the solution was adjusted to 1-2 with concentrated hydrochloric acid and the solids were collected by filtration and dried to provide 6-benzyloxy-1H-indazole-3-carboxylic acid in 28% yield as a yellow solid.

6-Benzyloxy-1H-indazole-3-carboxylic acid (1.85 mmol) was added to a freshly prepared solution of ethanolic hydrochloric acid [prepared from ethanol (20 mL) and acetyl chloride (5 mL)] and the reaction mixture was heated at reflux for 25 h and was concentrated. The residue was partitioned between saturated sodium bicarbonate (20 mL) and ethyl acetate (20 mL) and the layers were separated. The aqueous layer was extracted with ethyl acetate (2×20 mL) and the combined organic layers were dried (magnesium sulfate) and concentrated. The residue was purified by chromatography (300/1 dichloromethane/methanol) to provide the product in 36.4% yield. Alternatively, the ester can be obtained from the acetylated indazole ester by maintaining the acetylated material in 2 M ammonia in methanol for 30 min.

The following acids were prepared using this method:
6-Benzyloxy-1H-indazole-3-carboxylic acid.
5-Benzyloxy-1H-indazole-3-carboxylic acid (from 4-benzyloxy-2-bromonitrobenzene: see Parker, K. A.; Mindt, T. L. *Org. Lett.*, 2002, 4, 4265).
Ethyl 6-benzyloxy-1H-indazole-3-carboxylate.
Ethyl 5-benzyloxy-1H-indazole-3-carboxylate.

Example 10

Example 10 provides a method for the preparation of N-methoxyethoxymethyl and N-trimethylsilylethoxymethyl protected indazole acids and esters from the corresponding indazole esters using alkylation conditions.

Representative Procedure for N(1)-alkylation: A solution of ethyl 5-(benzyloxy)-1H-indazole-3-carboxylate (2.70 mmol) in tetrahydrofuran (10 mL) was added dropwise to a 0° C. suspension of sodium hydride (60% mineral oil dispersion, 8.1 mmol) in tetrahydrofuran (54.0 mL). The reaction was maintained at 0° C. for 1 h. [β-(Trimethylsilyl)ethoxy]methyl chloride (3.2 mmol) was added and the reaction mixture was maintained for 1 h. The reaction was partitioned between water (50 mL) and ethyl acetate (50 mL) and the organic layer was washed with brine (25 mL), dried (magnesium sulfate), and concentrated. The residue was purified by chromatography (95/5 to 85/15 hexanes/ethyl acetate to provide the protected indazole in 89% yield.

Representative Procedure for N(2)-alkylation: 2-Methoxyethoxy methyl chloride (48.0 mmol) was added slowly to a suspension of ethyl 6-bromo-1H-indazole-3-carboxylate (40.0 mmol) and N,N-diisopropylethylamine (80.0 mmol) in methylene chloride (80.0 mL). The reaction became homogeneous and was maintained for 4 h at rt. The reaction mixture was concentrated and the residue was partitioned between water (50 mL) and ethyl acetate (100 mL). The layers were separated and the organic layer was washed with brine (25 mL), dried (magnesium sulfate), and concentrated to give sufficiently pure product (89%) as a 2/1 mixture of N(2)- and N(1)-regioisomers as a yellow oil.

5.0 M of Sodium hydroxide (52 mL) was added to a solution of ethyl 6-bromo-1-[(2-methoxyethoxy)methyl]-1H-indazole-3-carboxylate (18.2 mmol) and the reaction mixture were maintained for 16 h. The solution was diluted with 50 mL water (50 mL) and acidified with 6.0 N hydrochloric acid. The slurry was extracted with ethyl acetate (50 mL) and the organic layer was washed with brine (25 mL), dried (magnesium sulfate), and concentrated. The residue was recrystalized from toluene to give a colorless solid (82%) as a mixture of regioisomers.

The following esters and acids were prepared using this method:
6-Bromo-1-[(2-methoxyethoxy)methyl]-1H-indazole-3-carboxylic acid.
Ethyl 6-bromo-1-[(2-methoxyethoxy)methyl]-1H-indazole-3-carboxylate.
Ethyl 6-benzyloxy-1-[(2-methoxyethoxy)methyl]-1H-indazole-3-carboxylate.
6-Bromo-1-{[2-(trimethylsilyl)ethoxy]methyl}-1H-indazole-3-carboxylic acid.
5-Bromo-1-{[2-(trimethylsilyl)ethoxy]methyl}-1H-indazole-3-carboxylic acid.
6-Bromo-2-{[2-(trimethylsilyl)ethoxy]methyl}-1H-indazole-3-carboxylic acid.
5-Bromo-2-{[2-(trimethylsilyl)ethoxy]methyl}-1H-indazole-3-carboxylic acid.
Ethyl 6-bromo-1-{[2-(trimethylsilyl)ethoxy]methyl}-1H-indazole-3-carboxylic acid.
Ethyl 6-bromo-2-{[2-(trimethylsilyl)ethoxy]methyl}-1H-indazole-3-carboxylic acid.
Ethyl 5-bromo-2-{[2-(trimethylsilyl)ethoxy]methyl}-1H-indazole-3-carboxylic acid.
Ethyl 5-bromo-1-{[2-(trimethylsilyl)ethoxy]methyl}-1H-indazole-3-carboxylic acid
Ethyl 6-benzyloxy-1-{[2-(trimethylsilyl)ethoxy]methyl}-1H-indazole-3-carboxylate.
Ethyl 5-benzyloxy-1-{[2-(trimethylsilyl)ethoxy]methyl}-1H-indazole-3-carboxylate.

Example 11

Example 11 provides a method for the preparation of alkoxy indazole acids from the corresponding benzyloxy indazole esters using Mitsunobu conditions.

Ethyl 6-benzyloxy-1-[(2-methoxyethoxy)methyl]-1H-indazole-3-carboxylate (9.38 mmol) was added to a suspension of 10% palladium on carbon (249 mg) in ethanol (66.7 mL). The reaction was shaken under an atmosphere of hydrogen (50 psi) for 4.0 h. The reaction was filtered through Celite and concentrated to give the phenol in 87% yield as a white solid.

Diisopropyl azodicarboxylate (0.841 mmol) was added dropwise to a solution of ethyl 6-hydroxy-1-[(2-methoxyethoxy)methyl]-1H-indazole-3-carboxylate (0.765 mmol), 1-methyl-3-pyrrolidinol (0.917 mmol), and triphenylphosphine (1.15 mmol) in tetrahydrofuran (4.6 mL). The reaction was maintained for 16 h and was concentrated. The residue was purified by chromatography (100/0 to 90/10 ethyl acetate/[70/30/2 ethyl acetate/methanol/dimethylethylamine] to provide the ether product in 28% yield. The ester was saponified to provide the acid which was coupled to the bicyclobase using Procedure A.

The following acids were prepared using this method:
Ethyl 6-hydroxy-1-{[2-(trimethylsilyl)ethoxy]methyl}-1H-indazole-3-carboxylate.
6-[(1-Methylpyrrolidin-3-yl)oxy]-1,2-benzisothiazole-3-carboxylic acid.
6-(1-Azabicyclo[2.2.2]oct-3-yloxy)-1,2-benzisothiazole-3-carboxylic acid
3-(1,4-Diazabicyclo[3.2.2]non-4-ylcarbonyl)-5-(tetrahydro-2H-pyran-3-yloxy)-1-{[2-(trimethylsilyl)ethoxy]methyl}-1H-indazole.
3-(1,4-Diazabicyclo[3.2.2]non-4-ylcarbonyl)-6-(tetrahydro-2H-pyran-4-yloxy)-1-{[2-(trimethylsilyl)ethoxy]methyl}-1H-indazole.
3-(1,4-Diazabicyclo[3.2.2]non-4-ylcarbonyl)-6-(tetrahydro-2H-pyran-3-yloxy)-1-{[2-(trimethylsilyl)ethoxy]methyl}-1H-indazole.

Example 12

Example 12 provides a preparation of aminobenzisothiazole-3-carboxlic acids from the ester.

Cesium carbonate (3.18 mmol), palladium(II) acetate (0.24 mmol), and 2-dicyclohexylphosphino-2',4',6'-tri-i-propyl-1,1'-biphenyl (0.24 mmol) were combined in a microwave vessel and the vessel was flushed with nitrogen. A solution of (R)-(+)-3-pyrrolidinol (3.18 mol) and tert-butyl 6-bromo-1,2-benzisothiazole-3-carboxylate (1.59 mol) in tetrahydrofuran (20.0 mL) was added. The vessel was sealed and was heated at 135° C. for 30 minutes. The reaction mixture was filtered through Celite (ethyl acetate) and the filtrate was concentrated. The residue was purified by chromatography (70/30 to 50/50 hexanes/ethyl acetate) to provide the purified ester. The ester was dissolved in dichloromethane/trifluoroacetic acid (4:1, 2.00 mL) and was maintained for 16 h. The reaction mixture was concentrated to provide the product in 23% yield. The product was used without further purification.

Alternatively, when ethyl 6-bromo-1,2-benzisothiazole-3-carboxylate was used, a solution of the ester in ethanol was saponified using 5N sodium hydroxide. The acid was collected by filtration after diluting with water and neutralizing with acetic acid.

The following acids and esters were prepared using this method:
6-[(3R)-3-Methoxypyrrolidin-1-yl]-1,2-benzisothiazole-3-carboxylic acid.
6-[(3S)-3-Methoxypyrrolidin-1-yl]-1,2-benzisothiazole-3-carboxylic acid.
6-(3-Methoxypyrrolidin-1-yl)-1,2-benzisothiazole-3-carboxylic acid.
5-[(3S)-3-Methoxypyrrolidin-1-yl]-1-{[2-(trimethylsilyl)ethoxy]methyl}-1H-indazole-3-carboxylic acid.
5-[(3R)-3-Methoxypyrrolidin-1-yl]-1-{[2-(trimethylsilyl)ethoxy]methyl}-1H-indazole-3-carboxylic acid.

6-[(3S)-3-Methoxypyrrolidin-1-yl]-1-{[2-(trimethylsilyl)ethoxy]methyl}-1H-indazole-3-carboxylic acid.
6-[(3R)-3-Methoxypyrrolidin-1-yl]-1-{[2-(trimethylsilyl)ethoxy]methyl}-1H-indazole-3-carboxylic acid.
6-[(1S,4S)-5-(tert-Butoxycarbonyl)-2,5-diazabicyclo[2.2.1]hept-2-yl]-1,2-benzisothiazole-3-carboxylic acid
6-[(1S,4S)-5-Methyl-2,5-diazabicyclo[2.2.1]hept-2-yl]-1,2-benzisothiazole-3-carboxylic acid.
6-[(1R,4R)-5-Methyl-2,5-diazabicyclo[2.2.1]hept-2-yl]-1,2-benzisothiazole-3-carboxylic acid.
6-(1,4-Diazabicyclo[3.2.2]non-4-yl)-1,2-benzisothiazole-3-carboxylic acid.
6-(Pyrrolidin-1-yl)-1,2-benzisothiazole-3-carboxylic acid.
6-(4-Methylpiperazin-1-yl)-1,2-benzisothiazole-3-carboxylic acid.
6-(4-Methyl-1,4-diazepan-1-yl)-1,2-benzisothiazole-3-carboxylic acid.
6-(Hexahydropyrrolo[1,2-a]pyrazin-2(1H)-yl)-1,2-benzisothiazole-3-carboxylic acid.
6-(5-Methyl-2,5-diazabicyclo[2.2.2]oct-2-yl)-1,2-benzisothiazole-3-carboxylic acid.

The following esters were prepared from the N-Boc intermediates using trifluoroacetic acid:
Ethyl 6-[(1S,4S)-2,5-diazabicyclo[2.2.1]hept-2-yl]-1,2-benzisothiazole-3-carboxylate
Ethyl 5-(1,4-diazepan-1-yl)-1H-indazole-3-carboxylate.

Example 13

Example 13 provides a preparation of 6-phenyl-1H-pyrazolo[3,4-b]pyridine-3-carboxylic acid from tert-butyl 6-phenyl-1H-pyrazolo[3,4-b]pyridine-3-carboxylate.

[1,3-Bis(diphenylphosphino)propane]nickel(II) chloride (0.0999 mmol) and tert-butyl 6-fluoro-1H-pyrazolo[3,4-b]pyridine-3-carboxylate (0.999 mmol) were dissolved in tetrahydrofuran (20.0 mL) and the reaction mixture was cooled to 0° C. A 1.00 M solution of phenylmagnesium bromide in tetrahydrofuran (2.40 mL) was added and the reaction mixture was allowed to warm to rt and was maintained for 4 h. The reaction was partitioned between water (50 mL) and ethyl acetate (50 mL). The layers were separated and the organic washed with brine (25 mL), dried (magnesium sulfate), and concentrated. The residue was purified by chromatography (95/5 to 85/15 hexanes/ethyl acetate) to provide the product in 56% yield.

tert-Butyl 6-phenyl-1H-pyrazolo[3,4-b]pyridine-3-carboxylate (0.555 mmol) was dissolved in a 4/1 dichloromethane/trifluoroacetic acid solution (2.00 mL) and the reaction was maintained for 16 h at rt. The reaction mixture was concentrated and the residue was diluted with water (5 mL). The reaction mixture was neutralized to pH 5-7, stirred vigorously for 1 h, and the precipitated solids were collected by filtration to provide the acid in 92% yield.

The following acid was prepared using this method:
6-Phenyl-1H-pyrazolo[3,4-b]pyridine-3-carboxylic acid.

Example 14

Example 14 provides a method for the preparation of 2,2,2-trifluoroethyl substituted acids.

2,2,2-Trifluoroethylmethanesulfonate (0.330 mmol) was added to a solution of ethyl 5-(1,4-diazepan-1-yl)-1H-indazole-3-carboxylate (0.165 mmol) in N,N-diisopropylethylamine (0.20 mL) and acetonitrile (15 mL) and the resulting mixture was maintained for 16 h at room temperature. The reaction mixture was concentrated and the residue was purified by chromatography (90/10 to 70/30 hexanes/ethyl acetate) to yield the purified ester. The ester was dissolved in ethanol (5.0 mL) and an aqueous solution of sodium hydroxide (5.0 M, 2.0 mL) was added. The reaction was maintained at room temperature for 4 h, then diluted with water (50 mL) and neutralized with acetic acid. The precipitate was collected by filtration to provide trifluoroethylamino acid in 78% yield.

The following acid was prepared using this procedure:
5-[4-(2,2,2-Trifluoroethyl)-1,4-diazepan-1-yl]-1H-indazole-3-carboxylic acid Example 15

Example 15 provides a preparation of N-alkyl aminobenzisothiazole-3-carboxylic acids from the corresponding aminobenzisothiazole-3-carboxylic esters.

Sodium cyanoborohydride (8.57 mmol) was added to a solution of ethyl 6-[(1S,4S)-2,5-diazabicyclo[2.2.1]hept-2-yl]-1,2-benzisothiazole-3-carboxylate (0.260 g, 0.857 mmol) and 1-ethoxy-1-(trimethylsilyloxy)cyclopropane (8.57 mmol) in ethanol (11.2 mL) and the reaction mixture was heated at 60° C. for 6 h. The reaction mixture was diluted with water (50 mL) and was extracted with ethyl acetate (2×50 mL). The combined organic layers were washed with brine (25 mL), dried (magnesium sulfate), and were concentrated. The residue was purified by chromatography (ethyl acetate) to yield the ester. A 5.0 M solution of sodium hydroxide in water (4.00 mL) was added to a solution of the ester in ethanol (10.0 mL) and the reaction mixture was maintained for 16 h. The reaction was neutralized with acetic acid and was loaded onto a SCX column. The column was flushed with water (200 mL) and methanol (100 mL) and the product was eluted with 2.0 M ammonia in methanol (60 mL) to provide the acid in 56% yield. The acid was used without further purification.

The following acid was prepared using this method:
6-[(1S,4S)-5-Cyclopropyl-2,5-diazabicyclo[2.2.1]hept-2-yl]-1,2-benzisothiazole-3-carboxylic acid.

Example 16

Example 16 provides a preparation of N-alkyl aminobenzisothiazole-3-carboxylic acids from the corresponding aminobenzisothiazole-3-carboxylic esters.

Cyclopropylmethyl bromide (1.71 mmol) was added to a suspension of ethyl 6-[(1S,4S)-2,5-diazabicyclo[2.2.1]hept-2-yl]-1,2-benzisothiazole-3-carboxylate (0.857 mmol) and sodium bicarbonate (3.43 mmol) in acetonitrile (10.0 mL) and the reaction mixture was heated at 60° C. for 6 h. The acetonitrile was decanted from the solids and the solids were washed with acetonitrile (2×5 mL). The acetonitrile solution was transferred to a silica gel column and the mixture was purified by chromatography {9/1 to 7/3 ethyl acetate/[(50/50/2) ethyl acetate/methanol/dimethylethylamine]} to yield the purified ester. A 5.0 M solution of sodium hydroxide in water (2.00 mL) was added to a solution of the ester in ethanol (5.0 mL) and the reaction mixture was maintained for 16 h. The reaction was neutralized with acetic acid and the reaction mixture was transferred to a SCX column (10 g). The column was flushed with water (200 mL) and methanol (100 mL) and the product was eluted with 2.0 M ammonia in methanol to provide the product in 50% yield. The acid was used without further purification.

The following acid was prepared using this method:
6-[(1S,4S)-5-(Cyclopropylmethyl)-2,5-diazabicyclo[2.2.1]hept-2-yl]-1,2-benzisothiazole-3-carboxylic acid.

Example 17

Example 17 provides a method for the preparation of cyclic ureas from diamines.

Carbonic acid, dimethyl ester (10.0 mmol) was added dropwise to a mixture of N-propyl-1,2-ethanediamine (10.0 mmol) and cesium carbonate (2.00 mmol) and the reaction mixture was heated at 70° C. for 1 h. The reaction mixture was concentrated and the residue was heated at 130° C. for 3 h. The reaction mixture was concentrated and the residue was purified by chromatography [(50/50 to 0/100) hexane/ethyl acetate] to provide the product (60%) as an oil.

The following cyclic urea was prepared using this method: 1-Propylimidazolidin-2-one.

Example 18

Example 18 provides a method for the preparation of 3-alkoxypyrrolidines from N-Boc-3-hydroxypyrrolidine. 1-Boc-3-hydroxypyrrolidine (16.1 mmol) was added in portions to a suspension of sodium hydride (22.0 mmol) in tetrahydrofuran (40 mL) at 0° C. The reaction mixture was diluted with tetrahydrofuran (60 mL) and allowed to warm to rt. Methyl iodide (21.0 mmol) was added to the cloudy suspension after 1 h and the reaction mixture was maintained at rt for 6 h. The reaction mixture was concentrated and re-dissolved in ethyl acetate (100 mL). The extract was washed with saturated ammonium chloride (20 mL), water (20 mL), and brine (20 mL) and was dried (sodium sulfate). The residue was purified by chromatography (¼ ethyl acetate/hexane) to give the ether. The N-Boc product was dissolved in tetrahydrofuran (30 mL) and 6 N hydrochloric acid (20 mL) was added. The resultant mixture was stirred for 1 h and was concentrated to give an oil. Toluene (10 mL) and ethanol (10 mL) were added and the mixture was concentrated to give 1.79 g of brownish, very hygroscopic solid. The solid was suspended in ethyl acetate and stirred vigorously for 12 h. The solids were quickly collected by filtration and dried under high vacuum to give the product (81%) as a colorless solid.

An alternative procedure used for the removal of the N-Boc groups entails exposure to trifluoroacetic acid for 4 h. followed by concentration of the reaction mixture. This procedure may be useful for the production of the amine as a free base.

The following amine was prepared using this procedure: 3-Methoxypyrrolidine hydrochloride.

The free base was obtained by neutralization of the salt residue with saturated sodium carbonate (5 mL), extraction with 9/1 dichloromethane/methanol (3×20 mL), drying (potassium carbonate), and concentration, followed by capturing the amine on a SCX column and eulting with 2M ammonia in methanol:
3-Methoxypyrrolidine.
(3R)-3-Methoxypyrrolidine.
(3S)-3-Methoxypyrrolidine.
II. Coupling and Derivatization Procedures
Representative Procedure A.

Procedure A provides a method for the coupling between bicyclobases and carboxylic acids to form carboxamide derivatives.

1,4-Diazabicyclo[3.2.2]nonane (0.54 mmol), N,N,N',N'-tetramethyl-O-(7-aza benzotriazol-1-yl)uronium hexafluorophosphate (HATU) (0.58 mmol) and N,N-diisopropyl ethylamine (0.2 mL) were added to a solution of 5-methoxy-1,2-benzisothiazole-3-carboxylic acid (0.4 mmol) in tetrahydrofuran (15 mL), and the reaction was maintained for 10 h. The reaction mixture was concentrated in vacuo, and the resulting residue was loaded on a SCX column, washed with methanol (100 mL) and the product was eluted using a 7 N solution of ammonia in methanol (100 mL). The residue was purified by preparative HPLC to provide the product in 50% yield.

Note: O-(Benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), and carbonyl diimidazole (CDI) were found to be suitable alternative coupling agents and were also used to produce the amide products using the above procedure. N,N-Dimethylformamide was used instead of tetrahydrofuran for the coupling with indazole acids.

Using this general procedure the following compounds were prepared:

9) 3-(1,4-Diazabicyclo[3.2.2]non-4-ylcarbonyl)-5-methoxy-1,2-benzisothiazole hydroformate, $^1$H NMR (CD$_3$OD) δ 8.45 (br, 1H), 7.95 (m, 1H), 7.64 (s, 1H), 7.28 (m, 1H), 5.05 (m, 0.7H), 4.52 (m, 0.3H), 4.28 (m, 0.6H), 4.10 (m, 1.4H), 3.90 (s, 3H), 3.7-3.4 (m, 6H), 2.40 (m, 2H), 2.20 (m, 2H); LC/MS (EI) $t_R$ 2.79 min (Method A), m/z 318 (M$^+$+1).

10) 3-(1,4-Diazabicyclo[3.2.2]non-4-ylcarbonyl)-6-fluoro-1H-pyrazolo[3,4-b]pyridine hydroformate, LC/MS (EI) $t_R$ 2.59 min (Method A), m/z 290 (M$^+$+1).

18) 3-(1,4-Diazabicyclo[3.2.2]non-4-ylcarbonyl)-6-[(3R)-3-methoxypyrrolidin-1-yl]-1,2-benzisothiazole, LC/MS (EI) $t_R$ 3.54 min (Method C), m/z 387 (M$^+$+1).

19) 3-(1,4-Diazabicyclo[3.2.2]non-4-ylcarbonyl)-7-fluoro-6-methoxy-1,2-benzisothiazole, LC/MS (EI) $t_R$ 3.30 min (Method C), m/z 336 (M$^+$+1).

20) 3-(1,4-Diazabicyclo[3.2.2]non-4-ylcarbonyl)-6-[(3S)-3-methoxypyrrolidin-1-yl]-1,2-benzisothiazole, LC/MS (EI) $t_R$ 3.50 min (Method C), m/z 387 (M$^+$+1).

22) 3-(1,4-Diazabicyclo[3.2.2]non-4-ylcarbonyl)-1-ethyl-6-methoxy-1H-indazole, LC/MS (EI) $t_R$ 2.92 min (Method C), m/z 329 (M$^+$+1).

23) 3-(1,4-Diazabicyclo[3.2.2]non-4-ylcarbonyl)-1H-pyrazolo[4,3-c]pyridine, LC/MS (EI) $t_R$ 1.29 min (Method B), m/z 272 (M$^+$+1).

24) 3-(1,4-Diazabicyclo[3.2.2]non-4-ylcarbonyl)-6-phenyl-1H-pyrazolo[3,4-b]pyridine, LC/MS (EI) $t_R$ 3.99 min (Method C), m/z 348 (M$^+$+1).

25) 3-(1,4-Diazabicyclo[3.2.2]non-4-ylcarbonyl)-6-[(1S,4S)-5-methyl-2,5-diazabicyclo[2.2.1]hept-2-yl]-1,2-benzisothiazole, LC/MS (EI) $t_R$ 1.60 min (Method B), m/z 398 (M$^+$+1).

26) 3-(1,4-Diazabicyclo[3.2.2]non-4-ylcarbonyl)-6-[(1R,4R)-5-methyl-2,5-diazabicyclo[2.2.1]hept-2-yl]-1,2-benzisothiazole, LC/MS (EI) $t_R$ 3.13 min (Method D), m/z 398 (M$^+$+1).

27) 6-(1,4-Diazabicyclo[3.2.2]non-4-yl)-3-(1,4-diazabicyclo[3.2.2]non-4-ylcarbonyl)-1,2-benzisothiazole, LC/MS (EI) $t_R$ 3.15 min (Method D), m/z 412 (M$^+$+1).

28) 3-(1,4-Diazabicyclo[3.2.2]non-4-ylcarbonyl)-5-[4-(2,2,2-trifluoroethyl)-1,4-diazepan-1-yl]-1H-indazole, LC/MS (EI) $t_R$ 4.26 min (Method D), m/z 451 (M$^+$+1).

29) 3-(1,4-Diazabicyclo[3.2.2]non-4-ylcarbonyl)-6-pyrrolidin-1-yl-1,2-benzisothiazole, LC/MS (EI) $t_R$ 4.48 min (Method B), m/z 357 (M$^+$+1).

30) 3-(1,4-Diazabicyclo[3.2.2]non-4-ylcarbonyl)-6-(4-methylpiperazin-1-yl)-1,2-benzisothiazole, LC/MS (EI) $t_R$ 1.42 min (Method B), m/z 386 (M$^+$+1).

31) 3-(1,4-Diazabicyclo[3.2.2]non-4-ylcarbonyl)-6-(4-methyl-1,4-diazepan-1-yl)-1,2-benzisothiazole, LC/MS (EI) $t_R$ 1.51 min (Method B), m/z 400 (M$^+$+1).

32) 3-(1,4-Diazabicyclo[3.2.2]non-4-ylcarbonyl)-6-(hexahydropyrrolo[1,2-a]pyrazin-2(1H)-yl)-1,2-benzisothiazole, LC/MS (EI) $t_R$ 1.57 min (Method B), m/z 412 (M$^+$+1).

33) 3-(1,4-Diazabicyclo[3.2.2]non-4-ylcarbonyl)-6-(5-methyl-2,5-diazabicyclo[2.2.2]oct-2-yl)-1,2-benzisothiazole, LC/MS (EI) $t_R$ 1.54 min (Method B), m/z 412 (M$^+$+1).

34) 6-[(1S,4S)-5-cyclopropyl-2,5-diazabicyclo[2.2.1]hept-2-yl]-3-(1,4-diazabicyclo[3.2.2]non-4-ylcarbonyl)-1,2-benzisothiazole, LC/MS (EI) $t_R$ 1.27 min (Method C), m/z 424 (M$^+$+1).

35) 6-[(1S,4S)-5-(cyclopropylmethyl)-2,5-diazabicyclo[2.2.1]hept-2-yl]-3-(1,4-diazabicyclo[3.2.2]non-4-ylcarbonyl)-1,2-benzisothiazole, LC/MS (EI) $t_R$ 1.29 min (Method C), m/z 438 (M$^+$+1).

36) tert-Butyl (1S,4S)-5-[3-(1,4-diazabicyclo[3.2.2]non-4-ylcarbonyl)-1,2-benzisothiazol-6-yl]-2,5-diazabicyclo[2.2.1]heptane-2-carboxylate, LC/MS (EI) $t_R$ 3.96 min (Method C), m/z 484 (M$^+$+1).

38) 3-(1,4-Diazabicyclo[3.2.2]non-4-ylcarbonyl)-6-[(1-methylpyrrolidin-3-yl)oxy]-1,2-benzisothiazole, LC/MS (EI) $t_R$ 1.25 min (Method C), m/z 387 (M$^+$+1).

39) 6-(1-Azabicyclo[2.2.2]oct-3-yloxy)-3-(1,4-diazabicyclo[3.2.2]non-4-ylcarbonyl)-1,2-benzisothiazole, LC/MS (EI) $t_R$ 1.29 min (Method C), m/z 413 (M$^+$+1).

40) 6-(Benzyloxy)-3-(1,4-diazabicyclo[3.2.2]non-4-ylcarbonyl)-1H-indazole, LC/MS (EI) $t_R$ 3.82 min (Method C), m/z 377 (M$^+$+1).

41) 3-(1,4-Diazabicyclo[3.2.2]non-4-ylcarbonyl)-6-(1-methyl-4,5-dihydro-1H-imidazol-2-yl)-1H-indazole, LC/MS (EI) $t_R$ 1.26 min (Method C), m/z 352 (M$^+$+1).

6-Bromo-3-(1,4-diazabicyclo[3.2.2]non-4-ylcarbonyl)-1-{[2-(trimethylsilyl)ethoxy]methyl}-1H-indazole.

The following compounds were prepared using this general procedure followed by removal of the protecting group using N,N,N,N-tetrabutylammonium fluoride (TBAF) and purification by preparative HPLC. The free base form was obtained by ion exchange:

11) 3-(1,4-Diazabicyclo[3.2.2]non-4-ylcarbonyl)-6-[(3R)-3-methoxypyrrolidin-1-yl]-1H-indazole dihydroformate, LC/MS (EI) $t_R$ 2.81 min (Method C), m/z 369 (M$^+$+1).

12) 3-(1,4-Diazabicyclo[3.2.2]non-4-ylcarbonyl)-5-[(3S)-3-methoxypyrrolidin-1-yl]-1H-indazole dihydroformate, LC/MS (EI) $t_R$ 2.80 min (Method C), m/z 369 (M$^+$+1).

13) 3-(1,4-Diazabicyclo[3.2.2]non-4-ylcarbonyl)-5-[(3R)-3-methoxypyrrolidin-1-yl]-1H-indazole dihydroformate, LC/MS (EI) $t_R$ 2.80 min (Method C), m/z 369 (M$^+$+1).

14) 3-(1,4-Diazabicyclo[3.2.2]non-4-ylcarbonyl)-6-[(3S)-3-methoxypyrrolidin-1-yl]-1H-indazole dihydroformate, LC/MS (EI) $t_R$ 2.84 min (Method C), m/z 369 (M$^+$+1).

15) 3-(1,4-Diazabicyclo[3.2.2]non-4-ylcarbonyl)-5-(tetrahydro-2H-pyran-3-yloxy)-1H-indazole, LC/MS (EI) $t_R$ 2.91 min (Method C), m/z 371 (M$^+$+1).

16) 3-(1,4-Diazabicyclo[3.2.2]non-4-ylcarbonyl)-6-(tetrahydro-2H-pyran-4-yloxy)-1H-indazole, LC/MS (EI) $t_R$ 2.92 min (Method C), m/z 371 (M$^+$+1).

17) 3-(1,4-Diazabicyclo[3.2.2]non-4-ylcarbonyl)-6-(tetrahydro-2H-pyran-3-yloxy)-1H-indazole, LC/MS (EI) $t_R$ 2.93 min (Method C), m/z 371 (M$^+$+1).

The following compounds were prepared using this general procedure followed by removal of the protecting group using trifluoroacetic acid (TFA) and purification by ion exchange:

37) 6-[(1S,4S)-2,5-Diazabicyclo[2.2.1]hept-2-yl]-3-(1,4-diazabicyclo[3.2.2]non-4-ylcarbonyl)-1,2-benzisothiazole, LC/MS (EI) $t_R$ 1.26 min (Method C), m/z 384 (M$^+$+1).

Representative Procedure B.

Procedure B provides a method for the coupling between brominated bicyclobase carboxamides and cyclic amines to form amine derivatives.

A solution of 6-bromo-3-(1,4-diazabicyclo[3.2.2]non-4-ylcarbonyl)-1-{[2-(trimethylsilyl)ethoxy]methyl}-1H-indazole (0.469 mmol) in toluene (3.97 mL) was added to a mixture of 2-dicyclohexylphospino-2',4',6'-tri-isopropyl-1,1'-biphenyl (0.0282 mmol), palladium (II) acetate (0.009 mmol), cesium carbonate (1.41 mmol) and 1-methylpiperazine (1.41 mmol) and the reaction was heated at 80° C. for 3 d. The inorganic precipitate was removed by filtration and the reaction mixture was concentrated. The residue was purified by chromatography [100/0 to 80/20 ethyl acetate/(50:50:2) ethyl acetate/methanol/dimethylethylamine] to provide an oil. The residue was diluted with tetrahydrofuran (6 mL) and 6 N hydrochloric acid (4 mL) and the mixture was maintained for 1 h. The reaction mixture was concentrated and purified by preparative HPLC [90/10 to 50/50 water (0.1% formic acid)/acetonitrile (0.1% formic acid, 10 min. gradient]. The product fractions were loaded onto a SCX column (10 g) and washed with 5 volumes of methanol, and the product was eluted using 2.0 M ammonia in methanol. The residue was further purified by chromatography [75/25 to 60/40 ethyl acetate/(50:50/2) ethyl acetate/methanol/dimethylethylamine] to afford the product in 2.3% yield.

Using this general procedure the following compounds were prepared:

7) 3-(1,4-Diazabicyclo[3.2.2]non-4-ylcarbonyl)-6-(4-methylpiperazin-1-yl)-1H-indazole, $^1$H NMR (CD$_3$OD) δ 7.76 (m, 1H), 7.07 (m, 1H), 6.90 (s, 1H), 4.80 (m, 1H), 4.17 (m, 1.4H), 4.05 (m, 0.6H), 3.27 (m, 2H), 3.2-3.0 (m, 6H), 2.67 (m, 2H), 2.38 (s, 3H), 2.20 (m, 2H), 1.90 (m, 2H); LC/MS (EI) $t_R$ 1.27 min (Method C), m/z 369 (M$^+$+1).

1) 3-(1,4-Diazabicyclo[3.2.2]non-4-ylcarbonyl)-6-pyrrolidin-1-yl-1H-indazole, LC/MS (EI) $t_R$ 4.10 min (Method C), m/z 340 (M$^+$+1).

2) 3-(1,4-Diazabicyclo[3.2.2]non-4-ylcarbonyl)-6-(3-methoxypyrrolidin-1-yl)-1H-indazole, LC/MS (EI) $t_R$ 3.94 min (Method C), m/z 370 (M$^+$+1).

3) 3-(1,4-Diazabicyclo[3.2.2]non-4-ylcarbonyl)-6-morpholin-4-yl-1H-indazole, LC/MS (EI) $t_R$ 3.51 min (Method C), m/z 356 (M$^+$+1).

5) 3-(1,4-Diazabicyclo[3.2.2]non-4-ylcarbonyl)-6-(4-methyl-1,4-diazepan-1-yl)-1H-indazole, LC/MS (EI) $t_R$ 1.38 min (Method C), m/z 383 (M$^+$+1).

6) 3-(1,4-Diazabicyclo[3.2.2]non-4-ylcarbonyl)-6-thiomorpholin-4-yl-1H-indazole, LC/MS (EI) $t_R$ 3.99 min (Method C), m/z 372 (M$^+$+1).

8) 3-(1,4-Diazabicyclo[3.2.2]non-4-ylcarbonyl)-6-(1,4-oxazepan-4-yl)-1H-indazole, LC/MS (EI) $t_R$ 3.73 min (Method B), m/z 370 (M$^+$+1).

Representative Procedure C.

Procedure C provides a method for the reaction between brominated bicyclobase carboxamides and cyclic ureas to form cyclic urea derivatives.

A solution of 6-bromo-3-(1,4-diazabicyclo[3.2.2]non-4-ylcarbonyl)-1-{[2-(trimethylsilyl)ethoxy]methyl}-1H-indazole (0.469 mmol) in toluene (3.97 mL) was added to a mixture of 2-dicyclohexylphospino-2',4',6'-tri-isopropyl-1,1'-biphenyl (0.0282 mmol), palladium (II) acetate (0.009 mmol), cesium carbonate (1.41 mmol) and 1-propylimidazolidin-2-one (1.41 mmol) and the reaction was heated at 80° C. for 3 d. The inorganic precipitate was removed by filtration and the reaction mixture was concentrated. The residue was purified by chromatography [100/0 to 80/20 ethyl acetate/(50:50:2) ethyl acetate/methanol/dimethylethylamine] to provide an oil. The residue was dissolved in tetrahydrofuran (6 mL) and 6 N hydrochloric acid (4 mL) and the mixture was maintained for 1 h. The reaction mixture was concentrated and purified by preparative HPLC [90/10 to 50/50 water (0.1% formic acid)/acetonitrile (0.1% formic acid, 10 min. gradient]. The product fractions were loaded onto a SCX column (10 g) and washed with 5 volumes of methanol, and the product was eluted using 2.0 M ammonia in methanol. The residue was further purified by chromatography [75/25 to 60/40 ethyl acetate/(50/50/2) ethyl acetate/methanol/dimethylethylamine] to afford the product in 25% yield.

Using this general procedure the following compounds were prepared:

4) 1-[3-(1,4-Diazabicyclo[3.2.2]non-4-ylcarbonyl)-1H-indazol-6-yl]-3-propylimidazolidin-2-one, $^1$H NMR (CD$_3$OD) δ 7.90 (m, 1H), 7.71 (s, 1H), 7.53 (m, 1H), 4.95 (m, 0.3H), 4.80 (m, 0.7H), 4.19 (m, 1.4H), 4.05 (m, 0.6H), 3.96 (m, 2H), 3.55 (m, 2H), 3.26 (t, J=7.3, 2H), 3.2-3.0 (m, 6H), 2.20 (m, 2H), 1.90 (m, 2H), 1.62 (m, J=7.3, 2H), 0.96 (t, J=7.3, 3H); LC/MS (EI) $t_R$ 4.09 min (Method B), m/z 397 (M$^+$+1).

Representative Procedure D.

Procedure D provides a method for the transformation of brominated bicyclobase carboxamides to anilines and the subsequent reaction with isocyanates to form urea derivatives.

The solid mixture of 6-bromo-3-(1,4-diazabicyclo[3.2.2]non-4-ylcarbonyl)-1-methyl-1H-indazole (1.10 mmol), palladium acetate (0.207 mmol), cesium carbonate (2.20 mmol), and 9,9-dimethyl-4,5-bis(diphenylphosphino)xanthene (0.112 mol) in a microwave reactor vessel was evacuated and placed under an atmosphere of nitrogen. Tetrahydrofuran (6.7 mL) and benzophenone imine (1.10 mmol) were added and the vessel was sealed and heated at 140° C. for 600 sec. The reaction mixture was filtered and purified by chromatography [9/1 to 7/3 ethyl acetate/(50:50:5) ethyl acetate/methanol/dimethylethylamine] to yield the purified imine product. The imine was dissolved in tetrahydrofuran (6 mL), treated with 3 N hydrochloric acid (2 mL), and maintained for 60 min at rt. The mixture was loaded onto a SCX column (10 g) and flushed with 5 volumes of methanol. The product (81% yield) was eluted using 2.0 M ammonia in methanol.

Propyl isocyanate (0.217 mmol) was added to a solution of 3-(1,4-diazabicyclo[3.2.2]non-4-ylcarbonyl)-1-methyl-1H-indazol-6-amine (0.167 mmol) in a mixture of pyridine (2 mL) and N,N-dimethylformamide (0.9 mL) and the reaction mixture was maintained for 16 h at rt. The reaction mixture was transferred to an ISCO column and was purified by chromatography [100/0 to 85/15 ethyl acetate/(1:1:0.1) ethyl acetate/methanol/dimethylethylamine] to yield a slightly impure product as a white solid. The mixture was further purified by preparative HPLC to yield the product in 5% yield as a white solid.

Using this general procedure the following compounds were prepared:

3-(1,4-Diazabicyclo[3.2.2]non-4-ylcarbonyl)-1-methyl-1H-indazol-6-amine.

21) N-[3-(1,4-Diazabicyclo[3.2.2]non-4-ylcarbonyl)-1-methyl-1H-indazol-6-yl]-N'-propylurea hydroformate, $^1$H NMR (CD$_3$OD) δ 8.45 (br, 1H), 7.93 (s, 1H), 7.88 (m, 1H), 7.00 (m, 1H), 5.35 (m, 0.3H), 4.95 (m, 0.7H), 4.62 (m, 1.4H), 4.20 (m, 0.6H), 4.05 (s, 3H), 3.7-3.4 (m, 6H), 3.20 (t, J=7.1 Hz, 2H), 2.40 (m, 2H), 2.20 (m, 2H), 1.58 (m, J=7.1 Hz, 2H), 0.98 (t, J=7.3 Hz, 3H); LC/MS (EI) $t_R$ 2.77 min (Method C), m/z 385 (M$^+$+1).

[$^3$H] MLA Binding

Materials:

Rat Brain: Pel-Freez Biologicals, CAT No. 56004-2

Protease inhibitor cocktail tablet: Roche, CAT No. 1697498

Membrane Preparation

Rat brains in 20 vol (w/v) of ice-cold 0.32 M sucrose with protease inhibitors (one tablet per 50 ml,) were homogenized with a polytron for 10 sec at setting 11, then centrifuged 10 min at 1000 g, 4° C. The supernatant was centrifuged again for 20 min at 20,000 g, 4° C. The pellets were resuspended in binding buffer (200 mM TRIS-HCl, 20 mM HEPES, pH 7.5, 144 mM NaCl, 1.5 mM KCl, 1 mM MgSO$_4$, 2 mM CaCl$_2$, 0.1% (w/v) BSA) and stored membrane prep at −80° C.

For saturation assay, the 200 µl assay mixture in binding buffer contains 200 µg of membrane protein, 0.2 to 44 nM of [$^3$H] MLA. The nonspecific binding was defined using 1 µM MLA. Competition assay was carried out with 2 nM [$^3$H] MLA and a desirable range of compounds. The assay mixture was incubated at 22° C. for 2 hours, then harvested with GF/B filter presoaked with 0.3% PEI in binding buffer using Tomtec harvester. The filter was washed three times with binding buffer and the radioactivity was counted with Trilux.

Binding affinities for the preferred compounds of the invention were 13 nM to 1.5 µM.

The preceding examples can be repeated with similar success by substituting the generically or specifically described reactants and/or operating conditions of this invention for those used in the preceding examples.

While the invention has been illustrated with respect to the production of particular compounds, it is readily apparent to those of ordinary skill in the art that variations and modifications of the invention can be made without departing from the spirit or scope of the invention.

We claim:

1. A compound according to Formula II or Formula VI:

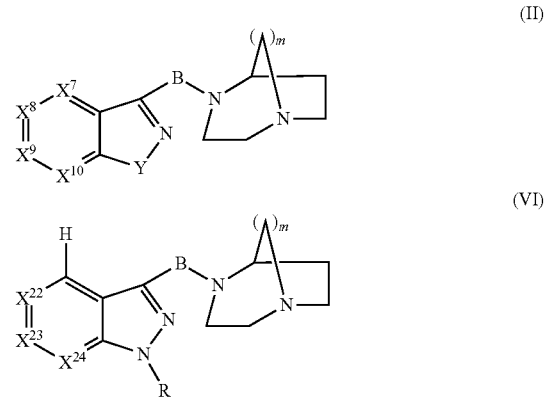

wherein

B is CH$_2$, C=O, or C=S;

R is H, alkyl having 1 to 4 carbon atoms, halogenated alkyl having 1 to 4 carbon atoms, cycloalkyl having 3 to 7 carbon atoms, cycloalkylalkyl having 4 to 7 carbon atoms, or —C$_{1-6}$alkyl-Ar;

m is 2;

Y is S;

X$^7$, X$^8$, X$^9$ and X$^{10}$ are each, independently, N, CH, or CR$^2$, wherein at most one of X$^7$, X$^8$, X$^9$ and X$^{10}$ is N;

R$^1$ and R$^2$ are each, independently,

C$_{1-6}$-alkyl which is unsubstituted or substituted one or more times by F, Cl, Br, I, CN, OR$^{16}$, NR$^6$R$^7$, SH, SR$^6$, SOR$^6$, C$_{3-8}$-cycloalkyl, SO$_2$R$^6$, SO$_2$NR$^6$R$^7$, Ar, Het, or combinations thereof, C$_{2-6}$-alkenyl which is unsubstituted or substituted one or more times by F, Cl, Br, I, CN, OR$^{16}$, NR$^6$R$^7$, SH, SR⁶, SOR⁶, C₃₋₈-cycloalkyl, SO₂R⁶, SO₂NR⁶R⁷, Ar, Het, or combinations thereof, C₂₋₆-alkynyl which is unsubstituted or substituted one or more times by F, Cl, Br, I, CN, OR¹⁶, NR⁶R⁷, SH, SR⁶, SOR⁶, C₃₋₈-cycloalkyl, SO₂R⁶, SO₂NR⁶R⁷, Si(R⁸)₃, Ar, Het, or combinations thereof, C₃₋₈-cycloalkyl which is unsubstituted or substituted one or more times by F, Cl, Br, I, CN, OR¹⁶, NR⁶R⁷, SH, SR⁶, SOR⁶, unsubstituted C₃₋₈-cycloalkyl, SO₂R⁶, SO₂NR⁶R⁷, Ar, Het, or combinations thereof, C₄₋₁₀-cycloalkylalkyl which is unsubstituted or substituted in the cycloalkyl portion one or more times by F, Cl, Br, I, CN, OR¹⁶, NR⁶R⁷, SH, SR⁶, SOR⁶, unsubstituted C₃₋₈-cycloalkyl, SO₂R⁶, SO₂NR⁶R⁷, Ar, Het, or combinations thereof, and/or substituted in the alkyl portion one or more times by F, Cl, Br, I, CN, OR¹⁶, NR⁶R⁷, SH, SR⁶, SOR⁶, C₃₋₈-cycloalkyl, SO₂R⁶, SO₂NR⁶R⁷, Ar, Het, or combinations thereof, halogen, CN, NO₂, NR⁶R⁷, SR⁶, SOR⁶, SO₂R⁶, SO₂NR⁶R⁷, NR⁶SO₂R⁷, CONR⁶R⁷, CSNR⁶R⁷, COOR⁶, NR⁶COR⁷, NR⁶CSR⁷, NR⁶CONR⁶R⁷, NR⁶CSNR⁶R⁷, NR⁶COOR⁷, NR⁶CSOR⁷, OCONR⁶R⁷, OCSNR⁶R⁷, Ar,
Het, or
OR⁹;

R⁶ and R⁷ are each independently
H,

C₁₋₆-alkyl which is unsubstituted or substituted one or more times by F, Cl, Br, I, CN, OR¹⁶, monoalkylamino having 1 to 6 carbon atoms, dialkylamino wherein each alkyl group has 1 to 6 carbon atoms, C₃₋₈-cycloalkyl, Ar, Het, or combinations thereof, C₃₋₆-alkenyl which is unsubstituted or substituted one or more times by F, Cl, Br, I, CN, OR¹⁶, monoalkylamino having 1 to 6 carbon atoms, dialkylamino wherein each alkyl group has 1 to 6 carbon atoms, C₃₋₈-cycloalkyl, Ar, Het, or combinations thereof, C₃₋₆-alkynyl which is unsubstituted or substituted one or more times by F, Cl, Br, I, CN, OR¹⁶, monoalkylamino having 1 to 6 carbon atoms, dialkylamino wherein each alkyl group has 1 to 6 carbon atoms, C₃₋₈-cycloalkyl, Si(R⁸)₃, Ar, Het, or combinations thereof, C₃₋₈-cycloalkyl which is unsubstituted or substituted one or more times by F, Cl, Br, I, CN, OR¹⁶, monoalkylamino having 1 to 6 carbon atoms, dialkylamino wherein each alkyl group has 1 to 6 carbon atoms, C₃₋₈-cycloalkyl, Ar, Het, or combinations thereof, C₄₋₁₀-cycloalkylalkyl which is unsubstituted or substituted in the cycloalkyl portion one or more times by F, Cl, Br, I, CN, OR¹⁶, monoalkylamino having 1 to 6 carbon atoms, dialkylamino wherein each alkyl group has 1 to 6 carbon atoms, C₃₋₈-cycloalkyl, Ar, Het, or combinations thereof, and/or substituted in the alkyl portion one or more times by F, Cl, Br, I, CN, OR¹⁶, monoalkylamino having 1 to 6 carbon atoms, dialkylamino wherein each alkyl group has 1 to 6 carbon atoms, C₃₋₈-cycloalkyl, Ar, Het, or combinations thereof, Ar, or
Het;
R⁸ is C₁₋₆-alkyl;
R⁹ is H, C₁₋₆-alkyl which is unsubstituted or substituted one or more by F, Cl, Br, I, CN, OR¹⁶, NR⁶R⁷, SH, SR⁶, SOR⁶, C₃₋₈-cycloalkyl, SO₂R⁶, SO₂NR⁶R⁷, Ar, Het, or combinations thereof, C₃₋₆-alkenyl which is unsubstituted or substituted one or more times by F, Cl, Br, I, CN, OR¹⁶, NR⁶R⁷, SH, SR⁶, SOR⁶, C₃₋₈-cycloalkyl, SO₂R⁶, SO₂NR⁶R⁷, Ar, Het, or combinations thereof, C₃₋₆-alkynyl which is unsubstituted or substituted one or more times by F, Cl, Br, I, CN, OR¹⁶, NR⁶R⁷, SH, SR⁶, SOR⁶, C₃₋₈-cycloalkyl, SO₂R⁶, SO₂NR⁶R⁷, Ar, Het, or combinations thereof, C₃₋₈-cycloalkyl which is unsubstituted or substituted one or more times by F, Cl, Br, I, CN, OR¹⁶, NR⁶R⁷, SH, SR⁶, SOR⁶, unsubstituted C₃₋₈-cycloalkyl, SO₂R⁶, SO₂NR⁶R⁷, Ar, Het, or combinations thereof, C₄₋₈-cycloalkylalkyl which is unsubstituted or substituted one or more times by F, Cl, Br, I, CN, OR¹⁶, NR⁶R⁷, SH, SR⁶, SOR⁶, unsubstituted C₃₋₈-cycloalkyl, SO₂R⁶, SO₂NR⁶R⁷, Ar, Het, or combinations thereof, Ar, or
Het;

R¹⁰ is H, alkyl having 1 to 4 carbon atoms, halogenated alkyl having 1 to 4 carbon atoms, cycloalkyl having 3 to 7 carbon atoms, or cycloalkylalkyl having 4 to 7 carbon atoms;

X²² and X²³ are each, independently, CH or CR¹²;

X²⁴ is CH;

R¹² is halogen, C₁₋₆-alkoxy which is substituted one or more times by F, —NHCONH—C₁₋₄-alkyl, Ar, Ar—C₁₋₄-alkyl-O—, or is selected from Formulae IX, X, and XI

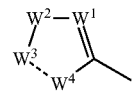

(IX)

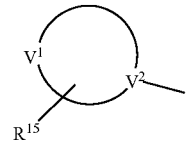

(X)

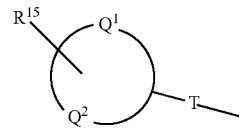

(XI)

wherein Formula IX represents a 5-membered, unsaturated heterocycle in which the bond between W² and W³ is a single bond and the bond between W³ and W⁴ is a double bond, or the bond between W² and W³ is a double bond and the bond between W³ and W⁴ is a single bond, Formula X represents a 5-8-membered, heterocycle which is saturated or partially saturated and wherein the heterocyclic ring may be bridged by a divalent alkylene group having 1 to 3 carbon atoms and may be optionally substituted by oxo, and Formula XI represents a 5-8-membered, heterocycle which is saturated, partially saturated, or unsaturated and wherein the heterocyclic ring may be bridged by a divalent alkylene group having 1 to 3 carbon atoms;

$Q^1$ is O, S, N, $NR^{13}$, or $SO_2$;
$Q^2$ is CH, $CR^{14}$, $CHR^{14}$, O, S, $SO_2$, N, or $NR^{13}$;
T is O or $NR^{10}$;
$V^1$ is O, S, $SO_2$, N, $NR^{13}$, $CR^{14}$, or $CHR^{14}$;
$W^1$ is N;
$W^2$ and $W^3$ are each, independently, O, S, N, $NR^{13}$, CH, or $CR^1$, in which the bond between $W^2$ and $W^3$ is a single bond and the bond between $W^3$ and $W^4$ is a double bond, or the bond between $W^2$ and $W^3$ is a double bond and the bond between $W^3$ and $W^4$ is a single bond;
$W^4$ is O, S, N, or $NR^{13}$;
$V^2$ is C, CH, C—OH, or N;
$R^{13}$ is H,
  $C_{1-6}$-alkyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof,
  $C_{3-6}$-alkenyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof,
  $C_{3-6}$-alkynyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, $Si(R^8)_3$, Ar, Het, or combinations thereof,
  $C_{3-8}$-cycloalkyl which is unsubstituted or substituted one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof,
  $C_{4-10}$-cycloalkylalkyl which is unsubstituted or substituted in the cycloalkyl portion one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof, and/or substituted in the alkyl portion one or more times by F, Cl, Br, I, CN, $OR^{16}$, $NR^6R^7$, SH, $SR^6$, $SOR^6$, $C_{3-8}$-cycloalkyl, $SO_2NR^6R^7$, Ar, Het, or combinations thereof,
  $SO_2R^6$, $CONR^6R^7$, $CSNR^6R^7$, $COOR^6$, $CSOR^6$, $COR^7$, $CSR^7$,
  Ar, or
  Het;
$R^{14}$ is H,
  $C_{1-6}$-alkyl which is unsubstituted or substituted one or more times by F, Cl, Br, I, CN, $OR^9$, $NR^6R^7$, SH, $SR^6$, $SOR^6$, $C_{3-8}$-cycloalkyl, $SO_2R^6$, $SO_2NR^6R^7$, Ar, Het, or combinations thereof,
  $C_{2-6}$-alkenyl which is unsubstituted or substituted one or more times by F, Cl, Br, I, CN, $OR^9$, $NR^6R^7$, SH, $SR^6$, $SOR^6$, $C_{3-8}$-cycloalkyl, $SO_2R^6$, $SO_2NR^6R^7$, Ar, Het, or combinations thereof,
  $C_{2-6}$-alkynyl which is unsubstituted or substituted one or more times by F, Cl, Br, I, CN, $OR^9$, $NR^6R^7$, SH, $SR^6$, $SOR^6$, $C_{3-8}$-cycloalkyl, $SO_2R^6$, $SO_2NR^6R^7$, $Si(R^8)_3$, Ar, Het, or combinations thereof,
  $C_{3-8}$-cycloalkyl which is unsubstituted or substituted one or more times by F, Cl, Br, I, CN, $OR^9$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof,
  $C_{4-10}$-cycloalkylalkyl which is unsubstituted or substituted in the cycloalkyl portion one or more times by F, Cl, Br, I, CN, $OR^9$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof, and/or substituted in the alkyl portion one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof,
  halogen,
  CN, $NO_2$, $NR^6R^7$, $SR^6$, $SOR^6$, $SO_2R^6$, $SO_2NR^6R^7$, $NR^6SO_2R^7$, $CONR^6R^7$, $CSNR^6R^7$, $COOR^6$, $NR^6COR^7$, $NR^6CSR^7$, $NR^6CONR^6R^7$, $NR^6CSNR^6R^7$, $NR^6COOR^7$, $NR^6CSOR^7$, $OCONR^6R^7$, $OCSNR^6R^7$,
  Ar,
  Het, or
  $OR^9$;
$R^{15}$ is H,
  $C_{1-6}$-alkyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof,
  $C_{2-6}$-alkenyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof,
  $C_{2-6}$-alkynyl which is unsubstituted or substituted one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, $Si(R^8)_3$, Ar, Het, or combinations thereof,
  $C_{3-8}$-cycloalkyl which is unsubstituted or substituted one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof,
  $C_{4-10}$-cycloalkylalkyl which is unsubstituted or substituted in the cycloalkyl portion one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof, and/or substituted in the alkyl portion one or more times by F, Cl, Br, I, CN, $OR^{16}$, $NR^6R^7$, SH, $SR^6$, $SOR^6$, $C_{3-8}$-cycloalkyl, $SO_2R^6$, $SO_2NR^6R^7$, Ar, Het, or combinations thereof,
  $C_{3-8}$-cycloalkyloxy which is unsubstituted or substituted one or more times by F, Cl, Br, I, CN, $OR^{16}$, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof,
  halogen,
  oxo, thio, CN, $NO_2$, $NR^6R^7$, $SR^6$, $SOR^6$, $SO_2R^6$, $SO_2NR^6R^7$, $NR^6SO_2R^7$, $CONR^6R^7$, $CSNR^6R^7$, $COOR^6$, $NR^6COR^7$, $NR^6CSR^7$, $NR^6CONR^6R^7$, $NR^6CSNR^6R^7$, $NR^6COOR^7$, $NR^6CSOR^7$, $OCONR^6R^7$, $OCSNR^6R^7$,
  Ar,
  Het, or
  $OR^9$;
$R^{16}$ is H,
  $C_{1-6}$-alkyl which is unsubstituted or substituted one or more by F, Cl, Br, I, CN, OH, alkoxy having 1 to 4 carbon atoms, $NR^6R^7$, SH, $SR^6$, $SOR^6$, $C_{3-8}$-cycloalkyl, $SO_2R^6$, $SO_2NR^6R^7$, Ar, Het, or combinations thereof,
  $C_{3-8}$-cycloalkyl which is unsubstituted or substituted one or more times by F, Cl, Br, I, CN, OH, alkoxy having 1 to 4 carbon atoms, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof, or
  $C_{4-8}$-cycloalkylalkyl which is unsubstituted or substituted one or more times by F, Cl, Br, I, CN, OH, alkoxy having 1 to 4 carbon atoms, $NR^6R^7$, SH, $SR^6$, $SOR^6$, unsubstituted $C_{3-8}$-cycloalkyl, $SO_2R^6$, $SO_2NR^6R^7$, Ar, Het, or combinations thereof;
Ar is an aryl group containing 6 to 10 carbon atoms which is unsubstituted or substituted one or more times by
  alkyl having 1 to 8 carbon atoms,
  alkoxy having 1 to 8 carbon atoms, halogen,
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
carboxy,
alkoxycarbonyl,
alkylaminocarbonyl,
acylamido,
acyloxy,
alkylthio having 1 to 8 carbon atoms,
alkylsulphinyl having 1 to 8 carbon atoms,
alkylsulphonyl having 1 to 8 carbon atoms,
sulfo,
sulfonylamino,
Het,
cycloalkylamino wherein the cycloalkyl group has 3 to 7 C atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio,
aryloxy wherein the aryl portion contains 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio,
arylthio wherein the aryl portion contains 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio,
cycloalkyloxy wherein the cycloalkyl group has 3 to 7 C atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, or
combinations thereof, and
Het is a heterocyclic group which is fully saturated, partially saturated or fully unsaturated, having 5 to 10 ring atoms in which at least 1 ring atom is a N, O or S atom, which is unsubstituted or substituted one or more times by
alkyl having 1 to 8 carbon atoms,
alkoxy having 1 to 8 carbon atoms,
cycloalkyl having 3 to 8 carbon atoms,
cycloalkylalkyl having 4 to 8 carbon atoms,
halogen,
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
carboxy,
alkoxycarbonyl,
alkylaminocarbonyl,
acylamido,
acyloxy,
alkylthio having 1 to 8 carbon atoms,
alkylsulphinyl having 1 to 8 carbon atoms,
alkylsulphonyl having 1 to 8 carbon atoms,
sulfo,
oxo,
sulfonylamino,
cycloalkylamino wherein the cycloalkyl group has 3 to 7 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio,
aryl containing 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio,
aryl-alkylene group wherein the aryl portion contains 6 to 10 carbon atoms and the alkylene portion contains 1 to 4 carbon atoms and is unsubstituted or substituted one or more times by halogen, alkyl having 1 to 8 C atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio,
aryloxy wherein the aryl portion contains 6 to 10 carbon atoms and is optionally substituted by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio,
arylthio wherein the aryl portion contains 6 to 10 carbon atoms and is optionally substituted by halogen, alkyl having 1 to 8 carbon atoms, halogenated alkyl 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, cycloalkyloxy wherein the cycloalkyl group has 3 to 7 carbon atoms and is optionally substituted by halogen, alkyl having 1 to 8 C carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, heterocyclic group, which is fully saturated, partially saturated or fully unsaturated, having 5 to 10 ring atoms in which at least 1 ring atom is a N, O or S atom, which is unsubstituted or substituted one or more times by halogen, alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^9$, $CSR^9$, cyano, hydroxyl, nitro, oxo, or thio, or combinations thereof; and wherein at least one of $X^8$ or $X^9$ is $CR^2$ in which $R^2$ is Het other than imidazolidinyl or $R^2$ is $OR^9$ in which $R^9$ is Het; and wherein
at least one of $X^{22}$ and $X^{23}$ is $CR^{12}$ in which $R^{12}$ is —NHCO—NH—$C_{1-4}$-alkyl or is selected from pyrrolidinyl, morpholinyl, thiomorpholinyl, piperazinyl, diazepanyl, oxazepanyl, tetrahydro-2H-pyran-3-yloxy, dihydroimidazolyl, and imidazolidinyl, which in each case is unsubstituted or substituted by $R^{15}$; or
a pharmaceutically acceptable salt thereof.

2. A compound according to claim 1, wherein said compound is selected from Formula VI and $X^{22}$ is $CR^{12}$ in which $R^{12}$ is pyrrolidinyl, morpholinyl, thiomorpholinyl, piperazinyl, diazepanyl, oxazepanyl, tetrahydro-2H-pyran-3-yloxy, dihydroimidazolyl, or imidazolidinyl which in each case is unsubstituted or substituted by $R^{15}$.

3. A compound according to claim 1, wherein said compound is selected from Formula VI in which $X^{23}$ is $CR^{12}$ in which $R^{12}$ is pyrrolidinyl, morpholinyl, thiomorpholinyl, piperazinyl, diazepanyl, oxazepanyl, tetrahydro-2H-pyran-3-yloxy, dihydroimidazolyl, or imidazolidinyl, which in each case is unsubstituted or substituted by $R^{15}$.

4. A compound according to claim 3, wherein $X^{23}$ is $CR^{12}$ in which $R^{12}$ is pyrrolidin-1-yl, morpholin-4-yl, thiomorpholin-4-yl, imidazolidin-2-oxo-1-yl, dihydroimidazolyl, 4-methylpiperazin-1-yl, 1,4-diazepan-1-yl, or 1,4-oxazepan-1-yl, which in each case is unsubstituted or substituted by $R^{15}$.

5. A compound according to claim 3, wherein $X^{23}$ is $CR^{12}$ in which $R^{12}$ is tetrahydro-2H-pyran-3-yloxy.

6. A compound according to claim 1, wherein said compound is of Formula II.

7. A compound according to claim 1, wherein said compound is of Formula VI.

8. A compound according to claim 1, wherein said compound is selected from Formula VI in which at least one of $X^{22}$ and $X^{23}$ is $CR^{12}$ in which $R^{12}$ is pyrrolidinyl which is substituted by alkoxy having 1 to 6 carbon atoms, amino, monoalkylamino having 1 to 6 carbon atoms, or dialkylamino wherein each alkyl group has 1 to 6 carbon atoms.

9. A compound according to claim 1, wherein said compound is selected from Formula VI in which R is H or alkyl having 1 to 4 carbon atoms.

10. A compound according to claim 1, wherein said compound is selected from Formula VI in which R is H.

11. A compound according to claim 1, wherein B is CO.

12. A compound according to claim 1, wherein said compound is selected from Formula II in which at least one of $X^8$ or $X^9$ is $CR^2$ in which $R^2$ is Het other than imidazolidinyl or $R^2$ is $OR^9$ and $R^9$ is Het.

13. A compound according to claim 1, wherein said compound is selected from Formula II in which at least one of $X^8$ or $X^9$ is $CR^2$ in which $R^2$ is substituted or unsubstituted pyrrolidinyl, diazabicycloheptyl, diazabicyclononyl, piperazinyl, diazepanyl, hexahydropyrrolopyrazinyl, diazabicyclooctyl, pyrrolidinyloxy, or azabicyclooctyloxy.

14. A compound according to claim 12, wherein B is CO.

15. A compound according to claim 1, wherein said compound is selected from:
3-(1,4-Diazabicyclo[3.2.2]non-4-ylcarbonyl)-6-pyrrolidin-1-yl-1H-indazole,
3-(1,4-Diazabicyclo[3.2.2]non-4-ylcarbonyl)-6-(3-methoxypyrrolidin-1-yl)-1H-indazole,
3-(1,4-Diazabicyclo[3.2.2]non-4-ylcarbonyl)-6-morpholin-4-yl-1H-indazole,
1-[3-(1,4-Diazabicyclo[3.2.2]non-4-ylcarbonyl)-1H-indazol-6-yl]-3-propylimidazolidin-2-one,
3-(1,4-Diazabicyclo[3.2.2]non-4-ylcarbonyl)-6-(4-methyl-1,4-diazepan-1-yl)-1H-indazole,
3-(1,4-Diazabicyclo[3.2.2]non-4-ylcarbonyl)-6-thiomorpholin-4-yl-1H-indazole,
3-(1,4-Diazabicyclo[3.2.2]non-4-ylcarbonyl)-6-(4-methylpiperazin-1-yl)-1H-indazole,
3-(1,4-Diazabicyclo[3.2.2]non-4-ylcarbonyl)-6-(1,4-oxazepan-4-yl)-1H-indazole,
3-(1,4-Diazabicyclo[3.2.2]non-4-ylcarbonyl)-6-[(3R)-3-methoxypyrrolidin-1-yl]-1H-indazole,
3-(1,4-Diazabicyclo[3.2.2]non-4-ylcarbonyl)-5-[(3S)-3-methoxypyrrolidin-1-yl]-1H-indazole,
3-(1,4-Diazabicyclo[3.2.2]non-4-ylcarbonyl)-5-[(3R)-3-methoxypyrrolidin-1-yl]-1H-indazole,
3-(1,4-Diazabicyclo[3.2.2]non-4-ylcarbonyl)-6-[(3S)-3-methoxypyrrolidin-1-yl]-1H-indazole,
3-(1,4-Diazabicyclo[3.2.2]non-4-ylcarbonyl)-5-(tetrahydro-2H-pyran-3-yloxy)-1H-indazole,
3-(1,4-Diazabicyclo[3.2.2]non-4-ylcarbonyl)-6-(tetrahydro-2H-pyran-3-yloxy)-1H-indazole,
3-(1,4-Diazabicyclo[3.2.2]non-4-ylcarbonyl)-6-[(3R)-3-methoxypyrrolidin-1-yl]-1,2-benzisothiazole,
3-(1,4-Diazabicyclo[3.2.2]non-4-ylcarbonyl)-6-[(3S)-3-methoxypyrrolidin-1-yl]-1,2-benzisothiazole,
N-[3-(1,4-Diazabicyclo[3.2.2]non-4-ylcarbonyl)-1-methyl-1H-indazol-6-yl]-N'-propylurea hydroformate,
3-(1,4-Diazabicyclo[3.2.2]non-4-ylcarbonyl)-6-[(1S,4S)-5-methyl-2,5-diazabicyclo[2.2.1]hept-2-yl]-1,2-benzisothiazole,
3-(1,4-Diazabicyclo[3.2.2]non-4-ylcarbonyl)-6-[(1R,4R)-5-methyl-2,5-diazabicyclo[2.2.1]hept-2-yl]-1,2-benzisothiazole,
6-(1,4-Diazabicyclo[3.2.2]non-4-yl)-3-(1,4-diazabicyclo[3.2.2]non-4-ylcarbonyl)-1,2-benzisothiazole,
3-(1,4-Diazabicyclo[3.2.2]non-4-ylcarbonyl)-5-[4-(2,2,2-trifluoroethyl)-1,4-diazepan-1-yl]-1H-indazole,
3-(1,4-Diazabicyclo[3.2.2]non-4-ylcarbonyl)-6-pyrrolidin-1-yl-1,2-benzisothiazole,
3-(1,4-Diazabicyclo[3.2.2]non-4-ylcarbonyl)-6-(4-methylpiperazin-1-yl)-1,2-benzisothiazole, 3-(1,4-Diazabicyclo[3.2.2]non-4-ylcarbonyl)-6-(4-methyl-1,4-diazepan-1-yl)-1,2-benzisothiazole,
3-(1,4-Diazabicyclo[3.2.2]non-4-ylcarbonyl)-6-(hexahydropyrrolo[1,2-a]pyrazin-2(1H)-yl)-1,2-benzisothiazole,
3-(1,4-Diazabicyclo[3.2.2]non-4-ylcarbonyl)-6-(5-methyl-2,5-diazabicyclo[2.2.2]oct-2-yl)-1,2-benzisothiazole,
6-[(1S,4S)-5-cyclopropyl-2,5-diazabicyclo[2.2.1]hept-2-yl]-3-(1,4-diazabicyclo[3.2.2]non-4-ylcarbonyl)-1,2-benzisothiazole,
6-[(1S,4S)-5-(cyclopropylmethyl)-2,5-diazabicyclo[2.2.1]hept-2-yl]-3-(1,4-diazabicyclo[3.2.2]non-4-ylcarbonyl)-1,2-benzisothiazole,
tert-Butyl (1S,4S)-5-[3-(1,4-diazabicyclo[3.2.2]non-4-ylcarbonyl)-1,2-benzisothiazol-6-yl]-2,5-diazabicyclo[2.2.1]heptane-2-carboxylate,
6-[(1S,4S)-2,5-Diazabicyclo[2.2.1]hept-2-yl]-3-(1,4-diazabicyclo[3.2.2]non-4-ylcarbonyl)-1,2-benzisothiazole,
3-(1,4-Diazabicyclo[3.2.2]non-4-ylcarbonyl)-6-[(1-methylpyrrolidin-3-yl)oxy]-1,2-benzisothiazole,
6-(1-Azabicyclo[2.2.2]oct-3-yloxy)-3-(1,4-diazabicyclo[3.2.2]non-4-ylcarbonyl)-1,2-benzisothiazole, and
3-(1,4-Diazabicyclo[3.2.2]non-4-ylcarbonyl)-6-(1-methyl-4,5-dihydro-1H-imidazol-2-yl)-1H-indazole,
and pharmaceutically acceptable salts thereof,
wherein a compound listed above, in either a free base form or in the form of a pharmaceutically acceptable salt, can also be in the form of an N-oxide, and
wherein if the compound exhibits chirality it can be in the form of a mixture of enantiomers or diastereomers, or can be in the form of a single enantiomer or a single diastereomer.

16. A compound selected from:
3-(1,4-Diazabicyclo[3.2.2]non-4-ylcarbonyl)-6-pyrrolidin-1-yl-1H-indazole,
3-(1,4-Diazabicyclo[3.2.2]non-4-ylcarbonyl)-6-(3-methoxypyrrolidin-1-yl)-1H-indazole,
3-(1,4-Diazabicyclo[3.2.2]non-4-ylcarbonyl)-6-morpholin-4-yl-1H-indazole,
1-[3-(1,4-Diazabicyclo[3.2.2]non-4-ylcarbonyl)-1H-indazol-6-yl]-3-propylimidazolidin-2-one,
3-(1,4-Diazabicyclo[3.2.2]non-4-ylcarbonyl)-6-(4-methyl-1,4-diazepan-1-yl)-1H-indazole,
3-(1,4-Diazabicyclo[3.2.2]non-4-ylcarbonyl)-6-thiomorpholin-4-yl-1H-indazole,
3-(1,4-Diazabicyclo[3.2.2]non-4-ylcarbonyl)-6-(4-methylpiperazin-l-yl)-1H-indazole,
3-(1,4-Diazabicyclo[3.2.2]non-4-ylcarbonyl)-6-(1,4-oxazepan-4-yl)-1H-indazole,
3-(1,4-Diazabicyclo[3.2.2]non-4-ylcarbonyl)-5-methoxy-1,2-benzisothiazole,
3-(1,4-Diazabicyclo[3.2.2]non-4-ylcarbonyl)-6-[(3R)-3-methoxypyrrolidin-1-yl]-1H-indazole,
3-(1,4-Diazabicyclo[3.2.2]non-4-ylcarbonyl)-5 -[(3S)-3-methoxypyrrolidin-1 -yl]-1H-indazole,
3-(1,4-Diazabicyclo[3.2.2]non-4-ylcarbonyl)-5 -[(3R)-3-methoxypyrrolidin-1 -yl]-1H-indazole,
3-(1,4-Diazabicyclo[3.2.2]non-4-ylcarbonyl)-6-[(3S)-3-methoxypyrrolidin-1 -yl]-1H-indazole,
3-(1,4-Diazabicyclo[3.2.2]non-4-ylcarbonyl)-5 - (tetrahydro-2H-pyran-3-yloxy)-1H-indazole,
3-(1,4-Diazabicyclo[3.2.2]non-4-ylcarbonyl)-6-(tetrahydro-2H-pyran-3-yloxy)-1H-indazole,
3-(1,4-Diazabicyclo[3.2.2]non-4-ylcarbonyl)-6-[(3R)-3-methoxypyrrolidin-1 -yl]-1,2-benzisothiazole,
3-(1,4-Diazabicyclo[3.2.2]non-4-ylcarbonyl)-7 -fluoro-6-methoxy-1,2-benzisothiazole,
3-(1,4-Diazabicyclo[3.2.2]non-4-ylcarbonyl)-6-[(3S)-3-methoxypyrrolidin-1-yl]-1,2-benzisothiazole,
N-[3-(1,4-Diazabicyclo[3.2.2]non-4-ylcarbonyl)-1-methyl-1H-indazol-6-yl]-N-propylurea,
3-(1,4-Diazabicyclo[3.2.2]non-4-ylcarbonyl)-1-ethyl-6-methoxy-1H-indazole,
3-(1,4-Diazabicyclo[3.2.2]non-4-ylcarbonyl)-6-[(1S,4S)-5-methyl-2,5-diazabicyclo[2.2.1]hept-2-yl]-1,2-benzisothiazole,
3-(1,4-Diazabicyclo[3.2.2]non-4-ylcarbonyl)-6-[(1R,4R)-5-methyl-2,5-diazabicyclo[2.2.1]hept-2-yl]-1,2-benzisothiazole,
6-(1,4-Diazabicyclo[3.2.2]non-4-yl)-3-(1,4-diazabicyclo[3.2.2]non-4-ylcarbonyl)-1,2-benzisothiazole,
3-(1,4-Diazabicyclo[3.2.2]non-4-ylcarbonyl)-5-[4-(2,2,2-trifluoroethyl)-1,4-diazepan-1-yl]-1H-indazole,
3-(1,4-Diazabicyclo[3.2.2]non-4-ylcarbonyl)-6-pyrrolidin-1-yl-1,2-benzisothiazole,
3-(1,4-Diazabicyclo[3.2.2]non-4-ylcarbonyl)-6-(4-methylpiperazin-1-yl)-1,2-benzisothiazole,
3-(1,4-Diazabicyclo[3.2.2]non-4-ylcarbonyl)-6-(4-methyl-1,4-diazepan-1-yl)-1,2-benzisothiazole
3-(1,4-Diazabicyclo[3.2.2]non-4-ylcarbonyl)-6-(hexahydropyrrolo[1,2-a]pyrazin-2(1H)-yl)-1,2-benzisothiazole,
3-(1,4-Diazabicyclo[3.2.2]non-4-ylcarbonyl)-6-(5-methyl-2,5-diazabicyclo[2.2.2]oct-2-yl)-1,2-benzisothiazole,
6-[(1S,4S)-5-cyclopropyl-2,5-diazabicyclo[2.2.1]hept-2-yl]-3-(1,4-diazabicyclo[3.2.2]non-4-ylcarbonyl)-1,2-benzisothiazole,
6-[(1S,4S)-5-(cyclopropylmethyl)-2,5-diazabicyclo[2.2.1]hept-2-yl]-3-(1,4-diazabicyclo[3.2.2]non-4-ylcarbonyl)-1,2-benzisothiazole,
tert-Butyl (1S,4S)-5-[3-(1,4-diazabicyclo[3.2.2]non-4-ylcarbonyl)-1,2-benzisothiazol-6-yl]-2,5-diazabicyclo[2.2.1]heptane-2-carboxylate,
6-[(1S,4S)-2,5-Diazabicyclo[2.2.1]hept-2-yl]-3-(1,4-diazabicyclo[3.2.2]non-4-ylcarbonyl)-1,2-benzisothiazole,
3-(1,4-Diazabicyclo[3.2.2]non-4-ylcarbonyl)-6- [(1-methylpyrrolidin-3-yl)oxy]-1,2-benzisothiazole,
6-(1-Azabicyclo[2.2.2]oct-3-yloxy)-3-(1,4-diazabicyclo[3.2.2]non-4-ylcarbonyl)-1,2-benzisothiazole,
6-(Benzyloxy)-3-(1,4-diazabicyclo[3.2.2]non-4-ylcarbonyl)-1H-indazole,
3-(1,4-Diazabicyclo[3.2.2]non-4-ylcarbonyl)-6-(1-methyl-4,5-dihydro-1H-imidazol-2-yl)-1H-indazole,
and pharmaceutically acceptable salts thereof,
wherein a compound listed above, in either a free base form or in the form of a pharmaceutically acceptable salt, can also be in the form of an N-oxide, and
wherein if the compound exhibits chirality it can be in the form of a mixture of enantiomers or diastereomers, or can be in the form of a single enantiomer or a single diastereomer.

17. A compound according to claim 16, wherein said compound is in the form of a hydroformate salt thereof.

18. A compound according to claim 16, wherein said compound selected from:
3-(1,4-Diazabicyclo[3.2.2]non-4-ylcarbonyl)-6-pyrrolidin-1-yl-1H-indazole,
3-(1,4-Diazabicyclo[3.2.2]non-4-ylcarbonyl)-6-(3-methoxypyrrolidin-1-yl)-1H-indazole, 3-(1,4-Diazabicyclo[3.2.2]non-4-ylcarbonyl)-6-morpholin-4-yl-1H-indazole,
1-[3-(1,4-Diazabicyclo[3.2.2]non-4-ylcarbonyl)-1H-indazol-6-yl]-3-propylimidazolidin-2-one,
3-(1,4-Diazabicyclo[3.2.2]non-4-ylcarbonyl)-6-(4-methyl-1,4-diazepan-1-yl)-1H-indazole,
3-(1,4-Diazabicyclo[3.2.2]non-4-ylcarbonyl)-6-thiomorpholin-4-yl-1H-indazole,
3-(1,4-Diazabicyclo[3.2.2]non-4-ylcarbonyl)-6-(4-methylpiperazin-1-yl)-1H-indazole,
3-(1,4-Diazabicyclo[3.2.2]non-4-ylcarbonyl)-6-(1,4-oxazepan-4-yl)-1H-indazole,
3-(1,4-Diazabicyclo[3.2.2]non-4-ylcarbonyl)-5-methoxy-1,2-benzisothiazole hydroformate, and
and pharmaceutically acceptable salts thereof,
 wherein a compound listed above, in either a free base form or in the form of a pharmaceutically acceptable salt, can also be in the form of an N-oxide, and
 wherein if the compound exhibits chirality it can be in the form of a mixture of enantiomers or diastereomers, or can be in the form of a single enantiomer or a single diastereomer.

19. A pharmaceutical composition comprising a compound according to claim 1 and a pharmaceutically acceptable carrier.

20. A compound according to claim 1, wherein said compound is selected from:

3-(1,4-Diazabicyclo[3.2.2]non-4-ylcarbonyl)-6-[(3R)-3-methoxypyrrolidin-1-yl]-1H-indazole dihydroformate,
3-(1,4-Diazabicyclo[3.2.2]non-4-ylcarbonyl)-5-[(3S)-3-methoxypyrrolidin-1-yl]-1H-indazole dihydroformate,
3-(1,4-Diazabicyclo[3.2.2]non-4-ylcarbonyl)-5-[(3R)-3-methoxypyrrolidin-1-yl]-1H-indazole dihydroformate, and
3-(1,4-Diazabicyclo[3.2.2]non-4-ylcarbonyl)-6-[(3S)-3-methoxypyrrolidin-1-yl]-1H-indazole dihydroformate.

21. A compound according to claim 7, wherein B is CO, R is H, $X^{24}$ is CH, $X^{23}$ is $CR^{12}$, and $R^{12}$ is pyrrolidinyl, morpholinyl, thiomorpholinyl, imidazolidinyl, dihydroimidazolyl, piperazinyl, diazepanyl, and oxazepanyl, which in each case is unsubstituted or substituted by $R^{15}$.

22. A compound according to claim 7, wherein B is CO, R is H, $X^{24}$ is CH, $X^{23}$ is $CR^{12}$, and $R^{12}$ is pyrrolidin-1-yl, morpholin-4-yl, thiomorpholin-4-yl, imidazolidin-2-oxo-1-yl, dihydroimidazolyl, 4-methylpiperazin-1-yl, 1,4-diazepan-1-yl, 1,4-oxazepan-1-yl, which in each case is unsubstituted or substituted by $R^{15}$.

23. A compound according to claim 7, wherein B is CO, R is H, $X^{22}$ is CH, $X^{24}$ is CH, $X^{23}$ is $CR^{12}$, and $R^{12}$ is pyrrolidin-1-yl, morpholin-4-yl, thiomorpholin-4-yl, imidazolidin-2-oxo-1-yl, dihydroimidazolyl, 4-methylpiperazin-1-yl, 1,4-diazepan-1-yl, 1,4-oxazepan-1-yl, which in each case is unsubstituted or substituted by $R^{15}$.

* * * * *